(12) United States Patent
Gotanda et al.

(10) Patent No.: US 8,293,754 B2
(45) Date of Patent: Oct. 23, 2012

(54) THIENOPYRIMIDINE DERIVATIVES

(75) Inventors: Kotaro Gotanda, Kawasaki (JP); Atsushi Shinbo, Niiza (JP); Youichi Nakano, Kawasaki (JP); Hideo Kobayashi, Saitama (JP); Makoto Okada, Kawasaki (JP); Akira Asagarasu, Machida (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 969 days.

(21) Appl. No.: 11/922,233

(22) PCT Filed: Jun. 13, 2006

(86) PCT No.: PCT/JP2006/312203
§ 371 (c)(1),
(2), (4) Date: Nov. 24, 2008

(87) PCT Pub. No.: WO2006/135080
PCT Pub. Date: Dec. 21, 2006

(65) Prior Publication Data
US 2009/0203703 A1  Aug. 13, 2009

(30) Foreign Application Priority Data
Jun. 14, 2005 (JP) .................................. 2005-173898

(51) Int. Cl.
*C07D 495/04* (2006.01)
*A61K 31/519* (2006.01)
*A61P 25/28* (2006.01)

(52) U.S. Cl. .................................... 514/260.1; 544/278
(58) Field of Classification Search ................ 544/278; 514/260.1
See application file for complete search history.

(56) References Cited

U.S. PATENT DOCUMENTS
5,075,310 A  12/1991  Coates et al.

FOREIGN PATENT DOCUMENTS
| JP | 53015136 | * | 2/1978 |
| JP | 02-056484 |   | 2/1990 |
| WO | 02/064080 |   | 8/2002 |
| WO | 03/037432 |   | 5/2003 |
| WO | 03/037899 |   | 5/2003 |
| WO | 2004/018474 |   | 3/2004 |

OTHER PUBLICATIONS

Van der Staay et. al. (Neuropharmacology, 2008, 55, pp. 908-918).*
Douglas A. Fisher et al. "*Isolation and Characterization of PDE9A, a Novel Human cGMP-specific Phosphodoesterase*", The Journal of Biological Chemistry, vol. 273, No. 25, Issue of Jun. 19, pp. 15559-15564 (1998).
Supplementary European Search Report issued Sep. 29, 2010 in corresponding European Patent Application No. 06 76 6867.

* cited by examiner

*Primary Examiner* — Susanna Moore
(74) *Attorney, Agent, or Firm* — Wenderoth, Lind & Ponack, L.L.P.

(57) ABSTRACT

This invention provides thienopyrimidine derivatives of the formula,

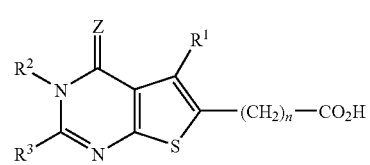

(I)

wherein $R^1$ stands for hydrogen atom, an alkyl group or the like; $R^2$ stands for a hydrogen atom, an alkyl or amino group or the like, $R^3$ stands for an alkyl, alkenyl or alkylthio group or the like or a group Y—X—; or $R^2$ and $R^3$ may together form tetramethylene group; X standing for a direct bond or linking group such as $CH_2$, $CH(OH)$, S, O, NH; Y standing for a substituted or unsubstituted aromatic carbocyclic, aromatic heterocyclic, cycloalkyl or saturated heterocyclic group or the like; Z stands for S or O, and n is 0 or an integer of 1 to 4, or salts thereof, which exhibit an inhibitory effect on PDE9, and are therefore useful for prevention or treatment of overactive bladder syndrome, pollakiuria, urinary incontinence, dysuria associated with prostatic hyperplasia, urolithiasis, Alzheimer's disease, chronic obstructive pulmonary disease, myocardial infarction, thrombosis, diabetes and the like.

21 Claims, No Drawings

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Synthetic Construct

<400> SEQUENCE: 1
ctagctagcc accatgggat ccggctcctc c                                    31

<210> SEQ ID NO 2
<211> LENGTH: 43
<212> TYPE: DNA
<213> ORGANISM: Artificial Sequence
<220> FEATURE:
<223> OTHER INFORMATION: Synthetic Construct

<400> SEQUENCE: 2
ttttcctttt gcggccgctt attaggcaca gtctccttca ctg                       43

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
cggaattcca accatggagc gggc                                            24

<210> SEQ ID NO 4
<211> LENGTH: 27
<212> TYPE: DNA
<213> ORGANISM: Artificial Sequence
<220> FEATURE:
<223> OTHER INFORMATION: Synthetic Construct

<400> SEQUENCE: 4
gctctagatc agttccgctt ggcctgg                                         27
```

THIENOPYRIMIDINE DERIVATIVES

TECHNICAL FIELD

This invention relates to novel thienopyrimidine derivatives and salts thereof, which exhibit type 9 phosphodiesterase (PDE9)-inhibiting activity and are useful as treating agent of dysuria and the like.

BACKGROUND ART

Dysuria can be largely divided into emptying disorder due to inability to urinate with sufficient force at the time of emptying the bladder, and bladder-filling disorder due to inability to retain urine during the filling time. Presently, $\alpha_1$ blocker is frequently used for treating the emptying disorder and anticholine agent, for treating bladder-filling disorder. These drugs, however, have such defects as insufficient long-term therapeutic effect or reduction in quality of life (QOL) induced by side effect, and development of drugs having new activity mechanism different from the conventional approach, for example, drugs utilizing potassium channel opening activity, cyclic guanosine-3',5'-monophosphate (cGMP) degradation inhibiting activity, are in demand.

cGMP plays an important role in variegated cellular phenomena such as smooth muscle relaxation, memory and learning function control, photoreaction of retina, cell proliferation, immunoreaction and the like, and drop in intracellular cGMP concentration causes disorder in cell functions. Synthesis of cGMP by nitrogen monoxide (NO)-cGMP system and degradation of cGMP by PDE system are continually progressing in the cells each at a constant rate and good balance of the two are maintained in normal cells. Whereas, within the cells under various states of disorder, function of the NO-cGMP system lowers to render the cGMP synthesis level in the cells low. Because the cGMP degradation in the cells progresses at a fixed rate in the meantime, cGMP concentration in the affected cells becomes low. It is expected, therefore, prevention of cGMP degradation in the cells to redress the reduction in intracellular cGMP concentration would be useful for treating or preventing diseases.

While there are many types of PDE, those which specifically decompose cGMP are type 5 (PDE5), type 6 (PDE6) and type 9 (PDE9). Of these, PDE9 shows the least Km value (J. Biol. Chemistry, Vol. 273, No. 25, 15559-15564 (1998), has high affinity to cGMP and is considered to participate in degradation of cGMP with particular significance.

Heretofore, pyrazolopyrimidine derivatives are known as the compounds exhibiting PDE9-inhibiting activity, and as patent literature relating to the derivatives, for example, there are PCT International Publication WO 03/037432 Pamphlet disclosing their utility for treating insulin-resistant diseases, WO 03/037899 Pamphlet disclosing their utility for treating cardiovascular disorder, and WO 2004/018474 Pamphlet disclosing their utility for improving perception, learning and memory functions.

Whereas, thienopyrimidine derivatives having PDE9-inhibiting activity are heretofore entirely unknown, and there is no existing literature discussing relevancy between PDE9-inhibiting activity and therapeutic effect on dysuria.

Screening library of Ambinter Co. posts a thienopyrimidine derivative represented by the following formula:

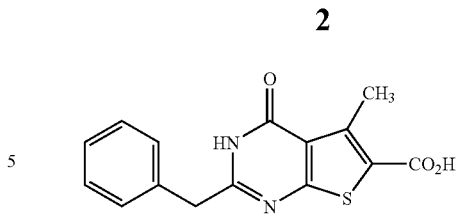

but catalogues, pamphlets and the like materials issued by the same company give no information including activity on this compound.

DISCLOSURE OF THE INVENTION

The object of the present invention is to provide novel thienopyrimidine derivatives which have PDE9-inhibiting action and are useful as treating agent for disorders including dysuria.

We have discovered, after ardent research activities, that inhibition of PDE9 is effective for treating dysuria such as overactive bladder syndrome, pollakiuria, urinary incontinence, dysuria in benign prostatic hyperplasia and various diseases relating to urinary tract such as urolithiasis. Based on this discovery, we have created novel thienopyrimidine derivatives having PDE9-inhibiting activity which are useful as dysuria-treating agent, and come to complete the present invention.

According to the present invention, therefore, thienopyrimidine derivatives represented by formula (I)

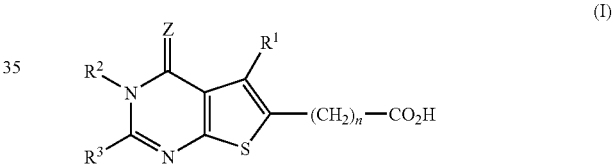

(I)

in which $R^1$ stands for hydrogen, $C_{1-6}$ alkyl, $C_{1-6}$ alkoxy$C_{1-6}$ alkyl or $C_{1-6}$ haloalkyl containing 1-6 halogen atoms, $R^2$ stands for hydrogen, $C_{1-6}$ alkyl, phenyl$C_{1-6}$ alkyl or amino, $R^3$ stands for $C_{2-6}$ alkyl, $C_{2-6}$ alkenyl, carbamoyl$C_{1-6}$ alkyl, amino$C_{1-6}$ alkyl, $C_{1-6}$ alkylamino$C_{1-6}$ alkyl, di-($C_{1-6}$ alkyl) amino$C_{1-6}$ alkyl, $C_{1-6}$ alkylthio or Y—X— group, or $R^2$ and $R^3$ may together form tetramethylene, X standing for a direct bond, or $CH_2$, CH(OH), CH($C_6H_5$), CO, $CH_2CH_2$, $CH_2CO$, $COCH_2$, S, O or NH and Y standing for aromatic carbocyclic group, aromatic heterocyclic group, 4-7-membered cycloalkyl group, 4-7-membered cycloalkenyl group, 5-7-membered saturated heterocyclic group containing 1 or 2 nitrogen atoms, or 5-7-membered saturated heterocyclic group forming a condensed ring with 5 or 6-membered saturated cyclic group and containing 1 or 2 nitrogen atoms, all of these groups optionally containing 1-3 substituents selected from halogen atom, $C_{1-6}$ alkyl, $C_{1-6}$ haloalkyl containing 1-6 halogen atoms, $C_{1-6}$ haloalkyloxy containing 1-6 halogen atoms, $C_{1-6}$ haloalkylthio containing 1-6 halogen atoms, $C_{1-6}$ alkoxy, $C_{1-6}$ alkylthio, $C_{1-4}$ alkylenedioxy, carboxyl, $C_{1-6}$ alkoxycarbonyl, oxo, amino, nitro and phenyl, Z stands for S or O, and n is 0 or an integer of 1-4, with the proviso that a case wherein $R^1$ is methyl, $R^2$ is hydrogen, $R^3$ is benzyl, Z is O and n is 0 is excluded, or salts of the derivatives are provided.

In the present specification, the expressions, "$C_{1-6}$", "$C_{1-4}$" and "$C_{2-6}$" indicate that the carbon numbers in the groups to which these expressions are attached are respectively within the range of given numbers.

"$C_{1-6}$ alkyl" may be linear or branched, examples of which include methyl, ethyl, n-propyl, isopropyl, n-butyl, isobutyl, sec-butyl, tert-butyl, n-pentyl and n-hexyl. Of these, methyl, ethyl, n-propyl, isopropyl and n-butyl are preferred. Also "$C_{2-6}$ alkyl" encompasses those groups defined as to above $C_{1-6}$ alkyl except methyl, among which ethyl, n-propyl, isopropyl and n-butyl are preferred.

"$C_{2-6}$ alkenyl" can have one or plural double bonds at optional position(s) and may be linear or branched, of which specific examples include vinyl, allyl, isopropenyl, 1-butenyl, 2-butenyl, 3-butenyl, 1,3-butadienyl, 2-methylallyl, 1-pentenyl and 1-hexenyl, among which vinyl, allyl and isopropenyl are preferred.

"$C_{1-6}$ alkoxy" is oxy (O) group substituted with $C_{1-6}$ alkyl, of which specific examples include methoxy, ethoxy, n-propoxy, isopropoxy, n-butoxy, isobutoxy, sec-butoxy, tert-butoxy, n-pentyloxy and n-hexyloxy. Of those, methoxy, ethoxy, n-propoxy, isopropoxy and n-butoxy are preferred.

"$C_{1-6}$ alkylthio" is thio (S) group substituted with $C_{1-6}$ alkyl, of which specific examples include methylthio, ethylthio, n-propylthio, isopropylthio, n-butylthio, isobutylthio, sec-butylthio, tert-butylthio, n-pentylthio and n-hexylthio. Of those, methylthio, ethylthio, n-propylthio, isopropylthio and n-butylthio are preferred.

"$C_{1-4}$ alkylenedioxy" includes, for example, methylenedioxy, ethylenedioxy, propylenedioxy and tetramethylenedioxy. Of those, methylenedioxy and ethylenedioxy are preferred.

"4-7-Membered cycloalkyl" includes cyclobutyl, cyclopentyl, cyclohexyl and cycloheptyl. Of those, cyclopentyl and cyclohexyl are preferred.

"Halogen atom" includes fluorine, chlorine, bromine and iodine, fluorine, chlorine and bromine being particularly preferred.

"$C_{1-6}$ haloalkyl containing 1-6 halogen atoms" signifies $C_{1-6}$ alkyl following the earlier given definition, which are substituted with same or different 1-6 halogen atoms, of which specific examples include fluoromethyl, trifluoromethyl, 1,2-dichloroethyl, 1-chloro-2-bromoethyl, pentafluoroethyl, 1-chloro-n-propyl, 2-bromo-2-methylethyl, 3-chloro-n-pentyl and 2-bromo-3-chloro-n-hexyl. Of those, $C_{1-2}$ alkyl substituted with same or different 1-5 halogen atoms are preferred.

Also "$C_{1-6}$ haloalkyloxy containing 1-6 halogen atoms" signifies oxy (O) group substituted with above "$C_{1-6}$ haloalkyl containing 1-6 halogen atoms", and "$C_{1-6}$ haloalkylthio containing 1-6 halogen atoms" signifies thio (S) group substituted with above "$C_{1-6}$ haloalkyl containing 1-6 halogen atoms".

"$C_{1-6}$ alkoxy$C_{1-6}$ alkyl" in the definition of $R^1$ in the formula (I) signifies $C_{1-6}$ alkyl substituted with $C_{1-6}$ alkoxy following the earlier given definition, of which specific examples include methoxymethyl, methoxyethyl, methoxy-n-propyl, methoxy-n-butyl, methoxy-n-hexyl, ethoxymethyl, isopropoxymethyl, ethoxyethyl and n-butoxy-n-propyl. Of those, methoxymethyl, methoxyethyl, ethoxymethyl and ethoxyethyl are preferred.

"Phenyl$C_{1-6}$ alkyl" in the definition of $R^2$ in the formula (I) signifies $C_{1-6}$ alkyl following its definition as given earlier, which is substituted with phenyl; and "carbamoyl$C_{1-6}$ alkyl", the $C_{1-6}$ alkyl following the earlier given definition, which is substituted with carbamoyl (—$CONH_2$); and "amino$C_{1-6}$ alkyl", the $C_{1-6}$ alkyl following the earlier given definition, which is substituted with amino (—$NH_2$).

"$C_{1-6}$ alkylamino$C_{1-6}$ alkyl" in the definition of $R^3$ in the formula (I) signifies the above amino$C_{1-6}$ alkyl whose amino group is further substituted with one of $C_{1-6}$ alkyl groups following the earlier given definition; and "di-($C_{1-6}$ alkyl) amino$C_{1-6}$ alkyl" signifies the same as above except that the amino group is substituted with two of the $C_{1-6}$ alkyl groups following the earlier given definition. Here the two $C_{1-6}$ alkyl substituting an amino group in di-($C_{1-6}$ alkyl)amino$C_{1-6}$ alkyl may be the same or different.

"$C_{1-6}$ alkylthio" in the definition of $R^3$ signifies thio (S) group substituted with the $C_{1-6}$ alkyl following the earlier given definition, and "$C_{1-6}$ alkoxycarbonyl" in the definition of Y in the formula (I) signifies carbonyl (CO) substituted with the $C_{1-6}$ alkoxy group following the earlier given definition.

"Aromatic carbocyclic group" in the definition of Y encompasses $C_{6-20}$ aromatic carbocyclic groups, of which specific examples include phenyl, 1-indenyl, 1-naphthyl, 2-naphthyl, 2-anthryl and 1-acenaphthenyl. Of those, phenyl and 1-naphthyl are preferred.

"Aromatic heterocyclic group" in the definition of Y encompasses monocyclic or polycyclic aromatic heterocyclic compounds containing 1 or 2 hetero atoms selected from N, O and S, of which one ring is 5- or 6-membered. Specific examples include pyrrolyl, furyl, thienyl, imidazolyl, pyrazolyl, oxazolyl, isoxazolyl, thiazolyl, pyridyl, pyrazinyl, pyrimidinyl, pyridazinyl, indolyl, benzimidazolyl, benzoxazolyl, benzthiazolyl, quinolyl, isoquinolyl and quinazolyl. Of those, monocyclic aromatic heterocyclic groups are preferred.

As "4-7-membered cycloalkenyl" in the definition of Y, for example, 1-cyclobutenyl, 1-cyclopentenyl, 1-cyclohexenyl, 1-cycloheptenyl, 2-cyclobutenyl, 2-cyclopentenyl and 3-cyclohexenyl can be named. Of those, 1-cyclohexenyl and 2-cyclohexenyl are preferred.

As "5-7-membered saturated heterocyclic group containing 1 or 2 nitrogen atoms" in the definition of Y, for example, pyrrolidinyl, piperidinyl, piperazinyl and azepinyl can be named. Of those, piperidinyl and piperazinyl are preferred.

As "5-7-membered saturated heterocyclic group forming a condensed ring with 5- or 6-membered saturated cyclic group and containing 1 or 2 nitrogen atoms" in the definition of Y, for example, hexahydrocyclopenta[b]pyrrolyl, hexahydrocyclopenta[c]pyrrolyl, octahydrocyclopenta[b]pyridyl, octahydrocyclopenta[b]pyridyl, decahydrocyclopenta[b]azepinyl, octahydroindolyl, octahydroisoindolyl, decahydroquinolyl, decahydroisoquinolyl, dodecahydrobenzo[b]azepinyl, octahydropyrrolo[2,3-d]pyridyl, octahydropyrrolo[1,2-a]pyrazyl, octahydropyrido[1,2-a]pyrimidinyl, decahydrophthalazinyl, decahydronaphthyridinyl and decahydroquinazolinyl can be named. Of those, decahydroquinolyl, decahydroisoquinolyl and octahydropyrrolo[1,2-a]pyrazyl are preferred.

The compound of the formula (I), in which $R^1$ is methyl, $R^2$ is hydrogen, $R^3$ is benzyl, Z is O and n is 0 (which is hereinafter referred to as "Compound A") has already been posted in the screening library of Ambinter Co., and therefore it is excluded from the compounds represented by the formula (I) of the present invention. In this screening library, however, utility of Compound A is neither described nor suggested.

Accordingly, the present invention also provides PDE9-inhibiting agents containing the compounds including thienopyrimidine derivatives represented by the formula (I)

as well as Compound A (hereafter they are collectively referred to as "compounds of formula (IA)") or salts thereof; pharmaceutical compositions comprising compounds of the formula (IA) or salts thereof and pharmaceutically acceptable carriers; and treating agents for overactive bladder syndrome, pollakiuria, urinary incontinence, dysuria in benign prostatic hyperplasia, neurogenic bladder, interstitial cystitis, urolithiasis, benign prostatic hyperplasia, erectile dysfunction, cognitive impairment, neuropathy, Alzheimer's disease, pulmonary hypertension, chronic obstructive pulmonary disease, ischemic heart disease, hypertension, angina, myocardial infarction, arteriosclerosis, thrombosis, embolism, type 1 diabetes, and type 2 diabetes, which are characterized by containing compounds of the formula (IA) or salts thereof as the active ingredient.

A group of compounds which are preferred for the present invention are those of the formula (I) in which $R^1$ stands for $C_{1-6}$ alkyl, in particular, methyl.

Another preferred group of compounds for the present invention are those of the formula (I) in which $R^2$ stands for hydrogen.

Still another preferred group of compounds for the present invention are those of the formula (I) in which $R^3$ stands for Y—X—group, in particular, the compounds of the formula (I) in which X stands for $CH_2$, S, O or NH, inter alia, $CH_2$.

Furthermore, where $R^3$ stands for Y—X— group, the compounds of the formula (I) in which Y stands for an aromatic carbocyclic group or aromatic heterocyclic group, which are optionally substituted with 1-3 substituents selected from halogen, $C_{1-6}$ alkyl, $C_{1-6}$ haloalkyl containing 1-6 halogen atoms, $C_{1-6}$ haloalkyloxy containing 1-6 halogen atoms, $C_{1-6}$ haloalkylthio containing 1-6 halogen atoms, $C_{1-6}$ alkoxy, $C_{1-6}$ alkylthio, $C_{1-4}$ alkylenedioxy, carboxyl, $C_{1-6}$ alkoxycarbonyl, amino, nitro and phenyl, are particularly preferred.

Another preferred group of compounds for the present invention are those of the formula (I) in which Z stands for O.

Still different group of compounds preferred for the present invention are those of the formula (I) in which n is 0.

Typical examples of the compounds of the formula (I) which are provided by the present invention include the following, besides those shown in the later appearing Examples:

2-benzyl-4-oxo-3,4-dihydrothieno[2,3-d]pyrimidine-6-carboxylic acid,
2-(5-chlorothiophen-2-ylmethyl)-4-oxo-3,4-dihydrothieno-[2,3-d]pyrimidine-6-carboxylic acid,
2-(2-fluorobenzyl)-4-oxo-3,4-dihydrothieno[2,3-d]pyrimidine-6-carboxylic acid,
2-(3-fluorobenzyl)-4-oxo-3,4-dihydrothieno[2,3-d]pyrimidine-6-carboxylic acid,
2-(4-fluorobenzyl)-4-oxo-3,4-dihydrothieno[2,3-d]pyrimidine-6-carboxylic acid,
2-(2-chlorobenzyl)-4-oxo-3,4-dihydrothieno[2,3-d]pyrimidine-6-carboxylic acid,
2-(4-chlorobenzyl)-4-oxo-3,4-dihydrothieno[2,3-d]pyrimidine-6-carboxylic acid,
2-(3-bromobenzyl)-4-oxo-3,4-dihydrothieno[2,3-d]pyrimidine-6-carboxylic acid,
2-(3-methylbenzyl)-4-oxo-3,4-dihydrothieno[2,3-d]pyrimidine-6-carboxylic acid,
4-oxo-2-(2-trifluoromethylbenzyl)-3,4-dihydrothieno-[2,3-d]pyrimidine-6-carboxylic acid,
2-(cyclohexen-1-ylmethyl)-4-oxo-3,4-dihydrothieno[2,3-d]-pyrimidine-6-carboxylic acid,
5-methyl-4-oxo-2-(thiophen-2-yl)-3,4-dihydrothieno-[2,3-d]pyrimidine-6-carboxylic acid,
2-(α-hydroxythiophen-2-ylmethyl)-5-methyl-4-oxo-3,4-dihydrothieno[2,3-d]pyrimidine-6-carboxylic acid,
5-methyl-4-oxo-2-[(2-thiophen-2-yl)ethyl]-3,4-dihydrothieno-[2,3-d]pyrimidine-6-carboxylic acid,
5-methyl-4-oxo-2-(thiophen-2-ylcarbonyl)-3,4-dihydrothieno-[2,3-d]pyrimidine-6-carboxylic acid,
5-methyl-4-oxo-2-(thiophen-2-ylsulfanyl)-3,4-dihydrothieno-[2,3-d]pyrimidine-6-carboxylic acid,
5-methyl-4-oxo-2-(thiophen-2-yloxy)-3,4-dihydrothieno[2,3-d]-pyrimidine-6-carboxylic acid,
5-methyl-4-oxo-2-(thiophen-2-ylamino)-3,4-dihydrothieno-[2,3-d]pyrimidine-6-carboxylic acid,
2-(5-fluorothiophen-2-ylmethyl)-5-methyl-4-oxo-3,4-dihydrothieno[2,3-d]pyrimidine-6-carboxylic acid,
2-(5-bromothiophen-2-ylmethyl)-5-methyl-4-oxo-3,4-dihydrothieno[2,3-d]pyrimidine-6-carboxylic acid,
5-methyl-2-(5-methylthiophen-2-ylmethyl)-4-oxo-3,4-dihydrothieno[2,3-d]pyrimidine-6-carboxylic acid,
2-(5-fluorothiophen-3-ylmethyl)-5-methyl-4-oxo-3,4-dihydrothieno[2,3-d]pyrimidine-6-carboxylic acid,
2-(5-chlorothiophen-3-ylmethyl)-5-methyl-4-oxo-3,4-dihydrothieno[2,3-d]pyrimidine-6-carboxylic acid,
2-(5-bromothiophen-3-ylmethyl)-5-methyl-4-oxo-3,4-dihydrothieno[2,3-d]pyrimidine-6-carboxylic acid,
5-methyl-2-(5-methylthiophen-3-ylmethyl)-4-oxo-3,4-dihydrothieno[2,3-d]pyrimidine-6-carboxylic acid,
2-(furan-2-ylmethyl)-5-methyl-4-oxo-3,4-dihydrothieno-[2,3-d]pyrimidine-6-carboxylic acid,
2-(furan-3-ylmethyl)-5-methyl-4-oxo-3,4-dihydrothieno-[2,3-d]pyrimidine-6-carboxylic acid,
2-(5-chlorofuran-2-ylmethyl)-5-methyl-4-oxo-3,4-dihydrothieno[2,3-d]pyrimidine-6-carboxylic acid,
2-(5-chlorofuran-3-ylmethyl)-5-methyl-4-oxo-3,4-dihydrothieno[2,3-d]pyrimidine-6-carboxylic acid,
2-(5-chlorooxazol-2-ylmethyl)-5-methyl-4-oxo-3,4-dihydrothieno[2,3-d]pyrimidine-6-carboxylic acid,
5-methyl-4-oxo-2-(pyridin-4-ylmethyl)-3,4-dihydrothieno[2,3-d]pyrimidine-6-carboxylic acid,
5-methyl-4-oxo-2-(pyrimidin-2-ylmethyl)-3,4-dihydrothieno[2,3-d]pyrimidine-6-carboxylic acid,
2-(4-methoxybenzyl)-5-methyl-4-oxo-3,4-dihydrothieno-[2,3-d]pyrimidine-6-carboxylic acid,
2-(3,5-dichlorobenzyl)-5-methyl-4-oxo-3,4-dihydrothieno-[2,3-d]pyrimidine-6-carboxylic acid,
2-(4-chloro-3-fluorobenzyl)-5-methyl-4-oxo-3,4-dihydrothieno-[2,3-d]pyrimidine-6-carboxylic acid,
2-(4-chloro-3-methylbenzyl)-5-methyl-4-oxo-3,4-dihydrothieno-[2,3-d]pyrimidine-6-carboxylic acid,
2-(4-chloro-3-trifluoromethylbenzyl)-5-methyl-4-oxo-3,4-dihydrothieno[2,3-d]pyrimidine-6-carboxylic acid,
2-(3-chloro-5-trifluoromethylbenzyl)-5-methyl-4-oxo-3,4-dihydrothieno[2,3-d]pyrimidine-6-carboxylic acid,
2-(3-carboxybenzyl)-5-methyl-4-oxo-3,4-dihydrothieno-[2,3-d]pyrimidine-6-carboxylic acid,
2-(3-ethoxycarbonylbenzyl)-5-methyl-4-oxo-3,4-dihydrothieno-[2,3-d]pyrimidine-6-carboxylic acid,
2-(3-aminobenzyl)-5-methyl-4-oxo-3,4-dihydrothieno[2,3-d]-pyrimidine-6-carboxylic acid,
5-methyl-2-(3-nitrobenzyl)-4-oxo-3,4-dihydrothieno-[2,3-d]pyrimidine-6-carboxylic acid,
3-amino-2-benzyl-5-methyl-4-oxo-3,4-dihydrothieno-[2,3-d]pyrimidine-6-carboxylic acid,
3-amino-5-methyl-4-oxo-2-(thiophen-2-ylmethyl)-3,4-dihydrothieno[2,3-d]pyrimidine-6-carboxylic acid,
3-amino-5-methyl-4-oxo-2-(thiophen-3-ylmethyl)-3,4-dihydrothieno[2,3-d]pyrimidine-6-carboxylic acid,
3-amino-2-(5-chlorothiophen-2-ylmethyl)-5-methyl-4-oxo-3,4-dihydrothieno[2,3-d]pyrimidine-6-carboxylic acid, 3-amino-2-(2-fluorobenzyl)-5-methyl-4-oxo-3,4-dihydrothieno-[2,3-d]pyrimidine-6-carboxylic acid,
3-amino-2-(3-fluorobenzyl)-5-methyl-4-oxo-3,4-dihydrothieno-[2,3-d]pyrimidine-6-carboxylic acid,
3-amino-2-(4-fluorobenzyl)-5-methyl-4-oxo-3,4-dihydrothieno-[2,3-d]pyrimidine-6-carboxylic acid,
3-amino-2-(2-chlorobenzyl)-5-methyl-4-oxo-3,4-dihydrothieno-[2,3-d]pyrimidine-6-carboxylic acid,
3-amino-2-(3-chlorobenzyl)-5-methyl-4-oxo-3,4-dihydrothieno-[2,3-d]pyrimidine-6-carboxylic acid,
3-amino-2-(4-chlorobenzyl)-5-methyl-4-oxo-3,4-dihydrothieno-[2,3-d]pyrimidine-6-carboxylic acid,
3-amino-2-(3,4-dichlorobenzyl)-5-methyl-4-oxo-3,4-dihydrothieno[2,3-d]pyrimidine-6-carboxylic acid,
3-amino-2-(3-bromobenzyl)-5-methyl-4-oxo-3,4-dihydrothieno-[2,3-d]pyrimidine-6-carboxylic acid,
3-amino-5-methyl-2-(3-methylbenzyl)-4-oxo-3,4-dihydrothieno[2,3-d]pyrimidine-6-carboxylic acid,
3-amino-5-methyl-4-oxo-2-(2-trifluoromethylbenzyl)-3,4-dihydrothieno[2,3-d]pyrimidine-6-carboxylic acid,
3-amino-5-methyl-4-oxo-2-(3-trifluoromethylbenzyl)-3,4-dihydrothieno[2,3-d]pyrimidine-6-carboxylic acid,
3-amino-2-(cyclopenten-1-ylmethyl)-5-methyl-4-oxo-3,4-dihydrothieno[2,3-d]pyrimidine-6-carboxylic acid,
3-amino-2-(cyclohexen-1-ylmethyl)-5-methyl-4-oxo-3,4-dihydrothieno[2,3-d]pyrimidine-6-carboxylic acid,
and the like.

The compounds of the formula (I) of this invention can also form salts, for example, alkali metal salts such as sodium salts, potassium salts, lithium salts and the like; alkaline earth metal salts such as calcium salts, magnesium salts and the like; salts with organobases such as triethylamine, dicyclohexylamine, pyrrolidine, morpholine, pyridine and the like; and ammonium salts. Depending on the kind(s) of substituent(s), they can also form salts with inorganic acids such as hydrochloric acid, hydrobromic acid, sulfuric acid, nitric acid, phosphoric acid and the like; or organic acids such as acetic acid, oxalic acid, citric acid, lactic acid, tartaric acid, p-toluenesulfonic acid and the like. Of these salts, particularly pharmaceutically acceptable salts are preferred.

According to the present invention, the compounds of the formula (I) in which Z stands for O can be prepared, for example, by either one of the methods (a)-(c) as described in the following, depending on the kind of $R^2$. Furthermore, the compounds of the formula (I) in which Z stands for O and $R^2$ and $R^3$ together form tetramethylene group can be prepared, for example, by the method (d) as described in the following. The compounds of the formula (I) in which Z stands for S can be prepared, for example, by the method (e) as described in the following.

Method (a): A compound of the formula (I) in which Z stands for O and $R^2$ stands for hydrogen, i.e., a thienopyrimidine derivative represented by the formula,

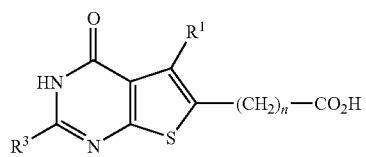

(I-1)

in the formula, $R^1$, $R^3$ and n have the previously defined significations, can be prepared by, for example, reacting a thiophene derivative of the formula,

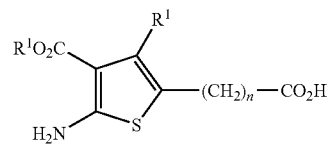

(II)

in the formula, $R^1$ and n have the previously defined significations, and

R and R' stand for, independently of each other, $C_{1-6}$ alkyl, with a nitrile compound represented by the formula, $$R^3-CN \qquad (III)$$

in the formula, $R^3$ has the previously given signification, to form a compound represented by the following formula,

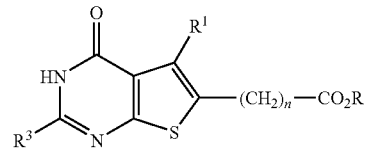

(IV)

in the formula, $R^1$, $R^3$, n and R have the previously defined significations, and successively hydrolyzing the ester in 6-substituent on the thienopyrimidine ring in the compound of above formula (IV).

Method (b): A compound of the formula (I) in which Z stands for O and $R^2$ stands for $C_{1-6}$ alkyl or phenyl$C_{1-6}$ alkyl, i.e., 3-alkylthienopyrimidine derivative represented by the formula,

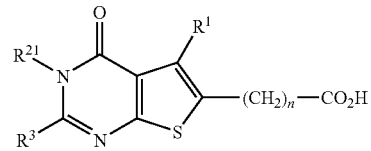

(I-2)

in the formula, $R^1$, $R^3$ and n have the previously defined significations, and $R^{21}$ stands for $C_{1-6}$ alkyl or phenyl$C_{1-6}$ alkyl, can be prepared by N-alkylating 3-nitrogen atom on the pyrimidine ring in a compound of above formula (IV) obtainable by the method (a), followed by ester hydrolysis similar to that in the method (a). When the compound of the formula (IV) has other substituent(s) liable to participate in the N-alkylation, for example, carboxyl, hydroxyl, amino other than the 3-nitrogen atom on the pyrimidine ring, it is advantageous to protect such group(s) with adequate protective group(s) in advance of the N-alkylation of 3-nitrogen atom on the pyrimidine ring and removing the protective group(s) after the end of the reaction.

Method (c): A compound of the formula (I) in which Z stands for O and R² stands for amino, i.e., 3-aminothienopyrimidine derivative of the formula,

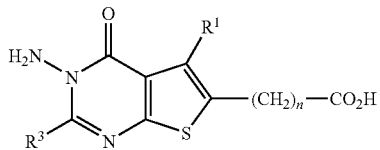
(I-3)

in the formula,

R¹, R³ and n have the previously defined significations, can be prepared, for example, by subjecting a compound of the formula,

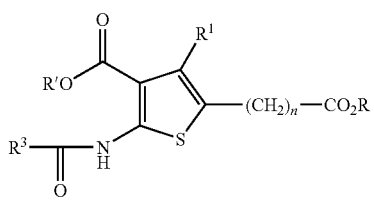
(V)

in the formula,

R¹, R³, n, R and R' have the previously defined significations, to ring closure reaction with hydrazine, and thereafter hydrolyzing the ester similarly to the method (a).

Method (d): A compound of the formula (I) in which Z stands for O and R² and R³ together form tetramethylene, i.e., a compound of the following formula,

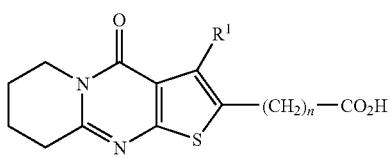
(I-4)

in the formula,

R¹ and n have the previously defined significations, can be prepared, for example, by reacting a compound of the formula (II) with a compound of the formula,

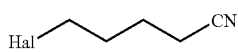
(VI)

in the formula,

Hal stands for halogen, and subjecting the resulting compound of the formula,

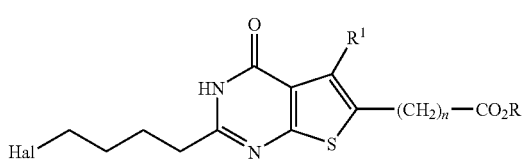
(VII)

in the formula,

R¹, n, R and Hal have the previously defined significations, to ring closure reaction, to lead it to a compound of the following formula,

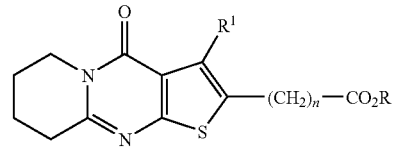
(VIII)

in the formula,

R¹, n and R have the previously defined significations, and thereafter hydrolyzing the ester similarly to the method (a).

Method (e): A compound of the formula (I) in which Z stands for S, i.e., a thienopyrimidine derivative of the following formula,

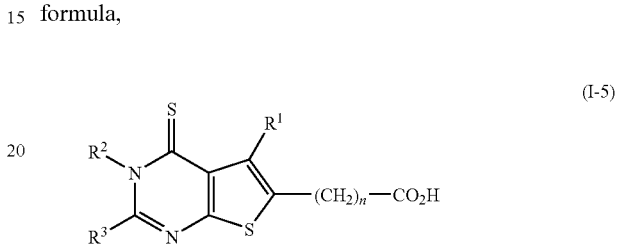
(I-5)

in the formula,

R¹, R², R³ and n have the previously defined significations, can be prepared by treating a compound of the following formula,

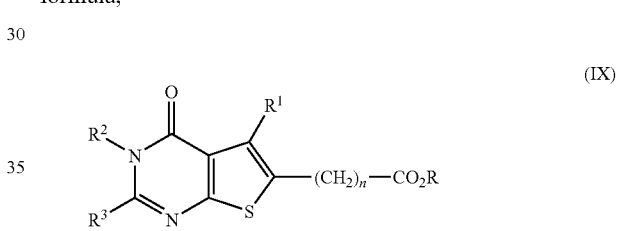
(IX)

in the formula,

R¹, R², R³, n and R have the previously defined significations, with Lawesson's reagent to lead it to a compound of the following formula,

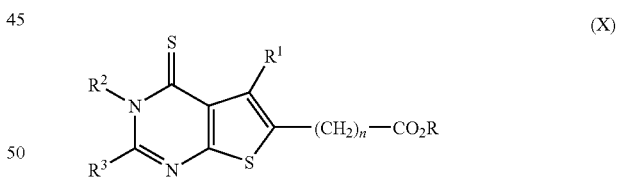
(X)

in the formula,

R¹, R², R³, n and R have the previously defined significations, and thereafter hydrolyzing the ester similarly to the method (a).

The reaction of a compound of the formula (II) with a nitrile compound of the formula (III) in the above method (a) can be performed generally in an inert solvent such as amides including N,N-dimethylformamide and N,N-dimethylacetamide; alcohols including methanol, ethanol and isopropanol; or ethers including tetrahydrofuran and dioxane, in the presence of an acid catalyst such as hydrochloric acid, hydrobromic acid and p-toluenesulfonic acid, at −20° C. to the refluxing temperature of the reaction mixture, preferably 0-50° C.

The use ratio of the nitrile compound of the formula (III) to the compound of the formula (II) is not particularly limited, while it is preferable to use generally at least 1 mol, in particular, within a range of 1.05-5 mols, inter alia, 1.2-2 mols, of the nitrile compound of the formula (III), per mol of the compound of the formula (II). The acid catalyst can be used within a range of about 0.2-about 50 mols, per mol of the compound of the formula (II).

The hydrolysis of the ester at the 6-substituent on thionopyrimidine ring in the resulting compound of the formula (IV) can follow any method heretofore known per se, for example, by suspending or dissolving the compound of the formula (IV) in a mixed solvent of alcohol such as methanol, ethanol or the like with water, at temperatures within a range of 0° C.—refluxing temperature of the reaction mixture, preferably from room temperature to refluxing temperature of the reaction mixture, in the presence of alkali such as sodium hydroxide, potassium hydroxide, potassium carbonate or the like. The use ratio of the alkali to the compound of the formula (IV) is not critical, but the alkali can be generally used within a range of about 1-20 mols per mol of the compound of the formula (IV).

The N-alkylation reaction of the compound of the formula (IV) in the above method (b) can be performed, for example, by nucleophilic substitution reaction using alkyl halide ($R^{21}$-Hal, wherein $R^{21}$ and Hal have the previously defined significations). The reaction is generally conducted in an inert organic solvent such as amides including N,N-dimethylformamide and N,N-dimethylacetamide; alcohols including methanol, ethanol and isopropanol, ethers such as tetrahydrofuran and dioxane; organic bases including pyridine; acetonitrile, or the like, in the optional presence of alkali such as sodium hydride, sodium methoxide, potassium butoxide, potassium hydroxide, potassium carbonate or the like; or organic base such as triethylamine, 2,6-di-tert-butyl-4-methylpyridine or the like, at temperatures ranging 0° C. to refluxing temperature of the reaction mixture, preferably room temperature to refluxing temperature of the reaction mixture.

The use ratio of alkyl halide used for N-alkylation of the compound of the formula (IV), to the same compound is not critical, while it is generally at least 1 mol, preferably 1.1-20 mols, inter alia, 1.2-10 mols, per mol of the compound of the formula (IV). Also the alkali or organic base can be normally used within a range of 1.1-about 20 mols per mol of the compound of the formula (IV).

The ring closure reaction of the compound of the formula (V) with hydrazine in the method (c) can be generally performed in an inert organic solvent such as amides including N,N-dimethylformamide and N,N-dimethylacetamide; alcohols including methanol, ethanol and isopropanol; ethers including tetrahydrofuran and dioxane; at temperatures within a range of 0° C. to the refluxing temperature of the reaction mixture, preferably room temperature to the refluxing temperature of the reaction mixture.

The use ratio of hydrazine to the compound of the formula (V) is not critical, while hydrazine can be used within a range of at least 1 mol, preferably 1.2-10 mols, inter alia, 1.3-5 mols, per mol of the compound of the formula (V).

The reaction of a compound of the formula (II) with a halogenated nitrile compound of the formula (VI) in the method (d) can be performed by a method similar to the reaction of a compound of the formula (II) with a nitrile compound of the formula (III) in the method (a).

The ring closure reaction of the compound of the formula (VII) in the method (d) can be performed by a method similar to the N-alkylation of the compound of the formula (IV) in the method (b).

The treating reaction of the compound of the formula (IX) with Lawesson's reagent in the method (e) can be performed generally in an inert organic solvent, for example, ethers including tetrahydrofuran and dioxane; or aromatic hydrocarbons including benzene and toluene; at temperatures ranging from 0° C. to the refluxing temperature of the reaction mixture, preferably room temperature to the refluxing temperature of the reaction mixture.

The use ratio of Lawesson's reagent to the compound of the formula (IX) is not particularly limited, while generally it can be at least 0.5 mol, preferably 0.5-5 mols, inter alia, 0.6-2 mols, per mol of the compound of the formula (IX).

Most of the thiophene derivatives of the formula (II) which are used as starting materials in the reactions of above methods (a) and (d) are novel compounds never disclosed in known literature, but they can be readily synthesized by methods similar to those for syntheses of known thiophene derivatives, for example, following the route as shown in the following reaction scheme 1. For the particulars such as the reaction conditions, refer to later appearing Production Example 1.

Reaction scheme 1

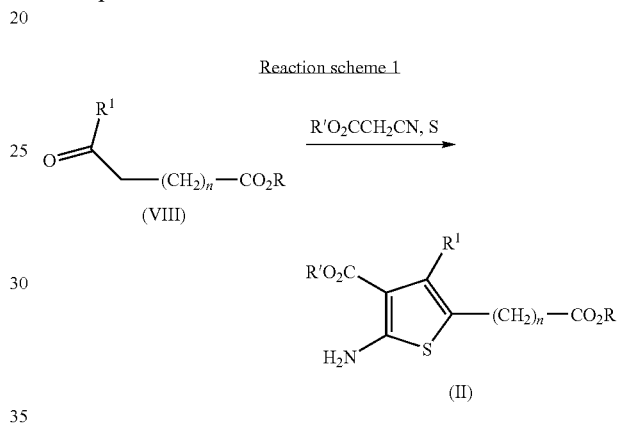

in the above formulae, $R^1$, n, R and R' have the previously defined significations.

Also nearly all of the nitrile compounds of the formula (III) which are used as the starting materials in the reaction of above method (a) are known. Even those unknown can be readily synthesized following known methods of synthesis, for example, following the methods disclosed in Referential Literature, SYNTHESIS, 1980, 150-151 or Bioorg. Med. Chem. Lett., 2002 (12) 1275-1278.

Furthermore, the compounds of the formula (V) which are used as the starting materials in the method (c) can be synthesized, for example, by amidation of the compounds of the formula (II) with carboxylic acid compounds of the formula, $$R^3—COOH \quad\quad\quad (IX)$$

in which $R^3$ has the previously defined signification, or reactive derivatives thereof (e.g., acid halide, acid anhydride, mixed acid anhydride, active amide, active ester and the like).

Those compounds of the formula (I) of the present invention produced in the reaction mixtures of above-described methods (a)-(d) can be isolated from the reaction mixtures and purified by the means known per se, for example, recrystallization, column chromatography, thin layer chromatography and the like.

Those thienopyrimidine derivatives represented by the formula (I) or salts thereof provided by the present invention and also Compound A and salts thereof exhibit potent PDE9-inhibiting activity, and are useful for curative and treating agents of diseases associated with degradation of cGMP by PDE9, for example, overactive bladder syndrome, pollakiuria, urinary incontinence, dysuria in benign prostatic hyperplasia, neurogenic bladder, interstitial cystitis, urolithiasis, benign prostatic hyperplasia, erectile dysfunction, cognitive impairment, neuropathy, Alzheimer's disease, pulmonary hypertension, chronic obstructive pulmonary disease, ischemic heart disease, hypertension, angina, myocardial infarction, arteriosclerosis, thrombosis, embolism, type 1 diabetes, and type 2 diabetes.

Among the thienopyrimidine derivatives represented by the formula (I) and salts thereof that are provided by the present invention and Compound A and salts thereof, those which exhibit slight PDE5-inhibiting activity in addition to their PDE9-inhibiting activity are expected to achieve also the functional effects based on the PDE5-inhibiting activity.

PDE9-inhibiting activity, PDE5-inhibiting activity and improving action on pathological models of dysuria exhibited by the compounds of the formula (I), Compound A and their salts are demonstrated by the following experiments.

(1) Measurement of PDE9-Inhibiting Activity:

1) Preparation of Human Recombinant PDE9 Protein

Based on the base sequence of hsPDE9A1 registered with GenBank database (accession No.: AF048837), hsPDE9A1 fragment was amplified by polymerase chain reaction under the following conditions, using the following sequence (Amasham Pharmacia Biotech) as the primer and Human Prostate MATCHMAKER cDNA library (CLONTECH) as the template DNA, with Pfu Turbo DNA polymerase (STRATAGENE):

```
hPDE9-5A primer:
                                           [SEQ ID NO: 1]
CTAGCTAGCCACCATGGGATCCGGCTCCTCC hPDE9-3A primer:
                                           [SEQ ID NO: 2]
TTTTCCTTTTGCGGCCGCTTATTAGGCACAGTCTCCTTCACTG
```

PCR condition: [95° C., 5 min]×1 cycle, [(95° C., 1 min), (58° C., 2 min), (72° C., 3 min)]×25 cycle, [72° C., 10 min]×1 cycle Thus obtained hsPDE9A1 fragment was given a restricted enzymatic treatment with NheI and NotI, and thereafter inserted into pcDNA 3.1(+) expression vector (Invitrogen) to let it serve as a human PDE9 expression vector.

Human PDE9 expression vector-transformed *Escherichia coli* was mass incubated to produce a large amount of PDE9 expression vector, which was transiently transfected into COS-1 cells, with LIPOFECTAMINE 2000 Reagent (GIBCO). The cells were homogenized in ice-cooled buffer A (40 mmol/L Tris-HCl, pH7.5, 15 mmol/L benzamidine; 15 mmol/L 2-mercaptoethanol; 1 μg/mL Pepstatin A, 1 μg/mL Leupeptin, 5 mmol/L EDTA) and centrifuged at 4° C., 14,000×g for 10 minutes. The supernatant was isolated to provide human recombinant PDE9 protein solution.

2) Measurement of PDE9-Inhibiting Activity

To 150 μL of buffer B (70 mmol/L Tris-HCl, pH7.5; 16.7 mmol/L $MgCl_2$, 33.3 nmol/L [$^3$H]-cGMP) solution containing [$^3$H]-cGMP (specific activity=244.2 GBq/mmol) at a concentration of 33.3 nmol/L, 50 μL of a solution of the compound to be evaluated (formed by dissolving the compound in DMSO and diluting it with distilled water to DMSO concentration of 5%) and 50 μL of the PDE9 protein solution as prepared in the above, as diluted with buffer C (40 mmol/L Tris-HCl, pH7.5, 15 mmol/L benzamidine, 15 mmol/L 2-mercaptoethanol, 1 μg/mL Pepstatin A, 1 μg/mL Leupeptin) by 1,500×, were added under cooling with ice. This mixed solution was incubated at 30° C. for 30 minutes and the enzymatic reaction of PDE9 was terminated by heating the system in boiling water for 90 seconds. Returning the system to room temperature, 50 μL of Snake venom (SIGMA: 1 mg/mL) was added, followed by 10 minutes' incubation at 30° C., to convert the [$^3$H]-5'-GMP produced in the previous reaction to [$^3$H]-guanosine. This reaction solution was passed through a column filled with 1 mL of 0.5 mol/L hydrochloric acid-activated cation-exchange resin (Bio-Rad AG50W-X4 resin, mesh size 200-400) and removed of the unreacted substrate ([$^3$H]-cGMP) by elution with 12 mL of distilled water. Thereafter [$^3$H]-guanosine was eluted with 3 mL of 3 mol/L aqueous ammonia and its radiation activity was measured with liquid scintillation counter.

PDE9 inhibition of the tested compound can be calculated by the following formula:

$$\left[\left(1 - \frac{\text{radiation activity where test compound is used}}{\text{radiation activity in control test}}\right)\right] \times 100$$

From the inhibition ratios at various concentration levels of each tested compound, its $IC_{50}$ value against PDE9 was determined. The results are shown in Table A given later.

(2) Measurement of PDE5-Inhibiting Activity:

1) Preparation of Human Recombinant PDE5 Protein

Based on the base sequence of hsPDE5A1 registered with GenBank database (accession No.: NM_001083), hsPDE5A1 fragment was amplified by polymerase chain reaction under the following conditions, using the following sequence (SIGMA GENOSYS) as the primer and Human Prostate MATCHMAKER cDNA library (CLONTECH) as the template DNA, with KDD plus DNA polymerase (TOYOBO):

```
hPDE5-5' E primer:
                                           [SEQ ID NO: 3]
CGGAATTCCAACCATGGAGCGGGC hPDE5-3' primer:
                                           [SEQ ID NO: 4]
GCTCTAGATCAGTTCCGCTTGGCCTGG
```

PCR condition: [94° C., 2 min]×1 cycle, [(94° C., 30 sec), (65° C., 30 sec), (68° C. 3 min)]×25 cycle, [68° C., 6 min]×1 cycle Thus obtained hsPDE5A1 fragment was given a restricted enzymatic treatment with XBaI and EcoRI, and thereafter inserted into pcDNA 3.1(+) expression vector (Invitrogen) to let it serve as a human PDE5 expression vector.

Human PDE5 expression vector-transformed *Escherichia coli* was mass incubated to produce a large amount of PDE5 expression vector, which was transiently transfected into COS-1 cells, with LIPOFECTAMINE 2000 Reagent (GIBCO). The cells were homogenized in ice-cooled buffer A and centrifuged at 4° C., 14,000×g for 10 minutes. The supernatant was isolated to provide human recombinant PDE5 protein solution.

2) Measurement of PDE5-Inhibiting Activity

By a method similar to the measurement of PDE9-inhibiting activity, PDE5-inhibiting activity of the test compounds was measured, their inhibition was calculated and $IC_{50}$ value to PDE5 of each of the compounds was determined. The results are shown in the following Table A, concurrently with the compounds' $IC_{50}$ values against PDE9.

TABLE A

| Compound | Structural Formula | Inhibitory Activity (IC$_{50}$ value: nmol/L) | |
| --- | --- | --- | --- |
| | | PDE9 | PDE5 |
| Example 1 | | 22 | 17,784 |
| Example 2 | | 40 | 21,116 |
| Example 3 | | 34 | 6,897 |
| Example 10 | | 30 | 6,767 |
| Example 12 | | 24 | 4,430 |
| Example 22 | | 34 | 22,159 |
| Example 36 | | 38 | 915 |
| Example 40 | | 46 | 20,008 |

TABLE A-continued

| Compound | Structural Formula | Inhibitory Activity (IC$_{50}$ value: nmol/L) | |
|---|---|---|---|
| | | PDE9 | PDE5 |
| Example 49 | | 44 | 18,903 |
| Example 52 | | 38 | 3,417 |
| Example 53 | | 22 | 5,712 |
| Example 57 | | 42 | 19,834 |
| Example 65 | | 28 | 8,591 |
| Example 66 | | 54 | 1,638 |
| Example 101 | | 14 | 34,879 |
| Example 102 | | 15 | 41,232 |

TABLE A-continued

| Compound | Structural Formula | Inhibitory Activity (IC$_{50}$ value: nmol/L) | |
|---|---|---|---|
| | | PDE9 | PDE5 |
| Example 103 | (2-benzyl-4-oxo-3H-thieno[2,3-d]pyrimidine-6-carboxylic acid) | 19 | 34,389 |
| Example 104 | (2-(3-chlorobenzyl)-4-oxo-3H-thieno[2,3-d]pyrimidine-6-carboxylic acid) | 10 | 15,819 |
| Example 105 | (2-(3-trifluoromethylbenzyl)-4-oxo-3H-thieno[2,3-d]pyrimidine-6-carboxylic acid) | 15 | 30,222 |
| Example 106 | (2-(3,4-dichlorobenzyl)-4-oxo-3H-thieno[2,3-d]pyrimidine-6-carboxylic acid) | 9 | 2,282 |
| Example 107 | (2-(cyclopentenylmethyl)-4-oxo-3H-thieno[2,3-d]pyrimidine-6-carboxylic acid) | 22 | 12,065 |
| Example 108 | (5-methyl-2-(thiophen-3-ylmethyl)-4-thioxo-3H-thieno[2,3-d]pyrimidine-6-carboxylic acid) | 9 | 1,636 |
| Example 109 | (5-methyl-2-(thiophen-2-ylmethyl)-4-thioxo-3H-thieno[2,3-d]pyrimidine-6-carboxylic acid) | 31 | 1,541 |
| Example 110 | (2-benzyl-5-methyl-4-thioxo-3H-thieno[2,3-d]pyrimidine-6-carboxylic acid) | 13 | 642 |
| Example 111 | (2-(3-bromobenzyl)-5-methyl-4-thioxo-3H-thieno[2,3-d]pyrimidine-6-carboxylic acid) | 11 | 712 |

TABLE A-continued

| Compound | Structural Formula | Inhibitory Activity (IC$_{50}$ value: nmol/L) | |
|---|---|---|---|
| | | PDE9 | PDE5 |
| Example 112 | | 5 | 1,112 |
| Example 113 | | 6 | 3,507 |
| Example 114 | | 4 | 73 |
| Example 115 | | 7 | 495 |
| Example 116 | | 48 | 70 |
| Example 117 | | 24 | 843 |
| Example 118 | | 11 | 8,874 |
| Example 119 | | 5 | 721 |
| Compound A | | 35 | 10,045 |

(3) Investigation of PDE9 Inhibitory Activity on Dysuria Pathological Model

Three to four weeks old female Hartley strain guinea pigs (Nippon SLC) were laparotomized under anesthesia with pentobarbital (30 mg/kg i.p.), and a polyethylene tube of 1.4 mm in width and 2.0 mm in inner diameter was placed in each guinea pig's urethra to the distal side by 1-2 mm from the bladder neck. After closing the incision, the guinea pigs were reared for at least 3 weeks to provide a model of urethral obstruction with the guinea pigs in which rise in intravesical pressure not accompanied by voiding (non-voiding contraction) and residual urine were induced.

The model was catheterized under anesthesia with urethane (1 g/kg i.p.) at the apex of urinary bladder and right jugular vein for cystometrography and intravenous administration, respectively. The other end of the bladder catheter was connected to a pressure transducer and infusion pump through three way stopcock. By means of the infusion pump, physiological saline was continuously infused into the bladder at a rate of 0.4 mL/min to induce micturition reflex. Immediately after the micturition reflex was induced, the physiological saline infusion into the bladder was stopped. The intravesical pressure at the time the micturition occurred was measured with the pressure transducer and the cystometrogram was recorded with pen recorder. The urine voided was collected with a disposable type weighing dish to measure its weight. Further the physiological saline remained in the bladder was sucked with syringe through the bladder catheter to measure the residual urine volume. Multiple operation cycles (normally 4 times) of suspending physiological saline infusion when micturition reflex was induced and resuming the infusion after about 1 minute to induce next micturition reflex, were repeated to stabilize the voiding response.

Thereafter either the compound solutions (solution of the compound in distilled water at a concentration of 3 mg/mL was diluted with physiological saline to 1, 0.3 or 0.1 mg/mL) or physiological saline, of a volume 10 mL/kg, was intravenously administered to the model over 4 minutes, during which the above cyclic operations were repeated from the initiation of the administration to 30 minutes after the administration, to measure the intravesical pressure, voided urine volume and residual urine volume. Also the frequency of non-voiding contraction occurred during the operations was measured. The respective mean values of frequency of non-voiding contraction and residual urine volume in the experiment using several guinea pigs are shown in the following Table B.

TABLE B

| Compound | Dose (i.v., mg/kg) | Frequency of non-voiding contraction (count/min) | | | Residual urine volume (mL) | | |
|---|---|---|---|---|---|---|---|
| | | pre-administration | post-administraton | quantitative change | pre-administration | post-administraton | quantitative change |
| Physiological saline | — | 1.10 | 1.08 | −0.02 | 1.44 | 1.43 | −0.01 |
| Example 2 | 1 | 0.91 | 0.47 | −0.44 | 1.27 | 1.23 | −0.04 |
| | 10 | 0.91 | 0.78 | −0.13 | 1.27 | 1.02 | −0.25 |
| Example 10 | 0.3 | 1.16 | 0.80 | −0.36 | 0.95 | 1.08 | +0.13 |
| | 3 | 1.16 | 0.49 | −0.67 | 0.95 | 1.11 | +0.16 |
| | 10 | 1.16 | 0.60 | −0.56 | 0.95 | 0.95 | 0.00 |
| Example 36 | 1 | 0.96 | 0.79 | −0.17 | 0.82 | 0.86 | +0.04 |
| | 3 | 1.16 | 0.77 | −0.39 | 1.33 | 1.03 | −0.30 |
| | 10 | 1.11 | 0.64 | −0.47 | 1.06 | 0.64 | −0.42 |
| Example 104 | 0.3 | 1.08 | 0.55 | −0.53 | 1.54 | 1.02 | −0.52 |
| | 3 | 1.44 | 0.78 | −0.66 | 1.37 | 0.88 | −0.49 |
| | 10 | 1.57 | 0.83 | −0.74 | 1.68 | 0.62 | −1.06 |
| Example 112 | 0.3 | 1.12 | 1.02 | −0.10 | 1.02 | 0.91 | −0.11 |
| | 3 | 1.12 | 0.76 | −0.36 | 1.02 | 0.27 | −0.75 |
| | 10 | 1.12 | 0.59 | −0.53 | 1.02 | 0.48 | −0.54 |

As shown in above Table B, compounds of the present invention also exhibit significant residual urine-reducing action.

Thus the thienopyrimidine derivatives represented by the formula (I) of the present invention and Compound A, or their salts can be administered as PDE9 inhibitor or PDE9 inhibitor concurrently exhibiting slight PDE5 inhibitory activity, for therapy or treatment of PDE9-associated diseases of human and other mammals, orally or parenterally (e.g., intramuscular injection, intravenous injection, rectal administration, percutaneous administration and the like).

The drugs of the present invention can be formulated, together with non-toxic excipients, any preparation forms such as solid (e.g., tablet, hard capsule, soft capsule, granule, powder, fine granule, pill, troche and the like); semi-solid (e.g., suppository, ointment and the like); or liquid (e.g., injection, emulsion, suspension, lotion, spray and the like). As non-toxic excipients useful for such formulation, for example, starch, gelatin, glucose, lactose, fructose, maltose, magnesium carbonate, talc, magnesium stearate, methyl cellulose, carboxymethyl cellulose or salts thereof, gum Arabic, polyethylene glycol, p-hydroxybenzoic acid alkyl ester, syrup, ethanol, propylene glycol, vaseline, Carbowax, glycerine, sodium chloride, sodium sulfite, sodium phosphate, citric acid and the like can be named. These formulations may also contain other therapeutically useful drugs.

Content of a compound of the formula (IA) in these formulations differs depending on the preparation form and administration route, while generally it can be present at a concentration of 0.1-50 wt % in solid and semi-solid forms, and of 0.05-10 wt %, in liquid form.

Dosage of a compound of the formula (IA) is variable over a broad range according to the kind of warm-blooded animals including human to be treated, kind of involved disease, administration route, seriousness of symptoms, doctor's diagnosis and the like. Whereas, generally it can be within a range of 0.01-5 mg/kg per day, preferably 0.02-2 mg/kg per day, it being obviously possible to administer doses less than

EXAMPLES

Hereinafter the present invention is explained in further details, referring to Examples, Production Examples and Formulation Examples, it being understood that the invention is not limited to those Examples.

Production Example 1

Ethyl 5-methyl-4-oxo-2-(thiophen-3-ylmethyl)-3,4-dihydrothieno[2,3-d]pyrimidine-6-carboxylate 515 Milligrams of diethyl 5-amino-3-methylthiophene-2,4-dicarboxylate and 296 mg of 3-thiopheneacetonitrile were added to 8 mL of 4N hydrogen chloride-dioxane solution and stirred for 10 hours. Thereafter the liquid reaction mixture was poured on ice, and its pH was adjusted to 8-9 with 25% aqueous ammonia. Whereupon precipitated crystals were recovered by filtration and washed first with water, and then with hexane. The crude crystals were recrystallized from a liquid mixture of N,N-dimethylformamide and cyclohexane, to provide 397 mg of the title compound.

$^1$H-NMR (DMSO-$d_6$) δ: 1.30 (3H, t, J=7.1 Hz), 2.81 (3H, s), 3.97 (2H, s), 4.30 (2H, q, J=7.1 Hz), 7.0-7.6 (3H, m), 12.74 (1H, br s)

MS (m/z): 334 (M$^+$)

Compounds of Production Examples 2-20 were prepared in the manner similar to the Production Example 1.

Production Example 2

Ethyl 5-methyl-4-oxo-2-(thiophen-2-ylmethyl)-3,4-dihydrothieno[2,3-d]pyrimidine-6-carboxylate $^1$H-NMR (DMSO-$d_6$) δ: 1.30 (3H, t, J=7.1 Hz), 2.81 (3H, s), 4.17 (2H, s), 4.30 (2H, q, J=7.1 Hz), 6.9-7.5 (3H, m), 12.80 (1H, br s)

MS (m/z): 334 (M$^+$)

Production Example 3

Ethyl 2-(5-chlorothiopen-2-ylmethyl)-5-methyl-4-oxo-3,4-dihydrothieno[2,3-d]pyrimidine-6-carboxylate $^1$H-NMR (DMSO-$d_6$) δ: 1.30 (3H, t, J=6.9 Hz), 2.81 (3H, s), 4.14 (2H, s), 4.30 (2H, q, J=7.1 Hz), 6.91 (1H, d, J=3.9 Hz), 6.98 (1H, d, J=3.9 Hz), 12.79 (1H, br s)

MS (m/z): 370 (M$^+$+2), 368 (M$^+$)

Production Example 4

Ethyl 5-methyl-2-(4-methylthiazol-2-ylmethyl)-4-oxo-3,4-dihydrothieno[2,3-d]pyrimidine-6-carboxylate $^1$H-NMR (DMSO-$d_6$) δ: 1.30 (3H, t, J=7.1 Hz), 2.32 (3H, d, J=0.8 Hz), 2.82 (3H, s), 4.30 (2H, q, J=7.1 Hz), 4.37 (2H, s), 7.21 (1H, d, J=0.8 Hz), 12.85 (1H, br s)

MS (m/z): 349 (M$^+$)

Production Example 5

Ethyl 2-(2-fluorobenzyl)-5-methyl-4-oxo-3,4-dihydrothieno-[2,3-d]pyrimidine-6-carboxylate $^1$H-NMR (DMSO-$d_6$) δ: 1.29 (3H, t, J=7.1 Hz), 2.82 (3H, s), 4.05 (2H, s), 4.29 (2H, q, J=7.2 Hz), 7.1-7.5 (4H, m), 12.80 (1H, br s)

MS (m/z): 346 (M$^+$)

Production Example 6

Ethyl 2-(3-fluorobenzyl)-5-methyl-4-oxo-3,4-dihydrothieno-[2,3-d]pyrimidine-6-carboxylate $^1$H-NMR (DMSO-$d_6$) δ: 1.30 (3H, t, J=7.1 Hz), 2.81 (3H, s), 3.99 (2H, s), 4.29 (2H, q, J=7.1 Hz), 7.0-7.5 (4H, m), 12.77 (1H, br s)

MS (m/z): 346 (M$^+$)

Production Example 7

Ethyl 2-(3-chlorobenzyl)-5-methyl-4-oxo-3,4-dihydrothieno-[2,3-d]pyrimidine-6-carboxylate $^1$H-NMR (DMSO-$d_6$) δ: 1.30 (3H, t, J=7.1 Hz), 2.81 (3H, s), 3.98 (2H, s), 4.29 (2H, q, J=7.1 Hz), 7.2-7.4 (3H, m), 7.45 (1H, s), 12.77 (1H, br s)

MS (m/z): 364 (M$^+$+2), 362 (M$^+$)

Production Example 8

Ethyl 2-(2,3-dichlorobenzyl)-5-methyl-4-oxo-3,4-dihydrothieno[2,3-d]pyrimidine-6-carboxylate $^1$H-NMR (DMSO-$d_6$) δ: 1.29 (3H, t, J=6.9 Hz), 2.83 (3H, s), 4.21 (2H, s), 4.29 (2H, q, J=7.2 Hz), 7.3-7.7 (3H, m), 12.81 (1H, br s)

MS (m/z): 398 (M$^+$+2), 396 (M$^+$)

Production Example 9

Ethyl 2-(2,4-dichlorobenzyl)-5-methyl-4-oxo-3,4-dihydrothieno[2,3-d]pyrimidine-6-carboxylate $^1$H-NMR (DMSO-$d_6$) δ: 1.29 (3H, t, J=7.1 Hz), 2.82 (3H, s), 4.14 (2H, s), 4.29 (2H, q, J=7.2 Hz), 7.3-7.7 (3H, m), 12.82 (1H, br s)

MS (m/z): 398 (M$^+$+2), 396 (M$^+$)

Production Example 10

Ethyl 2-(3,4-dichlorobenzyl)-5-methyl-4-oxo-3,4-dihydrothieno[2,3-d]pyrimidine-6-carboxylate $^1$H-NMR (DMSO-$d_6$) δ: 1.29 (3H, t, J=7.0 Hz), 2.81 (3H, s), 4.00 (2H, s), 4.29 (2H, q, J=7.2 Hz), 7.3-7.7 (3H, m), 12.77 (1H, br s)

MS (m/z): 398 (M$^+$+2), 396 (M$^+$)

Production Example 11

Ethyl 2-(3-bromobenzyl)-5-methyl-4-oxo-3,4-dihydrothieno-[2,3-d]pyrimidine-6-carboxylate $^1$H-NMR (DMSO-$d_6$) δ: 1.30 (3H, t, J=6.9 Hz), 2.81 (3H, s), 3.98 (2H, s), 4.29 (2H, q, J=7.1 Hz), 7.2-7.7 (4H, m), 12.76 (1H, br s)

MS (m/z): 408 (M$^+$+2), 406 (M$^+$)

Production Example 12

Ethyl 2-(4-bromobenzyl)-5-methyl-4-oxo-3,4-dihydrothieno-[2,3-d]pyrimidine-6-carboxylate $^1$H-NMR (DMSO-$d_6$) δ: 1.30 (3H, t, J=7.1 Hz), 2.80 (3H, s), 3.95 (2H, s), 4.29 (2H, q, J=7.1 Hz), 7.2-7.6 (4H, m), 12.76 (1H, br s)
MS (m/z): 408 (M$^+$+2), 406 (M$^+$)

Production Example 13

Ethyl 5-methyl-2-(3-methylbenzyl)-4-oxo-3,4-dihydrothieno-[2,3-d]pyrimidine-6-carboxylate $^1$H-NMR (DMSO-$d_6$) δ: 1.30 (3H, t, J=7.1 Hz), 2.28 (3H, s), 2.80 (3H, s), 3.91 (2H, s), 4.29 (2H, q, J=7.1 Hz), 7.0-7.3 (4H, m), 12.75 (1H, br s)
MS (m/z): 342 (M$^+$)

Production Example 14

Ethyl 5-methyl-2-(4-methylbenzyl)-4-oxo-3,4-dihydrothieno-[2,3-d]pyrimidine-6-carboxylate $^1$H-NMR (DMSO-$d_6$) δ: 1.30 (3H, t, J=6.9 Hz), 2.26 (3H, s), 2.80 (3H, s), 3.90 (2H, s), 4.29 (2H, q, J=7.2 Hz), 7.13, 7.23 (4H, AB, J=7.7 Hz), 12.74 (1H, br s)
MS (m/z): 342 (M$^+$)

Production Example 15

Ethyl 5-methyl-4-oxo-2-(2-trifluoromethylbenzyl)-3,4-dihydrothieno[2,3-d]pyrimidine-6-carboxylate $^1$H-NMR (DMSO-$d_6$) δ: 1.28 (3H, t, J=6.9 Hz), 2.82 (3H, s), 4.24 (2H, s), 4.28 (2H, q, J=7.2 Hz), 7.4-7.8 (4H, m), 12.83 (1H, br s)
MS (m/z): 396 (M$^+$)

Production Example 16

Ethyl 5-methyl-4-oxo-2-(3-trifluoromethylbenzyl)-3,4-dihydrothieno[2,3-d]pyrimidine-6-carboxylate $^1$H-NMR (DMSO-$d_6$) δ: 1.29 (3H, t, J=6.9 Hz), 2.81 (3H, s), 4.09 (2H, s), 4.29 (2H, q, J=7.2 Hz), 7.5-7.7 (3H, m), 7.76 (1H, s), 12.80 (1H, br s)
MS (m/z): 396 (M$^+$)

Production Example 17

Ethyl 5-methyl-4-oxo-2-(4-trifluoromethylbenzyl)-3,4-dihydrothieno[2,3-d]pyrimidine-6-carboxylate $^1$H-NMR (DMSO-$d_6$) δ: 1.29 (3H, t, J=7.1 Hz), 2.81 (3H, s), 4.08 (2H, s), 4.29 (2H, q, J=7.1 Hz), 7.58, 7.70 (4H, AB, J=8.1 Hz), 12.82 (1H, br s)
MS (m/z): 396 (M$^+$)

Production Example 18

Ethyl 2-(cyclopent-1-enylmethyl)-5-methyl-4-oxo-3,4-dihydrothieno[2,3-d]pyrimidine-6-carboxylate $^1$H-NMR (DMSO-$d_6$) δ: 1.30 (3H, t, J=7.1 Hz), 1.7-1.9 (2H, m), 2.2-2.4 (4H, m), 2.81 (3H, s), 3.41 (2H, s), 4.30 (2H, q, J=7.2 Hz), 5.47 (1H, d, J=1.5 Hz), 12.56 (1H, br s)
MS (m/z): 318 (M$^+$)

Production Example 19

Ethyl 2-cyclopentylmethyl-5-methyl-4-oxo-3,4-dihydrothieno[2,3-d]pyrimidine-6-carboxylate $^1$H-NMR (DMSO-$d_6$) δ: 1.1-1.3 (2H, m), 1.30 (3H, t, J=7.1 Hz), 1.4-1.9 (6H, m), 2.2-2.4 (1H, m), 2.61 (2H, d, J=7.3 Hz), 2.81 (3H, s), 4.29 (2H, q, J=7.1 Hz), 12.50 (1H, br s)
MS (m/z): 320 (M$^+$)

Production Example 20

Ethyl 2-cyclohexylmethyl-5-methyl-4-oxo-3,4-dihydrothieno[2,3-d]pyrimidine-6-carboxylate $^1$H-NMR (DMSO-$d_6$) δ: 0.9-1.3 (5H, m), 1.31 (3H, t, J=7.1 Hz), 1.5-1.9 (6H, m), 2.81 (3H, s), 4.30 (2H, q, J=7.1 Hz), 12.48 (1H, br s)
MS (m/z): 334 (M$^+$)

Production Example 21

Ethyl 2-(4-tert-butoxycarbonylpiperazin-1-ylmethyl)-5-methyl-4-oxo-3,4-dihydrothieno[2,3-d]pyrimidine-6-carboxylate A mixture of 1.15 g of ethyl 2-chloromethyl-5-methyl-4-oxo-3,4-dihydrothieno[2,3-d]pyrimidine-6-carboxylate, 745 mg of tert-butoxycarbonylpiperazine, 20 mL of ethylene glycol and 400 mg of triethylamine was stirred at 80° C. for 3 hours. Thereafter water was added to the reaction mixture, followed by extraction with chloroform, drying over anhydrous magnesium sulfate, and removal of the solvent by distillation under reduced pressure. The residue was purified on silica gel column chromatography (ethyl acetate:chloroform:hexane=2:1:1) to provide 1.36 g (78%) of the title compound.
$^1$H-NMR (CDCl$_3$) δ: 1.40 (3H, t, J=7.0 Hz), 1.47 (9H, s), 2.55 (4H, t, J=4.8 Hz), 2.94 (3H, s), 3.51 (4H, t, J=4.8 Hz), 3.58 (2H, s), 4.37 (2H, q, J=7.3 Hz)
MS (m/z): 436 (M$^+$), 129 (base)

Production Example 22

Ethyl 3-benzyl-2,5-dimethyl-4-oxo-3,4-dihydrothieno[2,3-d]-pyrimidine-6-carboxylate A mixture of 252 mg of ethyl 2,5-dimethyl-4-oxo-3,4-dihydrothieno[2,3-d]pyrimidine-6-carboxylate, 138 mg of potassium carbonate, 15 mL of acetonitrile and 1 mL of benzyl chloride was heated under reflux overnight. After condensing the reaction mixture under reduced pressure, the residue was purified on silica gel column chromatography (chloroform:methanol=100:1) to provide 153 mg (45%) of the title compound.
$^1$H-NMR (CDCl$_3$) δ: 1.40 (3H, t, J=6.9 Hz), 2.54 (3H, s), 2.96 (3H, s), 4.37 (2H, q, J=6.9 Hz), 5.35 (2H, s), 7.1-7.2 (2H, m), 7.2-7.4 (3H, m)
MS (m/z): 342 (M$^+$), 91 (base)

Production Example 23

Ethyl 2-(3,4-dichlorobenzyl)-3,5-dimethyl-4-oxo-3,4-dihydrothieno[2,3-d]pyrimidine-6-carboxylate A mixture of 100 mg of ethyl 2-(3,4-dichlorobenzyl)-5-methyl-4-oxo-3,4-dihydrothieno[2,3-d]pyrimidine-6-carboxylate, 40 mg of potassium carbonate, 10 mL of acetonitrile and 40 mg of methyl iodide was heated under reflux for 1.5 hours. After condensing the reaction mixture under reduced pressure, the residue was purified on silica gel column chromatography (ethyl acetate:hexane=1:1) to provide 60 mg (58%) of the title compound.

$^1$H-NMR (CDCl$_3$) δ: 2.92 (3H, s), 3.47 (3H, s), 3.88 (3H, t, J=6.9 Hz), 4.15 (2H, s), 4.37 (2H, q, J=6.9 Hz), 7.0-7.1 (1H, m), 7.34 (1H, d, J=1.9 Hz), 7.41 (1H, d, J=8.4 Hz)

MS (m/z): 412 (M$^+$+2), 410 (M$^+$), 159 (base)

Production Example 24

Butyl 5-amino-4-ethoxycarbonyl-3-methyl-2-thiopheneacetate

A mixture of 1.72 g of butyl 4-oxopentanoate, 352 mg of sulfur, 1.13 g of ethyl cyanoacetate, 5 mL of ethanol and 1 mL of diethylamine was stirred at room temperature overnight. Chloroform was added to the reaction mixture, followed by washing with saturated aqueous sodium bicarbonate solution, drying over anhydrous magnesium sulfate and removal of the solvent by distillation under reduced pressure. The residue was purified on silica gel column chromatography (hexane:ethyl acetate=3:1) to provide 1.20 g (40.1%) of the title compound.

$^1$H-NMR (CDCl$_3$) δ: 0.9-1.0 (3H, m), 1.3-1.5 (5H, m), 1.5-1.7 (2H, m), 2.19 (3H, s), 2.5-2.6 (2H, m), 2.7-2.8 (2H, m), 4.0-4.2 (2H, m)

MS (m/z): 299 (M$^+$), 198 (base)

Production Example 25

Butyl 2-(3,4-dichlorobenzyl)-5-methyl-4-oxo-3,4-dihydrothieno[2,3-d]pyrimidine-6-acetate A mixture of 900 mg of butyl 5-amino-4-ethoxycarbonyl-3-methyl-2-thiopheneacetate, 558 mg of (3,4-dichlorophenyl)acetonitrile and 20 mL of 4N hydrochloric acid/1,4-dioxane solution was stirred at room temperature overnight. Ice water was added to the reaction mixture, followed by neutralization with 25% aqueous ammonia, extraction with chloroform, drying over anhydrous magnesium sulfate and removal of the solvent by distillation under reduced pressure. The residue was purified on silica gel column chromatography (chloroform:methanol=50:1) to provide 500 mg (38%) of the title compound.

$^1$H-NMR (CDCl$_3$) δ: 0.8-1.0 (3H, m), 1.3-1.5 (2H, m), 1.6-1.7 (2H, m), 2.58 (3H, s), 3.81 (2H, s), 4.01 (2H, s), 4.1-4.2 (2H, m), 7.2-7.4 (1H, m), 7.39 (1H, d, J=8.5 Hz), 7.59 (1H, d, J=2.3 Hz), 12.35 (1H, s)

MS (m/z): 440 (M$^+$+2), 438 (M$^+$)

Production Example 26

Ethyl 5-amino-4-ethoxycarbonyl-3-methyl-2-thiophenepropionate

The title compound was obtained in the manner similar to Production Example 24.

MS (m/z): 285 (M$^+$)

Production Example 27

Ethyl 2-(3,4-dichlorobenzyl)-5-methyl-4-oxo-3,4-dihydro-6-thieno[2,3-d]pyrimidine-6-propionate The title compound was obtained in the manner similar to Production Example 25.

$^1$H-NMR (DMSO-d$_6$) δ: 1.16 (3H, t, J=7.1 Hz), 2.39 (3H, s), 2.59 (2H, t, J=7.1 Hz), 3.00 (2H, t, J=7.1 Hz), 3.94 (2H, s), 4.05 (2H, q, J=7.1 Hz), 7.2-7.7 (3H, m), 12.43 (1H, br s)

MS (m/z): 426 (M$^+$+2), 424 (M$^+$)

Production Example 28

Ethyl 5-amino-4-ethoxycarbonyl-3-methyl-2-thiophenebutyrate

The title compound was obtained in the manner similar to Production Example 24.

$^1$H-NMR (CDCl$_3$) δ: 1.1-1.4 (6H, m), 1.7-1.9 (2H, m), 2.17 (3H, s), 2.2-2.4 (2H, m), 2.60 (2H, t, J=7.5 Hz), 4.0-4.2 (2H, m), 4.2-4.4 (2H, m), 5.91 (2H, br s)

MS (m/z): 299 (M$^+$)

Production Example 29

Ethyl 2-(3,4-dichlorobenzyl)-5-methyl-4-oxo-3,4-dihydrothieno[2,3-d]pyrimidine-6-butyrate The title compound was obtained in the manner similar to Production Example 25.

$^1$H-NMR (DMSO-d$_6$) δ: 1.17 (3H, t, J=7.1 Hz), 1.7-1.9 (2H, m), 2.34 (2H, t, J=7.3 Hz), 2.37 (3H, s), 2.76 (2H, t, J=7.5 Hz), 3.94 (2H, s), 4.04 (2H, q, J=7.1 Hz), 7.2-7.7 (3H, m), 12.44 (1H, br s)

MS (m/z): 440 (M$^+$+2), 438 (M$^+$)

Production Example 30

Diethyl 5-amino-3-trifluoromethylthiophene-2,4-dicarboxylate

The title compound was obtained in the manner similar to Production Example 24.

MS (m/z): 311 (M$^+$)

Production Example 31

Ethyl 2-(3,4-dichlorobenzyl)-4-oxo-5-trifluoromethyl-3,4-dihydrothieno[2,3-d]pyrimidine-6-carboxylate The title compound was obtained in the manner similar to Production Example 25.

$^1$H-NMR (DMSO-d$_6$) δ: 1.29 (3H, t, J=7.1 Hz), 4.04 (2H, s), 4.36 (2H, q, J=7.1 Hz), 7.3-7.7 (3H, m), 13.05 (1H, br s)

MS (m/z): 452 (M$^+$+2), 450 (M$^+$)

Production Example 32

4-Ethyl-2-methyl 5-amino-3-methoxymethylthiophene-2,4-dicarboxylate

The title compound was obtained in the manner similar to Production Example 24.

MS (m/z): 273 (M$^+$)

Production Example 33

Methyl 2-(3,4-dichlorobenzyl)-5-methoxymethyl-4-oxo-3,4-dihydrothieno[2,3-d]pyrimidine-6-carboxylate The title compound was obtained in the manner similar to Production Example 25.

¹H-NMR (DMSO-d₆) δ: 3.58 (3H, s), 3.79 (2H, s), 3.90 (3H, s), 3.94 (2H, s), 7.2-7.7 (3H, m), 12.48 (1H, br s)
MS (m/z): 414 (M⁺+2), 412 (M⁺)

Compounds of Production Examples 34-79 were synthesized in the manner similar to Production Example 1.

Production Example 34

Ethyl 5-methyl-2-(2-naphthyl)-4-oxo-3,4-dihydrothieno-[2,3-d]pyrimidine-6-carboxylate MS (m/z): 364 (M⁺, base)

Production Example 35

Ethyl 2-(2-methoxycarbonylbenzyl)-5-methyl-4-oxo-3,4-dihydrothieno[2,3-d]pyrimidine-6-carboxylate ¹H-NMR (DMSO-d₆) δ: 1.28 (3H, t, J=7.1 Hz), 2.82 (3H, s), 3.72 (3H, s), 4.28 (2H, q, J=7.1 Hz), 4.34 (2H, s), 7.3-7.5 (2H, m), 7.58 (1H, dt, J=1.5, 7.7 Hz), 7.89 (1H, dd, J=1.5, 7.7 Hz), 11.27 (1H, br s)
MS (m/z): 386 (M⁺), 354 (base)

Production Example 36

Ethyl 5-methyl-4-oxo-2-(pyridin-2-ylmethyl)-3,4-dihydrothieno[2,3-d]pyrimidine-6-carboxylate ¹H-NMR (DMSO-d₆) δ: 1.29 (3H, t, J=6.9 Hz), 2.83 (3H, s), 4.29 (2H, q, J=6.9 Hz), 4.44 (2H, s), 7.6-7.9 (2H, m), 8.1-8.3 (1H, m), 8.72 (1H, d, J=4.6 Hz), 12.89 (1H, br s)
MS (m/z): 329 (M⁺, base)

Production Example 37

Ethyl 2-benzhydryl-5-methyl-4-oxo-3,4-dihydrothieno-[2,3-d]pyrimidine-6-carboxylate ¹H-NMR (DMSO-d₆) δ: 1.29 (3H, t, J=6.9 Hz), 2.81 (3H, s), 4.30 (2H, q, J=6.9 Hz), 5.52 (1H, s), 7.2-7.4 (10H, m), 12.87 (1H, br s)
MS (m/z): 404 (M⁺, base)

Production Example 38

Ethyl 2-(3-bromo-4-methoxybenzyl)-5-methyl-4-oxo-3,4-dihydrothieno[2,3-d]pyrimidine-6-carboxylate ¹H-NMR (DMSO-d₆) δ: 1.30 (3H, t, J=6.9 Hz), 2.80 (3H, s), 3.82 (3H, s), 3.90 (2H, s), 4.29 (2H, q, J=6.9 Hz), 7.07 (1H, d, J=8.5 Hz), 7.33 (1H, dd, J=2.1, 8.5 Hz), 7.60 (1H, d, J=2.1 Hz), 12.72 (1H, br s)
MS (m/z): 438 (M⁺+2), 436 (M⁺, base)

Production Example 39

Ethyl 2-(2-chloro-5-trifluoromethylbenzyl)-5-methyl-4-oxo-3,4-dihydrothieno[2,3-d]pyrimidine-6-carboxylate ¹H-NMR (DMSO-d₆) δ: 1.28 (3H, t, J=7.1 Hz), 2.82 (3H, s), 4.27 (2H, s), 4.28 (2H, q, J=7.1 Hz), 7.72 (2H, d, J=1.5 Hz), 7.91 (1H, s), 12.84 (1H, s)
MS (m/z): 432 (M⁺+2), 430 (M⁺), 395 (base)

Production Example 40

Ethyl 2-(2-fluoro-3-trifluoromethylbenzyl)-5-methyl-4-oxo-3,4-dihydrothieno[2,3-d]pyrimidine-6-carboxylate ¹H-NMR (DMSO-d₆) δ: 1.29 (3H, t, J=7.1 Hz), 2.82 (3H, s), 4.16 (2H, s), 4.29 (2H, q, J=7.1 Hz), 7.40 (1H, t, J=7.7 Hz), 7.6-7.8 (2H, m), 12.83 (1H, br s)
MS (m/z): 414 (M⁺, base)

Production Example 41

Ethyl 2-(2-fluoro-5-trifluoromethylbenzyl)-5-methyl-4-oxo-3,4-dihydrothieno[2,3-d]pyrimidine-6-carboxylate ¹H-NMR (DMSO-d₆) δ: 1.29 (3H, t, J=7.1 Hz), 2.82 (3H, s), 4.16 (2H, s), 4.28 (2H, q, J=7.1 Hz), 7.45 (1H, t, J=9.1 Hz), 7.7-7.8 (1H, m), 7.9 (1H, dd, J=1.9, 6.6 Hz), 12.80 (1H, br s)
MS (m/z): 414 (M⁺, base)

Production Example 42

Ethyl 2-(3-chloro-2-fluorobenzyl)-5-methyl-4-oxo-3,4-dihydrothieno[2,3-d]pyrimidine-6-carboxylate ¹H-NMR (DMSO-d₆) δ: 1.29 (3H, t, J=7.1 Hz), 2.82 (3H, s), 4.11 (2H, s), 4.29 (2H, q, J=7.1 Hz), 7.21 (1H, dt, J=1.0, 7.9 Hz), 7.3-7.4 (1H, m), 7.4-7.6 (1H, m), 12.77 (1H, br s)
MS (m/z): 382 (M⁺+2), 380 (M⁺, base)

Production Example 43

Ethyl 2-(3-chloro-4-fluorobenzyl)-5-methyl-4-oxo-3,4-dihydrothieno[2,3-d]pyrimidine-6-carboxylate ¹H-NMR (DMSO-d₆) δ: 1.30 (3H, t, J=7.1 Hz), 2.80 (3H, s), 3.98 (2H, s), 4.29 (2H, q, J=7.1 Hz), 7.3-7.5 (2H, m), 7.5-7.7 (1H, m), 12.75 (1H, br s)
MS (m/z): 382 (M⁺+2), 380 (M⁺, base)

Production Example 44

Ethyl 2-(5-chloro-2-fluorobenzyl)-5-methyl-4-oxo-3,4-dihydrothieno[2,3-d]pyrimidine-6-carboxylate ¹H-NMR (DMSO-d₆) δ: 1.29 (3H, t, J=6.9 Hz), 2.82 (3H, s), 4.06 (2H, s), 4.29 (2H, q, J=6.9 Hz), 7.26 (1H, t, J=9.1 Hz), 7.3-7.5 (1H, m), 7.52 (1H, dd, J=2.7, 6.2 Hz)
MS (m/z): 382 (M⁺+2), 380 (M⁺, base)

Production Example 45

Ethyl 2-benzyl-4-oxo-3,4-dihydrothieno[2,3-d]pyrimidine-6-carboxylate

¹H-NMR (DMSO-d₆) δ: 1.31 (3H, t, J=7.1 Hz), 3.99 (2H, s), 4.32 (2H, q, J=7.1 Hz), 7.2-7.4 (5H, m), 7.92 (1H, s), 12.92 (1H, br s)
MS (m/z): 314 (M⁺), 91 (base)

Production Example 46

Ethyl 2-(3,4-dichlorobenzyl)-4-oxo-3,4-dihydrothieno-[2,3-d]pyrimidine-6-carboxylate $^1$H-NMR (DMSO-$d_6$) δ: 1.31 (3H, t, J=7.1 Hz), 4.03 (2H, s), 4.32 (2H, q, J=7.1 Hz), 7.36 (1H, dd, J=1.9, 8.3 Hz), 7.60 (1H, d, J=8.3 Hz), 7.66 (1H, d, J=1.9 Hz), 7.92 (1H, s), 12.89 (1H, br s)
MS (m/z): 384 (M$^+$+2), 382 (M$^+$, base)

Production Example 47

Ethyl 5-methyl-2-(2-methylbenzyl)-4-oxo-3,4-dihydrothieno[2,3-d]pyrimidine-6-carboxylate $^1$H-NMR (DMSO-$d_6$) δ: 1.30 (3H, t, J=7.1 Hz), 2.30 (3H, s), 2.82 (3H, s), 3.99 (2H, s), 4.29 (2H, q, J=7.1 Hz), 7.0-7.2 (4H, m), 12.73 (1H, s)
MS (m/z): 342 (M$^+$)

Production Example 48

Ethyl 2-(3-benzyloxybenzyl)-5-methyl-4-oxo-3,4-dihydrothieno[2,3-d]pyrimidine-6-carboxylate $^1$H-NMR (DMSO-$d_6$) δ: 1.30 (3H, t, J=7.3 Hz), 2.82 (3H, s), 4.00 (2H, s), 4.29 (2H, q, J=7.3 Hz), 5.06 (2H, s), 6.9-7.0 (1H, m), 7.05 (1H, d, J=7.7 Hz), 7.2-7.3 (7H, m), 12.63 (1H, s)
MS (m/z): 434 (M$^+$)

Production Example 49

Ethyl 2-(4-ethylbenzyl)-5-methyl-4-oxo-3,4-dihydrothieno-[2,3-d]pyrimidine-6-carboxylate $^1$H-NMR (DMSO-$d_6$) δ: 1.15 (3H, t, J=7.7 Hz), 1.30 (3H, t, J=7.1 Hz), 2.57 (2H, q, J=7.7 Hz), 2.81 (3H, s), 3.92 (2H, s), 4.29 (2H, q, J=7.1 Hz), 7.16 (2H, d, J=8.1 Hz), 7.26 (2H, d, J=8.1 Hz), 12.76 (1H, br s)
MS (m/z): 356 (M$^+$)

Production Example 50

Ethyl 2-(4-isopropylbenzyl)-5-methyl-4-oxo-3,4-dihydrothieno[2,3-d]pyrimidine-6-carboxylate $^1$H-NMR (DMSO-$d_6$) δ: 1.17 (6H, d, J=7.0 Hz), 1.30 (3H, t, J=7.1 Hz), 2.80 (3H, s), 2.84 (1H, sep, J=7.0 Hz), 3.91 (2H, s), 4.29 (2H, q, J=7.1 Hz), 7.19 (2H, d, J=8.3 Hz), 7.27 (2H, d, J=8.3 Hz), 12.77 (1H, s)
MS (m/z): 370 (M$^+$)

Production Example 51

Ethyl 2-{3,5-bis(trifluoromethyl)benzyl}-5-methyl-4-oxo-3,4-dihydrothieno[2,3-d]pyrimidine-6-carboxylate $^1$H-NMR (DMSO-$d_6$) δ: 1.29 (3H, t, J=7.1 Hz), 2.80 (3H, s), 4.23 (2H, s), 4.28 (2H, q, J=7.1 Hz), 8.01 (1H, s), 8.11 (2H, s), 12.81 (1H, s)
MS (m/z): 464 (M$^+$)

Production Example 52

Ethyl 2-(3,4-difluorobenzyl)-5-methyl-4-oxo-3,4-dihydrothieno[2,3-d]pyrimidine-6-carboxylate $^1$H-NMR (DMSO-$d_6$) δ: 1.30 (3H, t, J=7.0 Hz), 2.81 (3H, s), 3.98 (2H, s), 4.29 (2H, q, J=7.0 Hz), 7.1-7.5 (3H, m), 12.76 (1H, s)
MS (m/z): 364 (M+)

Production Example 53

Ethyl 2-(2,5-difluorobenzyl)-5-methyl-4-oxo-3,4-dihydrothieno[2,3-d]pyrimidine-6-carboxylate $^1$H-NMR (DMSO-$d_6$) δ: 1.29 (3H, t, J=7.3 Hz), 2.82 (3H, s), 4.06 (2H, s), 4.28 (2H, q, J=7.3 Hz), 7.1-7.4 (3H, m), 12.82 (1H, br s)
MS (m/z): 364 (M$^+$)

Production Example 54

Ethyl 5-methyl-4-oxo-2-(2-trifluoromethoxybenzyl)-3,4-dihydrothieno[2,3-d]pyrimidine-6-carboxylate $^1$H-NMR (DMSO-$d_6$) δ: 1.29 (3H, t, J=7.3 Hz), 2.82 (3H, s), 4.10 (2H, s), 4.28 (2H, q, J=7.3 Hz), 7.3-7.5 (4H, m), 12.89 (1H, br s)
MS (m/z): 412 (M$^+$)

Production Example 55

Ethyl 5-methyl-4-oxo-2-(thiophen-3-yl)-3,4-dihydrothieno-[2,3-d]pyrimidine-6-carboxylate $^1$H-NMR (DMSO-$d_6$) δ: 1.32 (3H, t, J=7.3 Hz), 2.86 (3H, s), 4.31 (2H, q, J=7.3 Hz), 7.72 (1H, dd, J=3.1, 5.0 Hz), 7.8-7.9 (1H, m), 8.6-8.7 (1H, m), 12.71 (1H, s)
MS (m/z): 320 (M$^+$)

Production Example 56

Ethyl 2-(4-hydroxybenzyl)-5-methyl-4-oxo-3,4-dihydrothieno-[2,3-d]pyrimidine-6-carboxylate $^1$H-NMR (DMSO-$d_6$) δ: 1.30 (3H, t, J=7.1 Hz), 2.80 (3H, s), 3.82 (2H, s), 4.29 (2H, q, J=7.1 Hz), 6.71 (2H, d, J=8.5 Hz), 7.14 (2H, d, J=8.5 Hz), 9.32 (1H, s), 12.70 (1H, s)
MS (m/z): 344 (M$^+$)

Production Example 57

Ethyl 2-(5-bromo-2-methoxybenzyl)-5-methyl-4-oxo-3,4-dihydrothieno[2,3-d]pyrimidine-6-carboxylate $^1$H-NMR (DMSO-$d_6$) δ: 1.29 (3H, t, J=7.3 Hz), 2.82 (3H, s), 3.72 (3H, s), 4.00 (2H, s), 4.29 (2H, q, J=7.3 Hz), 6.97 (1H, d, J=8.5 Hz), 7.4-7.5 (2H, m), 12.68 (1H, br s)
MS (m/z): 438 (M$^+$+2), 436 (M$^+$)

Production Example 58

Ethyl 2-(3-fluoro-5-trifluoromethylbenzyl)-5-methyl-4-oxo-3,4-dihydrothieno[2,3-d]pyrimidine-6-carboxylate $^1$H-NMR (DMSO-$d_6$) δ: 1.29 (3H, t, J=7.3 Hz), 2.81 (3H, s), 4.12 (2H, s), 4.29 (2H, q, J=7.3 Hz), 7.0-7.7 (3H, m), 12.79 (1H, br s)
MS (m/z): 414 (M$^+$)

Production Example 59

Ethyl 2-(2-ethoxybenzyl)-5-methyl-4-oxo-3,4-dihydrothieno-[2,3-d]pyrimidine-6-carboxylate $^1$H-NMR (DMSO-$d_6$) δ: 1.18 (3H, t, J=6.9 Hz), 1.29 (3H, t, J=7.3 Hz), 2.82 (3H, s), 3.94 (2H, s), 3.95 (2H, q, J=6.9 Hz), 4.28 (2H, q, J=7.3 Hz), 6.8-6.9 (2H, m), 7.1-7.3 (2H, m), 12.74 (1H, br s).
MS (m/z): 372 (M+).

Production Example 60

Ethyl 5-methyl-4-oxo-2-phenyl-3,4-dihydrothieno-[2,3-d]pyrimidine-6-carboxylate $^1$H-NMR (DMSO-$d_6$) δ: 1.32 (3H, t, J=7.0 Hz), 2.87 (3H, s), 4.32 (2H, q, J=7.0 Hz), 7.5-7.7 (3H, m), 8.1-8.2 (2H, m), 12.80 (1H, s)
MS (m/z): 314 (M$^+$)

Production Example 61

Ethyl 5-methyl-4-oxo-2-phenoxy-3,4-dihydrothieno-[2,3-d]pyrimidine-6-carboxylate $^1$H-NMR (DMSO-$d_6$) δ: 1.27 (3H, t, J=7.3 Hz), 2.80 (3H, s), 4.26 (2H, q, J=7.3 Hz), 7.2-7.6 (5H, m), 13.03 (1H, s)
MS (m/z): 330 (M$^+$)

Production Example 62

Ethyl 2-(4-butoxybenzyl)-5-methyl-4-oxo-3,4-dihydrothieno[2,3-d]pyrimidine-6-carboxylate $^1$H-NMR (DMSO-$d_6$) δ: 0.92 (3H, t, J=6.9 Hz), 1.30 (3H, t, J=7.0 Hz), 1.41 (2H, sex, J=6.9 Hz), 1.67 (2H, quin, J=6.9 Hz), 2.80 (3H, s), 3.87 (2H, s), 3.93 (2H, t, J=6.9 Hz), 4.29 (2H, q, J=7.0 Hz), 6.87 (2H, d, J=8.4 Hz), 7.25 (2H, d, J=8.4 Hz), 12.73 (1H, s)
MS (m/z): 400 (M$^+$)

Production Example 63

Ethyl 2-(4-tert-butylbenzyl)-5-methyl-4-oxo-3,4-dihydrothieno[2,3-d]pyrimidine-6-carboxylate $^1$H-NMR (DMSO-$d_6$) δ: 1.25 (9H, s), 1.30 (3H, t, J=7.1 Hz), 2.80 (3H, s), 3.91 (2H, s), 4.29 (2H, q, J=7.1 Hz), 7.28 (2H, d, J=8.1 Hz), 7.35 (2H, d, J=8.1 Hz), 12.76 (1H, br s)
MS (m/z): 384 (M$^+$)

Production Example 64

Ethyl 2-(4-fluoro-3-trifluoromethylbenzyl)-5-methyl-4-oxo-3,4-dihydrothieno[2,3-d]pyrimidine-6-carboxylate $^1$H-NMR (DMSO-$d_6$) δ: 2.81 (3H, s), 4.07 (2H, s), 4.28 (2H, q, J=7.3 Hz), 7.1-7.2 (2H, m), 7.76 (1H, s), 12.77 (1H, br s)
MS (m/z): 414 (M$^+$)

Production Example 65

Ethyl 2-(2,4-difluorobenzyl)-5-methyl-4-oxo-3,4-dihydrothieno[2,3-d]pyrimidine-6-carboxylate $^1$H-NMR (DMSO-$d_6$) δ: 1.28 (3H, t, J=7.3 Hz), 2.82 (3H, s), 4.09 (2H, s), 4.28 (2H, q, J=7.3 Hz), 7.1-7.2 (2H, m), 7.4-7.5 (1H, m), 12.87 (1H, br s)
MS (m/z): 364 (M$^+$)

Production Example 66

Ethyl 2-(2-chloro-6-fluorobenzyl)-5-methyl-4-oxo-3,4-dihydrothieno[2,3-d]pyrimidine-6-carboxylate $^1$H-NMR (DMSO-$d_6$) δ: 1.28 (3H, t, J=7.3 Hz), 2.82 (3H, s), 4.19 (2H, s), 4.28 (2H, q, J=7.3 Hz), 7.2-7.4 (3H, m), 12.89 (1H, br s)
MS (m/z): 380 (M$^+$)

Production Example 67

Ethyl 2-(2,6-difluorobenzyl)-5-methyl-4-oxo-3,4-dihydrothieno[2,3-d]pyrimidine-6-carboxylate $^1$H-NMR (DMSO-$d_6$) δ: 1.29 (3H, t, J=6.9 Hz), 2.81 (3H, s), 4.03 (2H, s), 4.29 (2H, q, J=6.9 Hz), 7.0-7.1 (1H, m), 7.2-7.3 (1H, m), 7.4-7.5 (1H, m), 12.77 (1H, br s)
MS (m/z): 364 (M$^+$)

Production Example 68

Ethyl 5-methyl-4-oxo-2-phenylamino-3,4-dihydrothieno-[2,3-d]pyrimidine-6-carboxylate $^1$H-NMR (DMSO-$d_6$) δ: 1.29 (3H, t, J=7.3 Hz), 2.71 (3H, s), 4.25 (2H, q, J=7.3 Hz), 7.3-7.4 (2H, m), 7.5-7.6 (3H, m)
MS (m/z): 329 (M$^+$)

Production Example 69

Ethyl 5-methyl-4-oxo-2-(2-trifluoromethylthiobenzyl)-3,4-dihydrothieno[2,3-d]pyrimidine-6-carboxylate $^1$H-NMR (DMSO-$d_6$) δ: 1.30 (3H, t, J=7.0 Hz), 2.83 (3H, s), 4.29 (2H, q, J=7.0 Hz), 4.33 (2H, s), 7.4-7.6 (4H, m), 12.82 (1H, s)
MS (m/z): 428 (M$^+$)

Production Example 70

Ethyl 5-methyl-4-oxo-2-(2,3,5-trifluorobenzyl)-3,4-dihydrothieno[2,3-d]pyrimidine-6-carboxylate $^1$H-NMR (DMSO-$d_6$) δ: 1.30 (3H, t, J=7.3 Hz), 2.82 (3H, s), 4.12 (2H, s), 4.29 (2H, q, J=7.3 Hz), 7.1-7.3 (1H, m), 7.4-7.6 (1H, m), 12.82 (1H, s)
MS (m/z): 382 (M$^+$)

Production Example 71

Ethyl 5-methyl-4-oxo-2-(4-trifluoromethoxybenzyl)-3,4-dihydrothieno[2,3-d]pyrimidine-6-carboxylate $^1$H-NMR (DMSO-$d_6$) δ: 1.30 (3H, t, J=7.3 Hz), 2.81 (3H, s), 4.01 (2H, s), 4.29 (2H, q, J=7.3 Hz), 7.33 (2H, d, J=8.9 Hz), 7.49 (2H, d, J=8.9 Hz), 12.79 (1H, br s)
MS (m/z): 412 (M$^+$)

Production Example 72

Ethyl 5-methyl-4-oxo-2-(3-trifluoromethoxybenzyl)-3,4-dihydrothieno[2,3-d]pyrimidine-6-carboxylate $^1$H-NMR (DMSO-$d_6$) δ: 1.30 (3H, t, J=7.3 Hz), 2.81 (3H, s), 4.04 (2H, s), 4.29 (2H, q, J=7.3 Hz), 7.2-7.5 (4H, m)
MS (m/z): 412 (M$^+$)

Production Example 73

Ethyl 2-(2-benzyloxybenzyl)-5-methyl-4-oxo-3,4-dihydrothieno-[2,3-d]pyrimidine-6-carboxylate $^1$H-NMR (DMSO-$d_6$) δ: 1.30 (3H, t, J=7.3 Hz), 2.86 (3H, s), 4.00 (2H, s), 4.29 (2H, q, J=7.3 Hz), 5.06 (2H, s), 7.2-7.3 (9H, m), 12.62 (1H, br s)
MS (m/z): 434 (M$^+$)

Production Example 74

Ethyl 5-methyl-2-(4-methylthiobenzyl)-4-oxo-3,4-dihydrothieno[2,3-d]pyrimidine-6-carboxylate $^1$H-NMR (DMSO-$d_6$) δ: 1.30 (3H, t, J=7.3 Hz), 2.45 (3H, s), 2.81 (3H, s), 3.92 (2H, s), 4.29 (2H, q, J=7.3 Hz), 7.2-7.4 (4H, m)
MS (m/z): 374 (M$^+$)

Production Example 75

Ethyl 2-(5-fluoro-2-trifluoromethylbenzyl)-5-methyl-4-oxo-3,4-dihydrothieno[2,3-d]pyrimidine-6-carboxylate $^1$H-NMR (DMSO-$d_6$) δ: 1.29 (3H, t, J=7.3 Hz), 2.83 (3H, s), 4.26 (2H, s), 4.29 (2H, q, J=7.3 Hz), 7.3-7.5 (2H, m), 7.8-7.9 (1H, m), 12.83 (1H, s)
MS (m/z): 414 (M$^+$)

Production Example 76

Ethyl 2-(3-chlorobenzyl)-4-oxo-3,4-dihydrothieno-[2,3-d]pyrimidine-6-carboxylate $^1$H-NMR (DMSO-$d_6$) δ: 1.31 (3H, t, J=7.1 Hz), 4.01 (2H, s), 4.32 (2H, q, J=7.1 Hz), 7.2-7.4 (4H, m), 7.92 (1H, s), 12.91 (1H, br s)
MS (m/z): 348 (M$^+$)

Production Example 77

Ethyl 4-oxo-2-(thiophen-3-ylmethyl)-3,4-dihydrothieno-[2,3-d]pyrimidine-6-carboxylate $^1$H-NMR (DMSO-$d_6$) δ: 1.31 (3H, t, J=7.1 Hz), 4.01 (2H, s), 4.32 (2H, q, J=7.1 Hz), 7.2-7.4 (3H, m), 7.92 (1H, s), 12.91 (1H, br s)
MS (m/z): 320 (M$^+$)

Production Example 78

Ethyl 2-(cyclopent-1-enylmethyl)-4-oxo-3,4-dihydrothieno-[2,3-d]pyrimidine-6-carboxylate $^1$H-NMR (DMSO-$d_6$) δ: 1.31 (3H, t, J=7.1 Hz), 1.83 (2H, quin, J=7.5 Hz), 2.2-2.3 (4H, m), 3.44 (2H, s), 4.33 (2H, q, J=7.1 Hz), 5.4-5.5 (1H, m), 7.92 (1H, s), 12.70 (1H, br s)
MS (m/z): 304 (M$^+$)

Production Example 79

Ethyl 4-oxo-2-(3-trifluoromethylbenzyl)-3,4-dihydrothieno-[2,3-d]pyrimidine-6-carboxylate $^1$H-NMR (DMSO-$d_6$) δ: 1.31 (3H, t, J=7.1 Hz), 4.12 (2H, s), 4.32 (2H, q, J=7.1 Hz), 7.5-7.6 (4H, m), 7.92 (1H, s), 12.91 (1H, br s)
MS (m/z): 382 (M$^+$)

Production Example 80

Ethyl 4-chloro-2-(3,4-dichlorobenzyl)-5-methylthieno-[2,3-d]pyrimidine-6-carboxylate Three (3.00) g of ethyl 2-(3,4-dichlorobenzyl)-5-methyl-4-oxo-3,4-dihydrothieno[2,3-d]pyrimidine-6-carboxylate and 37 mL of phosphorus oxychloride were mixed, and to which 1.4 mL of N,N-dimethylaniline was added, followed by stirring at 90° for 4 hours. The reaction liquid was poured on ice and stirred for 3 hours, and the precipitated crystals were recovered by filtration and washed with water. Drying the crystals under aeration, 3.05 g of the title compound was obtained.
$^1$H-NMR (DMSO-$d_6$) δ: 1.41 (3H, t, J=7.1 Hz), 3.02 (3H, s), 4.26 (2H, s), 4.41 (2H, q, J=7.1 Hz), 7.23 (1H, dd, J=1.9, 8.1 Hz), 7.37 (1H, d, J=8.1 Hz), 7.48 (1H, d, J=1.9 Hz)
MS (m/z): 416 (M$^+$+2), 414 (M$^+$), 159 (base)

Production Example 81

Ethyl 2-(3,4-dichlorobenzyl)-5-methyl-4-thioxo-3,4-dihydrothieno[2,3-d]pyrimidine-6-carboxylate A mixture of 1.23 g of ethyl 4-chloro-2-(3,4-dichlorobenzyl)-5-methylthieno[2,3-d]pyrimidine-6-carboxylate, 594 mg of thiourea and 50 mL of ethanol was stirred at room temperature for 35 hours. Then 50 mL of water was added, followed by 30 minutes' stirring. Crystals were recovered by filtration and washed with water. Drying the same under aeration, 1.15 g of the title compound was obtained.
$^1$H-NMR (DMSO-$d_6$) δ: 1.30 (3H, t, J=7.1 Hz), 3.06 (3H, s), 4.13 (2H, s), 4.31 (2H, q, J=7.1 Hz), 7.35 (1H, dd, J=2.1, 8.3 Hz), 7.60 (1H, d, J=8.3 Hz), 7.67 (1H, d, J=2.1 Hz), 14.00 (1H, br s)
MS (m/z): 414 (M$^+$+2), 412 (M$^+$), 383 (base)

Production Example 82

Ethyl 2-(3-bromobenzyl)-4-chloro-5-methylthieno-[2,3-d]pyrimidine-6-carboxylate

The title compound was obtained in the manner similar to Production Example 80.
$^1$H-NMR (DMSO-$d_6$) δ: 1.41 (3H, t, J=7.1 Hz), 3.02 (3H, s), 4.28 (2H, s), 4.31 (2H, q,=7.1 Hz), 7.17 (1H, t, J=7.7 Hz), 7.2-7.4 (2H, m), 7.5-7.6 (1H, m)
MS (m/z): 426 (M$^+$+2), 424 (M$^+$), 169 (base)

Production Example 83

Ethyl 2-(3-bromobenzyl)-5-methyl-4-thioxo-3,4-dihydrothieno[2,3-d]pyrimidine-6-carboxylate The title compound was obtained in the manner similar to Production Example 81.
$^1$H-NMR (DMSO-$d_6$) δ: 1.30 (3H, t, J=7.1 Hz), 3.07 (3H, s), 4.12 (2H, s), 4.31 (2H, q, J=7.1 Hz), 7.2-7.4 (2H, m), 7.4-7.5 (1H, m), 7.5-7.7 (1H, m), 14.02 (1H, br s)
MS (m/z): 424 (M$^+$+2), 422 (M$^+$), 395 (base)

Production Example 84

Ethyl 4-chloro-5-methyl-2-(thiophen-2-ylmethyl)thieno-[2,3-d]pyrimidine-6-carboxylate The title compound was obtained in the manner similar to Production Example 80.
$^1$H-NMR (DMSO-$d_6$) δ: 1.41 (3H, t, J=7.1 Hz), 3.02 (3H, s), 4.41 (2H, q, J=7.1 Hz), 4.52 (2H, s), 6.94 (1H, dd, J=3.5, 5.0 Hz), 7.0-7.1 (1H, m), 7.19 (1H, dd, J=1.3, 5.0 Hz)
MS (m/z): 352 (M$^+$), 97 (base)

Production Example 85

Ethyl 5-methyl-2-(thiophen-2-ylmethyl)-4-thioxo-3,4-dihydrothieno[2,3-d]pyrimidine-6-carboxylate The title compound was obtained in the manner similar to Production Example 81.
$^1$H-NMR (DMSO-$d_6$) δ: 1.31 (3H, t, J=7.1 Hz), 3.07 (3H, s), 4.32 (2H, s), 4.32 (2H, q, J=7.1 Hz), 6.99 (1H, dd, J=3.5, 5.0 Hz), 7.05 (1H, dd, J=1.2, 3.5 Hz), 7.43 (1H, dd, J=1.2, 5.0 Hz), 14.05 (1H, br s)
MS (m/z): 350 (M$^+$), 97 (base)

Production Example 86

Ethyl 4-chloro-5-methyl-2-(thiophen-3-ylmethyl)thieno-[2,3-d]pyrimidine-6-carboxylate The title compound was obtained in the manner similar to Production Example 80.
$^1$H-NMR (DMSO-$d_6$) δ: 1.41 (3H, t, J=7.1 Hz), 3.02 (3H, s), 4.34 (2H, s), 4.41 (2H, q, J=7.1 Hz), 7.13 (1H, dd, J=1.2, 5.0 Hz), 7.1-7.3 (2H, m)
MS (m/z): 354 (M$^+$+2), 352 (M$^+$), 97 (base)

Production Example 87

Ethyl 5-methyl-2-(thiophen-3-ylmethyl)-4-thioxo-3,4-dihydrothieno[2,3-d]pyrimidine-6-carboxylate The title compound was obtained in the manner similar to Production Example 81.
$^1$H-NMR (DMSO-$d_6$) δ: 1.31 (3H, t, J=6.9 Hz), 3.07 (3H, s), 4.11 (2H, s), 4.31 (2H, q, J=6.9 Hz), 7.10 (1H, dd, J=1.2, 5.0 Hz), 7.3-7.4 (1H, m), 7.4-7.6 (1H, m), 13.99 (1H, br s)
MS (m/z): 350 (M$^+$), 97 (base)

Production Example 88

Ethyl 4-chloro-2-(cyclohex-1-enylmethyl)-5-methylthieno[2,3-d]pyrimidine-6-carboxylate The title compound was obtained in the manner similar to Production Example 80.
$^1$H-NMR (DMSO-$d_6$) δ: 1.41 (3H, t, J=7.1 Hz), 1.5-1.7 (4H, m), 1.9-2.1 (4H, m), 3.03 (3H, s), 3.64 (2H, s), 4.41 (2H, q, J=7.1 Hz), 5.4-5.5 (1H, m)
MS (m/z): 352 (M$^+$+2), 350 (M$^+$), 308 (base)

Production Example 89

Ethyl 2-(cyclohex-1-enylmethyl)-5-methyl-4-thioxo-3,4-dihydrothieno[2,3-d]pyrimidine-6-carboxylate The title compound was obtained in the manner similar to Production Example 81.
$^1$H-NMR (DMSO-$d_6$) δ: 1.31 (3H, t, J=6.9 Hz), 1.4-1.7 (4H, m), 1.8-2.1 (4H, m), 3.07 (3H, s), 3.39 (2H, s), 4.32 (2H, q, J=7.1 Hz), 5.4-5.6 (1H, m), 13.77 (1H, br s)
MS (m/z): 348 (M$^+$, base)

Production Example 90

Ethyl 2-benzyl-4-chloro-5-methylthieno-[2,3-d]pyrimidine-6-carboxylate

The title compound was obtained in the manner similar to Production Example 80.
$^1$H-NMR (DMSO-$d_6$) δ: 1.41 (3H, t, J=7.1 Hz), 3.01 (3H, s), 4.32 (2H, s), 4.40 (2H, q, J=7.1 Hz), 7.1-7.5 (5H, m)
MS (m/z): 345 (M$^+$), 91 (base)

Production Example 91

Ethyl 2-benzyl-5-methyl-4-thioxo-3,4-dihydrothieno-[2,3-d]pyrimidine-6-carboxylate The title compound was obtained in the manner similar to Production Example 81.
$^1$H-NMR (DMSO-$d_6$) δ: 1.30 (3H, t, J=6.9 Hz), 3.06 (3H, s), 4.11 (2H, s), 4.31 (2H, q, J=6.9 Hz), 7.2-7.4 (5H, m), 14.03 (1H, br s)
MS (m/z): 344 (M$^+$), 315 (base)

Production Example 92

Ethyl 4-chloro-2-(3-chlorobenzyl)-5-methylthieno-[2,3-d]pyrimidine-6-carboxylate The title compound was obtained in the manner similar to Production Example 80.
$^1$H-NMR (DMSO-$d_6$) δ: 1.41 (3H, t, J=7.1 Hz), 3.02 (3H, s), 4.29 (2H, s), 4.31 (2H, q, J=7.1 Hz), 7.1-7.3 (3H, m), 7.3-7.4 (1H, m)
MS (m/z): 380 (M$^+$), 125 (base)

Production Example 93

Ethyl 2-(3-chlorobenzyl)-5-methyl-4-thioxo-3,4-dihydrothieno[2,3-d]pyrimidine-6-carboxylate The title compound was obtained in the manner similar to Production Example 81.
$^1$H-NMR (DMSO-$d_6$) δ: 1.30 (3H, t, J=7.1 Hz), 3.06 (3H, s), 4.13 (2H, s), 4.31 (2H, q, J=7.1 Hz), 7.2-7.5 (4H, m), 14.02 (1H, br s)
MS (m/z): 380 (M$^+$+2), 378 (M$^+$), 349 (base)

Production Example 94

Ethyl 4-chloro-2-(3-chloro-4-fluorobenzyl)-5-methylthieno-[2,3-d]pyrimidine-6-carboxylate The title compound was obtained in the manner similar to Production Example 80.
$^1$H-NMR (DMSO-$d_6$) δ: 1.41 (3H, t, J=7.1 Hz), 3.02 (3H, s), 4.26 (2H, s), 4.41 (2H, q, J=7.1 Hz), 7.06 (1H, t, J=8.7 Hz), 7.2-7.3 (1H, m), 7.43 (1H, dd, J=2.3, 6.9 Hz)
MS (m/z): 400 (M$^+$+2), 398 (M$^+$), 143 (base)

Production Example 95

Ethyl 2-(3-chloro-4-fluorobenzyl)-5-methyl-4-thioxo-3,4-dihydrothieno[2,3-d]pyrimidine-6-carboxylate The title compound was obtained in the manner similar to Production Example 81.
$^1$H-NMR (DMSO-$d_6$) δ: 1.30 (3H, t, J=7.1 Hz), 3.06 (3H, s), 4.12 (2H, s), 4.31 (2H, q, J=7.1 Hz), 7.3-7.5 (2H, m), 7.5-7.7 (1H, m), 14.00 (1H, br s)
MS (m/z): 398 (M$^+$+2), 396 (M$^+$), 367 (base)

Production Example 96

Ethyl 4-chloro-5-methyl-2-(3-trifluoromethylbenzyl)thieno-[2,3-d]pyrimidine-6-carboxylate The title compound was obtained in the manner similar to Production Example 80.
$^1$H-NMR (DMSO-$d_6$) δ: 1.41 (3H, t, J=7.3 Hz), 3.02 (3H, s), 4.37 (2H, s), 4.40 (2H, q, J=7.3 Hz), 7.3-7.6 (3H, m), 7.67 (1H, s)
MS (m/z): 414 (M$^+$), 159 (base)

Production Example 97

Ethyl 5-methyl-4-thioxo-2-(3-trifluoromethylbenzyl)-3,4-dihydrothieno[2,3-d]pyrimidine-6-carboxylate The title compound was obtained in the manner similar to Production Example 81.
$^1$H-NMR (DMSO-$d_6$) δ: 1.30 (3H, t, J=7.1 Hz), 3.06 (3H, s), 4.23 (2H, s), 4.31 (2H, q, J=7.1 Hz), 7.5-7.7 (3H, m), 7.78 (1H, s), 14.05 (1H, br s)
MS (m/z): 412 (M$^+$), 383 (base)

Production Example 98

Ethyl 4-chloro-2-(3,4-dichlorobenzyl)thieno-[2,3-d]pyrimidine-6-carboxylate

The title compound was obtained in the manner similar to Production Example 80.
$^1$H-NMR (CDCl$_3$) δ: 1.42 (3H, t, J=7.3 Hz), 4.29 (2H, s), 4.44 (2H, q, J=7.3 Hz), 7.2-7.3 (1H, m), 7.37 (1H, d, J=8.5 Hz), 7.50 (1H, d, J=1.9 Hz), 8.05 (1H, s)
MS (m/z): 401 (M$^+$+1), 159 (base)

Production Example 99

Ethyl 2-(3,4-dichlorobenzyl)-4-thioxo-3,4-dihydrothieno-[2,3-d]pyrimidine-6-carboxylate The title compound was obtained in the manner similar to Production Example 81.
$^1$H-NMR (DMSO-$d_6$) δ: 1.32 (3H, t, J=7.1 Hz), 4.16 (2H, s), 4.33 (2H, q, J=7.1 Hz), 7.37 (1H, dd, J=1.9, 8.3 Hz), 7.61 (1H, d, J=8.3 Hz), 7.68 (1H, d, J=1.9 Hz), 8.06 (1H, s), 14.27 (1H, br s)
MS (m/z): 400 (M$^+$+2), 398 (M$^+$, base)

Production Example 100

Ethyl 2-benzyl-4-chlorothieno[2,3-d]pyrimidine-6-carboxylate

The title compound was obtained in the manner similar to Production Example 80.
$^1$H-NMR (DMSO-$d_6$) δ: 1.42 (3H, t, J=7.1 Hz), 4.35 (2H, s), 4.43 (2H, q, J=7.1 Hz), 7.2-7.5 (5H, m), 8.04 (1H, s)
MS (m/z): 331 (M$^+$−1), 91 (base)

Production Example 101

Ethyl 2-benzyl-4-thioxo-3,4-dihydrothieno[2,3-d]-pyrimidine-6-carboxylate

The title compound was obtained in the manner similar to Production Example 81.
$^1$H-NMR (DMSO-$d_6$) δ: 1.32 (3H, t, J=7.1 Hz), 4.13 (2H, s), 4.34 (2H, q, J=7.1 Hz), 7.2-7.4 (5H, m), 8.06 (1H, s), 14.30 (1H, br s)
MS (m/z): 330 (M$^+$, base)

Production Example 102

Ethyl 2-(3-chlorobenzyl)-5-methyl-4-thioxo-3,4-dihydrothieno[2,3-d]-pyrimidine-6-carboxylate The compound of Production Example 93 was prepared by a different method as follows. A mixture of 5.007 g of ethyl 2-3 (3-chlorobenzyl)-5-methyl-4-oxo-3,4-dihydrothieno[2,3-d]pyrimidine-6-carboxylate, 4.913 g of 2,4-bis(4-methoxyphenyl)-1,3-dithia-2,4-diphophetan-2,4-disulfide and 125 mL of dioxane was heated under reflux for 4.5 hours. Five (5) mL of water and 24.2 mL of aqueous sodium hydroxide solution were added to the reaction liquid and stirred. Further 100 mL of water was added and cooled with ice. Whereupon

Example 1

5-Methyl-4-oxo-2-(thiophen-3-ylmethyl)-3,4-dihydrothieno[2,3-d]pyrimidine-6-carboxylic acid

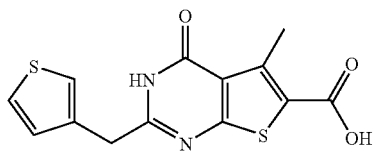

A mixture of 379 mg of ethyl 5-methyl-4-oxo-2-(thiophen-3-ylmethyl)-3,4-dihydrothieno[2,3-d]pyrimidine-6-carboxylate as synthesized in Production Example 1, 3.4 mL of 1N aqueous sodium hydroxide solution and 2.2 mL of ethanol was heated under reflux for 2 hours. After cooling off, the reaction liquid was poured on ice, rendered acidic with diluted hydrochloric acid, and the precipitated crystals were recovered by filtration. After washing with water, the crystals were dried by heating under reduced pressure, to provide 320 mg of 5-methyl-4-oxo-2-(thiophen-3-ylmethyl)-3,4-dihydrothieno[2,3-d]pyrimidine-6-carboxylic acid.

$^1$H-NMR (DMSO-$d_6$) δ: 2.79 (3H, s), 3.96 (2H, s), 7.0-7.6 (3H, m), 12.69 (1H, br s), 13.32 (1H, br s)

MS (m/z): 306 (M$^+$)

Compounds of Examples 2-68 were synthesized in the manner similar to Example 1.

Example 2

5-Methyl-4-oxo-2-(thiophen-2-ylmethyl)-3,4-dihydrothieno[2,3-d]pyrimidine-6-carboxylic acid

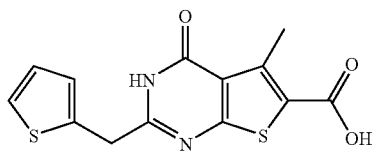

The title compound was synthesized from ethyl 5-methyl-4-oxo-2-(thiophen-2-ylmethyl)-3,4-dihydrothieno[2,3-d]-pyrimidine-6-carboxylate as synthesized in Production Example 2, in the manner similar to Example 1.

$^1$H-NMR (DMSO-$d_6$) δ: 2.79 (3H, s), 4.17 (2H, s), 6.9-7.5 (3H, m), 12.75 (1H, br s), 13.35 (1H, br s)

MS (m/z): 306 (M$^+$)

Example 3

2-(5-Chlorothiophen-2-ylmethyl)-5-methyl-4-oxo-3,4-dihydrothieno[2,3-d]pyrimidine-6-carboxylic acid

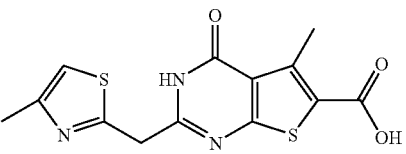

The title compound was synthesized from ethyl 2-(5-chlorothiophen-2-ylmethyl)-5-methyl-4-oxo-3,4-dihydrothieno[2,3-d]pyrimidine-6-carboxylate as synthesized in Production Example 3, in the manner similar to Example 1.

$^1$H-NMR (DMSO-$d_6$) δ: 2.79 (3H, s), 4.13 (2H, s), 6.91 (1H, d, J=3.9 Hz), 6.98 (1H, d, J=3.9 Hz), 12.74 (1H, br s), 13.37 (1H, br s)

MS (m/z): 342 (M$^+$+2), 340 (M$^+$)

Example 4

5-Methyl-2-(4-methylthiazol-2-ylmethyl)-4-oxo-3,4-dihydrothieno[2,3-d]pyrimidine-6-carboxylic acid

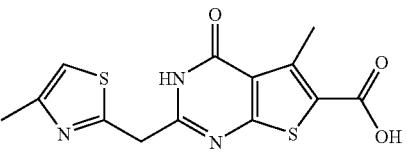

The title compound was synthesized from ethyl 5-methyl-2-(4-methylthiazol-2-ylmethyl)-4-oxo-3,4-dihydrothieno[2,3-d]-pyrimidine-6-carboxylate as synthesized in Production Example 4, in the manner similar to Example 1.

$^1$H-NMR (DMSO-$d_6$) δ: 2.32 (3H, d, J=0.8 Hz), 2.81 (3H, s), 4.36 (2H, s), 7.21 (1H, d, J=0.8 Hz), 12.80 (1H, br s), 13.37 (1H, br s)

MS (m/z): 321 (M$^+$)

Example 5

5-Methyl-4-oxo-2-(pyridin-3-ylmethyl)-3,4-dihydrothieno[2,3-d]pyrimidine-6-carboxylic acid

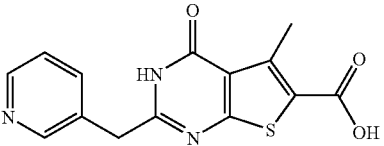

The title compound was synthesized from ethyl 5-methyl-4-oxo-2-(pyridin-3-ylmethyl)-3,4-dihydrothieno[2,3-d]-pyrimidine-6-carboxylate as synthesized similarly to Production Example 36, in the manner similar to Example 1.

MS (m/z): 301 (M$^+$), 257 (base)

Example 6

2-(2-Fluorobenzyl)-5-methyl-4-oxo-3,4-dihydrothieno[2,3-d]-pyrimidine-6-carboxylic acid

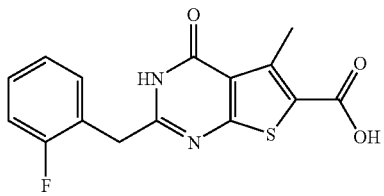

The title compound was synthesized from ethyl 2-(2-fluorobenzyl)-5-methyl-4-oxo-3,4-dihydrothieno[2,3-d]-pyrimidine-6-carboxylate as synthesized in Production Example 5, in the manner similar to Example 1.
$^1$H-NMR (DMSO-$d_6$) δ: 2.80 (3H, s), 4.04 (2H, s), 7.1-7.5 (4H, m), 12.74 (1H, br s), 13.35 (1H, br s)
MS (m/z): 318 (M$^+$)

Example 7

2-(3-Fluorobenzyl)-5-methyl-4-oxo-3,4-dihydrothieno[2,3-d]pyrimidine-6-carboxylic acid

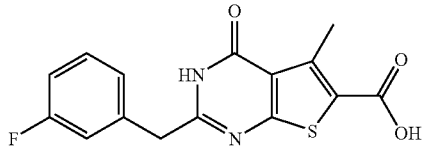

The title compound was synthesized from ethyl 2-(3-fluorobenzyl)-5-methyl-4-oxo-3,4-dihydrothieno[2,3-d]-pyrimidine-6-carboxylate as synthesized in Production Example 6, in the manner similar to Example 1.
$^1$H-NMR (DMSO-$d_6$) δ: 2.79 (3H, s), 3.99 (2H, s), 7.0-7.5 (4H, m), 12.74 (1H, br s), 13.34 (1H, br s)
MS (m/z): 318 (M$^+$)

Example 8

2-(4-Fluorobenzyl)-5-methyl-4-oxo-3,4-dihydrothieno[2,3-d]pyrimidine-6-carboxylic acid

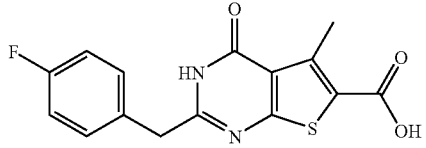

The title compound was synthesized from ethyl 2-(4-fluorobenzyl)-5-methyl-4-oxo-3,4-dihydrothieno[2,3-d]-pyrimidine-6-carboxylate as synthesized similarly to Production Example 6, in the manner similar to Example 1.
$^1$H-NMR (DMSO-$d_6$) δ: 2.78 (3H, s), 3.95 (2H, s), 7.1-7.2 (2H, m), 7.3-7.5 (2H, m), 12.72 (1H, s)
MS (m/z): 318 (M$^+$, base)

Example 9

2-(2-Chlorobenzyl)-5-methyl-4-oxo-3,4-dihydrothieno-[2,3-d]pyrimidine-6-carboxylic acid

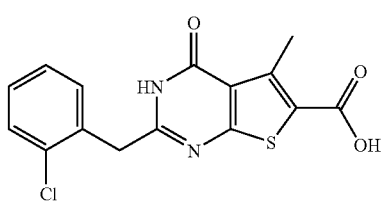

The title compound was synthesized from ethyl 2-(2-chlorobenzyl)-5-methyl-4-oxo-3,4-dihydrothieno-[2,3-d]pyrimidine-6-carboxylate as synthesized similarly to Production Example 7, in the manner similar to Example 1.
$^1$H-NMR (DMSO-$d_6$) δ: 2.80 (3H, s), 4.14 (2H, s), 7.3-7.5 (4H, m), 12.76 (1H, br s), 13.33 (1H, br s)
MS (m/z): 336 (M$^+$+2), 334 (M$^+$)

Example 10-a)

2-(3-Chlorobenzyl)-5-methyl-4-oxo-3,4-dihydrothieno-[2,3-d]pyrimidine-6-carboxylic acid

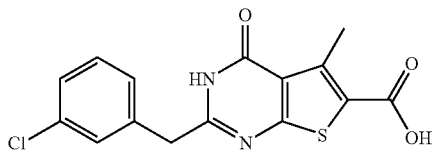

The title compound was synthesized from ethyl 2-(3-chlorobenzyl)-5-methyl-4-oxo-3,4-dihydrothieno-[2,3-d]pyrimidine-6-carboxylate as synthesized in Production Example 7, in the manner similar to Example 1.
$^1$H-NMR (DMSO-$d_6$) δ: 2.79 (3H, s), 3.98 (2H, s), 7.2-7.4 (3H, m), 7.45 (1H, s), 12.72 (1H, br s), 13.33 (1H, br s)
MS (m/z): 336 (M$^+$+2), 334 (M$^+$)

Example 10-b)

2-(3-Chlorobenzyl)-5-methyl-4-oxo-3,4-dihydrothieno[2,3-d]pyrimidine-6-carboxylic acid sodium salt

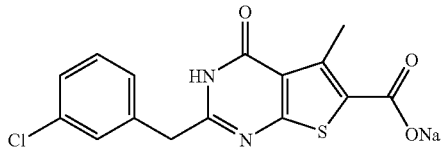

Sodium salt of the compound which was synthesized in above Example 10-a) was obtained.

¹H-NMR (DMSO-d₆) δ: 2.73 (3H, s), 3.92 (2H, s), 7.2-7.4 (3H, m), 7.44 (1H, s), 12.34 (1H, br s)

Example 10-c 2-(3-Chlorobenzyl)-5-methyl-4-oxo-3,4-dihydrothieno[2,3-d]pyrimidine-6-carboxylic acid sodium salt.½ ethanolate

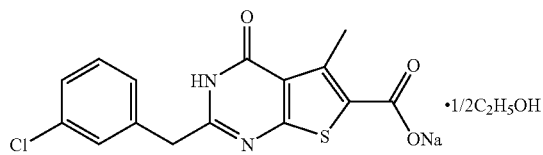

Sodium salt.½ ethanolated product of the compound which was synthesized in above Example 10-a) was obtained.
¹H-NMR (DMSO-d₆) δ: 1.06 (1.5H, t, J=7.0 Hz), 2.73 (3H, s), 3.44 (1H, q, J=6.9 Hz), 3.92 (2H, s), 4.34 (0.5H, br s).7.2-7.4 (3H, m), 7.44 (1H, s), 12.32 (1H, br s)
(The underlined part is the peak attributable to ethanol.)

Example 11

2-(4-Chlorobenzyl)-5-methyl-4-oxo-3,4-dihydrothieno-[2,3-d]pyrimidine-6-carboxylic acid

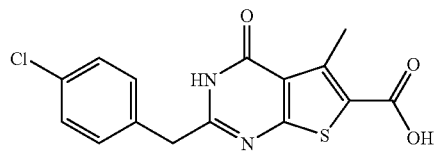

The title compound was synthesized from ethyl 2-(4-chlorobenzyl)-5-methyl-4-oxo-3,4-dihydrothieno-[2,3-d]pyrimidine-6-carboxylate as synthesized similarly to Production Example 7, in the manner similar to Example 1.
¹H-NMR (DMSO-d₆) δ: 2.79 (3H, s), 3.96 (2H, s), 7.3-7.5 (4H, m), 12.71 (1H, br s), 13.34 (1H, br s)
MS (m/z): 336 (M⁺+2), 334 (M⁺)

Example 12

2-(3-Bromobenzyl)-5-methyl-4-oxo-3,4-dihydrothieno-[2,3-d]pyrimidine-6-carboxylic acid

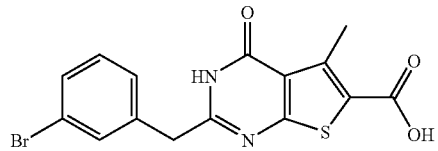

The title compound was synthesized from ethyl 2-(3-bromobenzyl)-5-methyl-4-oxo-3,4-dihydrothieno[2,3-d]pyrimidine-6-carboxylate as synthesized in Production Example 11, in the manner similar to Example 1.

¹H-NMR (DMSO-d₆) δ: 2.79 (3H, s), 3.97 (2H, s), 7.2-7.7 (4H, m), 12.71 (1H, br s), 13.34 (1H, br s)
MS (m/z): 380 (M⁺+2), 378 (M⁺)

Example 13

2-(4-Bromobenzyl)-5-methyl-4-oxo-3,4-dihydrothieno-[2,3-d]pyrimidine-6-carboxylic acid

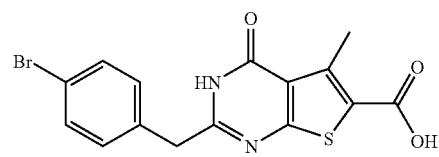

The title compound was synthesized from ethyl 2-(4-bromobenzyl)-5-methyl-4-oxo-3,4-dihydrothieno[2,3-d]-pyrimidine-6-carboxylate as synthesized in Production Example 12, in the manner similar to Example 1.
¹H-NMR (DMSO-d₆) δ: 2.78 (3H, s), 3.94 (2H, s), 7.2-7.6 (4H, m), 12.67 (1H, br s)
MS (m/z): 380 (M⁺+2), 378 (M⁺)

Example 14

5-Methyl-2-(2-methylbenzyl)-4-oxo-3,4-dihydrothieno[2,3-d]-pyrimidine-6-carboxylic acid

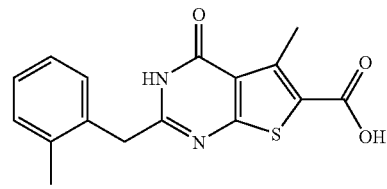

The title compound was synthesized from ethyl 5-methyl-2-(2-methylbenzyl)-4-oxo-3,4-dihydrothieno[2,3-d]pyrimidine-6-carboxylate as synthesized in Production Example 47, in the manner similar to Example 1.
¹H-NMR (DMSO-d₆) δ: 2.29 (3H, s), 2.80 (3H, s), 3.98 (2H, s), 7.1-7.2 (4H, m), 12.67 (1H, br s), 13.31 (1H, br s)
MS (m/z): 314 (M⁺)

Example 15

5-Methyl-2-(3-methylbenzyl)-4-oxo-3,4-dihydrothieno[2,3-d]-pyrimidine-6-carboxylic acid

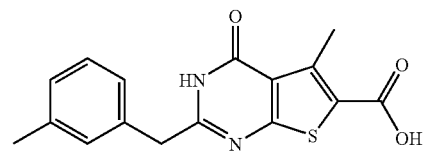

The title compound was synthesized from ethyl 5-methyl-2-(3-methylbenzyl)-4-oxo-3,4-dihydrothieno[2,3-d]pyrimidine-6-carboxylate as synthesized in Production Example 13, in the manner similar to Example 1.

¹H-NMR (DMSO-d₆) δ: 2.28 (3H, s), 2.79 (3H, s), 3.91 (2H, s), 7.0-7.3 (4H, m), 12.69 (1H, br s), 13.32 (1H, br s)
MS (m/z): 314 (M⁺)

Example 16

5-Methyl-2-(4-methylbenzyl)-4-oxo-3,4-dihydrothieno[2,3-d]-pyrimidine-6-carboxylic acid

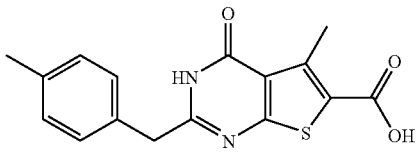

The title compound was synthesized from ethyl 5-methyl-2-(4-methylbenzyl)-4-oxo-3,4-dihydrothieno[2,3-d]pyrimidine-6-carboxylate as synthesized in Production Example 14, in the manner similar to Example 1.
¹H-NMR (DMSO-d₆) δ: 2.26 (3H, s), 2.78 (3H, s), 3.90 (2H, s), 7.0-7.3 (4H, m), 12.68 (1H, br s), 13.31 (1H, br s)
MS (m/z): 314 (M⁺)

Example 17

2-(2,6-Dimethylbenzyl)-5-methyl-4-oxo-3,4-dihydrothieno-[2,3-d]pyrimidine-6-carboxylic acid

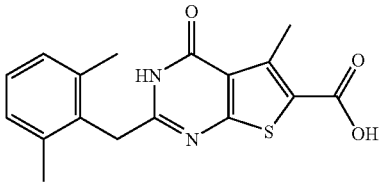

The title compound was synthesized from ethyl 2-(2,6-dimethylbenzyl)-5-methyl-4-oxo-3,4-dihydrothieno[2,3-d]-pyrimidine-6-carboxylate which was synthesized similarly to Production Example 14, in the manner similar to Example 1.
¹H-NMR (DMSO-d₆) δ: 2.24 (6H, s), 2.80 (3H, s), 4.40 (2H, s), 7.0-7.1 (3H, m), 12.70 (1H, br s), 13.25 (1H, br s)
MS (m/z): 328 (M⁺)

Example 18

2-(4-Ethylbenzyl)-5-methyl-4-oxo-3,4-dihydrothieno-[2,3-d]pyrimidine-6-carboxylic acid

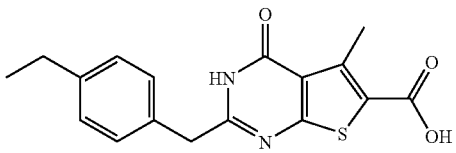

The title compound was synthesized from ethyl 5-methyl-2-(4-ethylbenzyl)-4-oxo-3,4-dihydrothieno[2,3-d]pyrimidine-6-carboxylate as synthesized in Production Example 49, in the manner similar to Example 1.
¹H-NMR (DMSO-d₆) δ: 1.15 (3H, t, J=7.7 Hz), 2.56 (2H, q, J=7.7 Hz), 2.78 (3H, s), 3.90 (2H, s), 7.16 (2H, d, J=8.1 Hz), 7.26 (2H, d, J=8.1 Hz), 12.70 (1H, br s), 13.32 (1H, br s)
MS (m/z): 328 (M⁺)

Example 19

2-(4-Isopropylbenzyl)-5-methyl-4-oxo-3,4-dihydrothieno-[2,3-d]pyrimidine-6-carboxylic acid

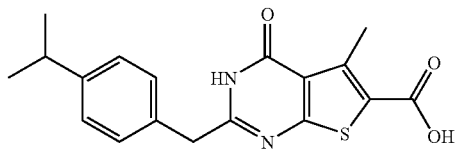

The title compound was synthesized from ethyl 5-methyl-2-(4-isopropylbenzyl)-4-oxo-3,4-dihydrothieno[2,3-d]pyrimidine-6-carboxylate as synthesized in Production Example 50, in the manner similar to Example 1.
¹H-NMR (DMSO-d₆) δ: 1.17 (6H, d, J=7.0 Hz), 2.78 (3H, s), 2.85 (1H, sep, J=7.0 Hz), 3.90 (2H, s), 7.19 (2H, d, J=8.1 Hz), 7.27 (2H, d, J=8.1 Hz), 12.69 (1H, br s), 13.32 (1H, br s)
MS (m/z): 342 (M⁺)

Example 20

2-(4-tert-Butylbenzyl)-5-methyl-4-oxo-3,4-dihydrothieno-[2,3-d]pyrimidine-6-carboxylic acid

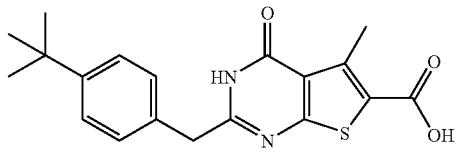

The title compound was synthesized from ethyl 2-(4-tert-butylbenzyl)-5-methyl-4-oxo-3,4-dihydrothieno[2,3-d]-pyrimidine-6-carboxylate as synthesized in Production Example 63, in the manner similar to Example 1.
¹H-NMR (DMSO-d₆) δ: 1.24 (9H, s), 2.75 (3H, s), 3.87 (2H, s), 7.2-7.4 (4H, m), 12.45 (1H, br s)
MS (m/z): 356 (M⁺)

Example 21

5-Methyl-4-oxo-2-(2-trifluoromethylbenzyl)-3,4-dihydrothieno[2,3-d]pyrimidine-6-carboxylic acid

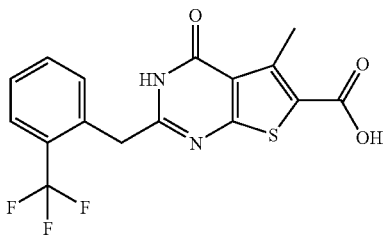

The title compound was synthesized from ethyl 5-methyl-4-oxo-2-(2-trifluoromethylbenzyl)-3,4-dihydrothieno-[2,3-d]pyrimidine-6-carboxylate as synthesized in Production Example 15, in the manner similar to Example 1.
$^1$H-NMR (DMSO-d$_6$) δ: 2.80 (3H, s), 4.23 (2H, s), 7.4-7.8 (4H, m), 12.77 (1H, br s), 13.32 (1H, br s)
MS (m/z): 368 (M$^+$)

Example 22

5-Methyl-4-oxo-2-(3-trifluoromethylbenzyl)-3,4-dihydrothieno[2,3-d]pyrimidine-6-carboxylic acid

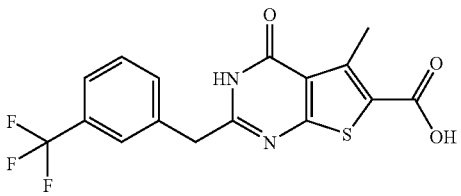

The title compound was synthesized from ethyl 5-methyl-4-oxo-2-(3-trifluoromethylbenzyl)-3,4-dihydrothieno-[2,3-d]pyrimidine-6-carboxylate as synthesized in Production Example 16, in the manner similar to Example 1.
$^1$H-NMR (DMSO-d$_6$) δ: 2.79 (3H, s), 4.08 (2H, s), 7.5-7.7 (3H, m), 7.76 (1H, s), 12.75 (1H, br s), 13.34 (1H, br s)
MS (m/z): 368 (M$^+$)

Example 23

5-Methyl-4-oxo-2-(4-trifluoromethylbenzyl)-3,4-dihydrothieno[2,3-d]pyrimidine-6-carboxylic acid

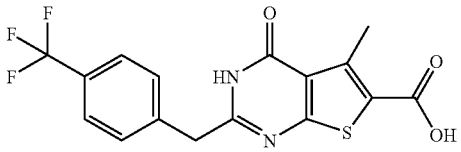

The title compound was synthesized from ethyl 5-methyl-4-oxo-2-(4-trifluoromethylbenzyl)-3,4-dihydrothieno-[2,3-d]pyrimidine-6-carboxylate as synthesized in Production Example 17, in the manner similar to Example 1.
$^1$H-NMR (DMSO-d$_6$) δ: 2.79 (3H, s), 4.08 (2H, s), 7.5-7.8 (4H, m), 12.77 (1H, br s), 13.34 (1H, br s)
MS (m/z): 368 (M$^+$)

Example 24

2-(4-Hydroxybenzyl)-5-methyl-4-oxo-3,4-dihydrothieno-[2,3-d]pyrimidine-6-carboxylic acid

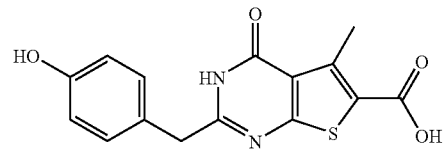

The title compound was synthesized from ethyl 2-(4-hydroxybenzyl)-5-methyl-4-oxo-3,4-dihydrothieno[2,3-d]-pyrimidine-6-carboxylate as synthesized in Production Example 56, in the manner similar to Example 1.
$^1$H-NMR (DMSO-d$_6$) δ: 2.78 (3H, s), 3.81 (2H, s), 6.6-6.7 (2H, m), 7.1-7.2 (2H, m), 9.31 (1H, br s), 12.63 (1H, br s), 13.31 (1H, br s)
MS (m/z): 316 (M$^+$)

Example 25

2-(2-Methoxybenzyl)-5-methyl-4-oxo-3,4-dihydrothieno-[2,3-d]pyrimidine-6-carboxylic acid

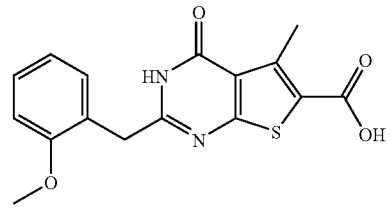

The title compound was synthesized from ethyl 2-(2-methoxybenzyl)-5-methyl-4-oxo-3,4-dihydrothieno[2,3-d]-pyrimidine-6-carboxylate as synthesized similarly to Production Example 59, in the manner similar to Example 1.
$^1$H-NMR (DMSO-d$_6$) δ: 2.79 (3H, s), 3.73 (3H, s), 3.93 (2H, s), 6.8-7.0 (1H, m), 6.98 (1H, d, J=7.9 Hz), 7.16 (1H, dd, J=1.5, 7.5 Hz), 7.2-7.3 (1H, m), 12.58 (1H, s)
MS (m/z): 330 (M$^+$), 299 (base)

Example 26

2-(3-Methoxybenzyl)-5-methyl-4-oxo-3,4-dihydrothieno-[2,3-d]pyrimidine-6-carboxylic acid

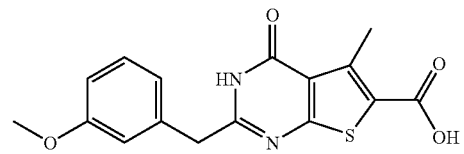

The title compound was synthesized from ethyl 2-(3-methoxybenzyl)-5-methyl-4-oxo-3,4-dihydrothieno[2,3-d]-pyrimidine-6-carboxylate which was synthesized similarly to Production Example 59, in the manner similar to Example 1.

$^1$H-NMR (DMSO-d$_6$) δ: 2.78 (3H, s), 3.73 (3H, s), 3.90 (2H, s), 6.82 (1H, dd, J=1.9, 8.1 Hz), 6.90 (1H, d, J=7.4 Hz), 6.94 (1H, s), 7.23 (1H, t, J=7.7 Hz), 12.64 (1H, br s)

MS (m/z): 330 (M$^+$, base)

Example 27

5-Methyl-4-oxo-2-(2-trifluoromethoxybenzyl)-3,4-dihydrothieno[2,3-d]pyrimidine-6-carboxylic acid

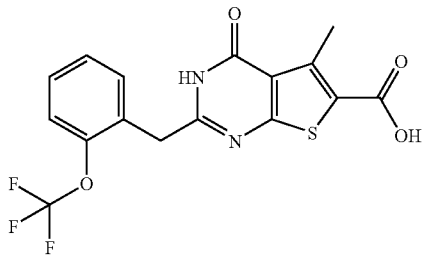

The title compound was synthesized from ethyl 5-methyl-4-oxo-2-(2-trifluoromethoxybenzyl)-3,4-dihydrothieno-[2,3-d]pyrimidine-6-carboxylate as synthesized in Production Example 54, in the manner similar to Example 1.

$^1$H-NMR (DMSO-d$_6$) δ: 2.80 (3H, s), 4.09 (2H, s), 7.3-7.5 (4H, m), 12.78 (1H, br s), 13.32 (1H, br s)

MS (m/z): 384 (M$^+$)

Example 28

5-Methyl-4-oxo-2-(3-trifluoromethoxybenzyl)-3,4-dihydrothieno[2,3-d]pyrimidine-6-carboxylic acid

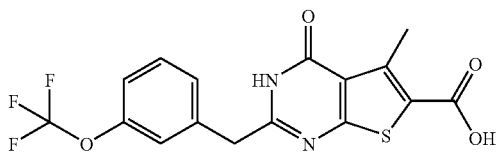

The title compound was synthesized from ethyl 5-methyl-4-oxo-2-(3-trifluoromethoxybenzyl)-3,4-dihydrothieno-[2,3-d]pyrimidine-6-carboxylate as synthesized in Production Example 72, in the manner similar to Example 1.

$^1$H-NMR (DMSO-d$_6$) δ: 2.79 (3H, s), 4.03 (2H, s), 7.2-7.3 (1H, m), 7.3-7.4 (2H, m), 7.4-7.5 (1H, m), 12.33 (1H, br s)

MS (m/z): 384 (M$^+$)

Example 29

5-Methyl-4-oxo-2-(4-trifluoromethoxybenzyl)-3,4-dihydrothieno[2,3-d]-pyrimidine-6-carboxylic acid The title compound was synthesized from ethyl 5-methyl-4-oxo-2-(4-trifluoromethoxybenzyl)-3,4-dihydrothieno-[2,3-d]pyrimidine-6-carboxylate as synthesized in Production Example 71, in the manner similar to Example 1.

$^1$H-NMR (DMSO-d$_6$) δ: 2.78 (3H, s), 4.00 (2H, s), 7.33 (2H, d, J=8.1 Hz), 7.48 (2H, d, J=8.1 Hz), 12.71 (1H, br s), 13.32 (1H, br s)

MS (m/z): 384 (M+)

Example 30

2-(2-(Benzyloxybenzyl)-5-methyl-4-oxo-3,4-dihydrothieno-[2,3-d]pyrimidine-6-carboxylic acid

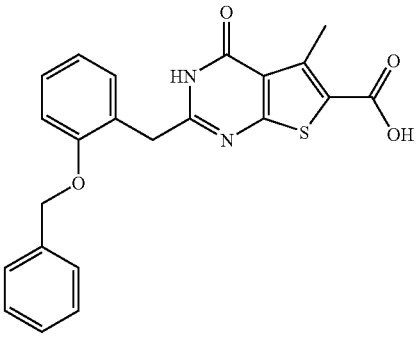

The title compound was synthesized from ethyl 2-(2-benzyloxybenzyl)-5-methyl-4-oxo-3,4-dihydrothieno[2,3-d]-pyrimidine-6-carboxylate as synthesized in Production Example 73, in the manner similar to Example 1.

$^1$H-NMR (DMSO-d$_6$) δ: 2.81 (3H, s), 4.00 (2H, s), 5.12 (2H, s), 6.9-7.0 (1H, m), 7.02 (1H, d, J=7.7 Hz), 7.2-7.3 (3H, m), 7.3-7.4 (2H, m), 7.52 (2H, d, J=7.3 Hz), 12.33 (1H, br s)

MS (m/z): 406 (M$^+$)

Example 31

2-(3-Benzyloxybenzyl)-5-methyl-4-oxo-3,4-dihydrothieno-[2,3-d]pyrimidine-6-carboxylic acid

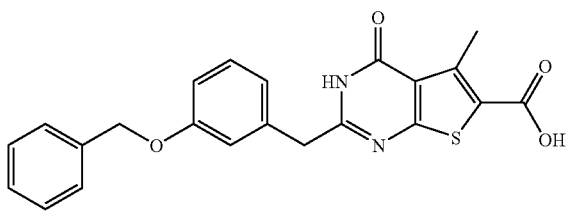

The title compound was synthesized from ethyl 2-(3-benzyloxybenzyl)-5-methyl-4-oxo-3,4-dihydrothieno[2,3-d]-pyrimidine-6-carboxylate as synthesized in Production Example 48, in the manner similar to Example 1.

$^1$H-NMR (DMSO-d$_6$) δ: 2.79 (3H, s), 3.91 (2H, s), 5.08 (2H, s), 6.8-7.5 (9H, m), 12.70 (1H, br s), 13.32 (1H, br s)

MS (m/z): 406 (M$^+$)

Example 32

2-(2-Ethoxybenzyl)-5-methyl-4-oxo-3,4-dihydrothieno-[2,3-d]pyrimidine-6-carboxylic acid

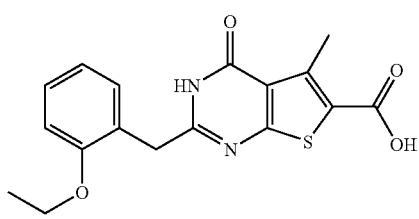

The title compound was synthesized from ethyl 2-(2-ethoxybenzyl)-5-methyl-4-oxo-3,4-dihydrothieno[2,3-d]-pyrimidine-6-carboxylate as synthesized in Production Example 59, in the manner similar to Example 1.

$^1$H-NMR (DMSO-$d_6$) δ: 1.18 (3H, t, J=7.0 Hz), 2.80 (3H, s), 3.94 (2H, s), 3.96 (2H, q, J=7.0 Hz), 6.8-6.9 (2H, m), 7.1-7.2 (2H, m), 12.58 (1H, br s), 13.28 (1H, br s)

MS (m/z): 344 (M$^+$)

Example 33

2-(4-Butoxybenzyl)-5-methyl-4-oxo-3,4-dihydrothieno-[2,3-d]pyrimidine-6-carboxylic acid

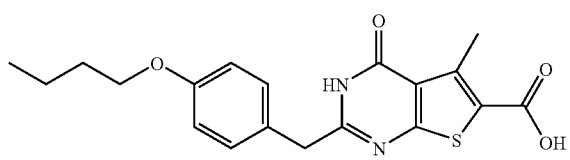

The title compound was synthesized from ethyl 2-(4-butoxybenzyl)-5-methyl-4-oxo-3,4-dihydrothieno[2,3-d]-pyrimidine-6-carboxylate as synthesized in Production Example 62, in the manner similar to Example 1.

$^1$H-NMR (DMSO-$d_6$) δ: 0.92 (3H, t, J=7.3 Hz), 1.4-1.5 (2H, m), 1.6-1.7 (2H, m), 2.78 (3H, s), 3.86 (2H, s), 3.93 (2H, t, J=6.6 Hz), 6.8-6.9 (2H, m), 7.2-7.3 (2H, m), 12.67 (1H, br s), 13.31 (1H, br s)

MS (m/z): 372 (M$^+$)

Example 34

2-(2,3-Dichlorobenzyl)-5-methyl-4-oxo-3,4-dihydrothieno-[2,3-d]pyrimidine-6-carboxylic acid

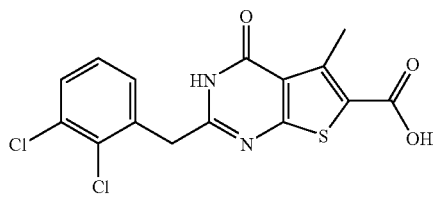

The title compound was synthesized from ethyl 2-(2,3-dichlorobenzyl)-5-methyl-4-oxo-3,4-dihydrothieno[2,3-d]-pyrimidine-6-carboxylate as synthesized in Production Example 8, in the manner similar to Example 1.

$^1$H-NMR (DMSO-$d_6$) δ: 2.80 (3H, s), 4.21 (2H, s), 7.3-7.7 (3H, m), 12.77 (1H, br s), 13.33 (1H, br s)

MS (m/z): 370 (M$^+$+2), 368 (M$^+$)

Example 35

2-(2,4-Dichlorobenzyl)-5-methyl-4-oxo-3,4-dihydrothieno-[2,3-d]pyrimidine-6-carboxylic acid

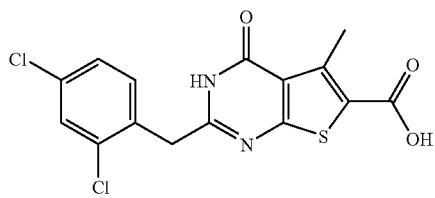

The title compound was synthesized from ethyl 2-(2,4-dichlorobenzyl)-5-methyl-4-oxo-3,4-dihydrothieno[2,3-d]-pyrimidine-6-carboxylate as synthesized in Production Example 9, in the manner similar to Example 1.

$^1$H-NMR (DMSO-$d_6$) δ: 2.80 (3H, s), 4.14 (2H, s), 7.3-7.7 (3H, m), 12.77 (1H, br s), 13.33 (1H, br s)

MS (m/z): 370 (M$^+$+2), 368 (M$^+$)

Example 36-a)

2-(3,4-Dichlorobenzyl)-5-methyl-4-oxo-3,4-dihydrothieno-[2,3-d]pyrimidine-6-carboxylic acid

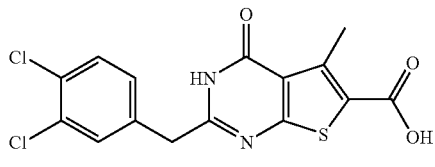

The title compound was synthesized from ethyl 2-(3,4-dichlorobenzyl)-5-methyl-4-oxo-3,4-dihydrothieno[2,3-d]-pyrimidine-6-carboxylate as synthesized in Production Example 10, in the manner similar to Example 1.

$^1$H-NMR (DMSO-$d_6$) δ: 2.79 (3H, s), 3.99 (2H, s), 7.3-7.7 (3H, m), 12.71 (1H, br s), 13.33 (1H, br s)

MS (m/z): 370 (M$^+$+2), 368 (M$^+$)

Example 36-b)

2-(3,4-Dichlorobenzyl)-5-methyl-4-oxo-3,4-dihydrothieno-[2,3-d]pyrimidine-6-carboxylic acid sodium salt

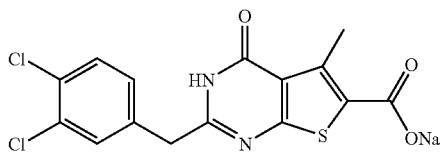

A sodium salt of the compound as synthesized in above Example 36-a) was obtained.

$^1$H-NMR (DMSO-$d_6$) δ: 2.73 (3H, s), 3.93 (2H, s), 7.34 (1H, dd, J=1.9, 8.5 Hz), 7.59 (1H, d, J=8.5 Hz), 7.64 (1H, d, J=1.9 Hz), 12.31 (1H, br s)

Example 36-c)

2-(3,4-Dichlorobenzyl)-5-methyl-4-oxo-3,4-dihydrothieno-[2,3-d]pyrimidine-6-carboxylic acid sodium salt.½ ethanolate

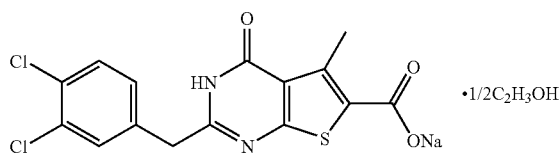

A sodium salt.½ ethanolate of the compound as synthesized in above Example 36-a) was obtained.

$^1$H-NMR (DMSO-$d_6$) δ: 1.06 (1.5H, t, J=7.0 Hz), 2.73 (3H, s), 3.4-3.5 (1H, m), 3.93 (2H, s), 4.34 (0.5H, br t), 7.34 (1H, dd, J=1.9, 8.5 Hz), 7.59 (1H, d, J=8.5 Hz), 7.64 (1H, d, J=1.9 Hz), 12.31 (1H, br s)

(The underlined part is the peak attributable to ethanol.)

Example 37

2-(3,4-Dimethoxybenzyl)-5-methyl-4-oxo-3,4-dihydrothieno-[2,3-d]pyrimidine-6-carboxylic acid

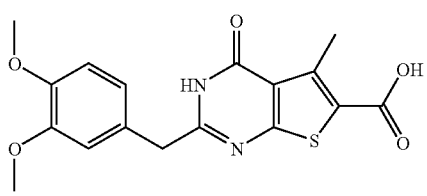

The title compound was synthesized from ethyl 2-(3,4-dimethoxybenzyl)-5-methyl-4-oxo-3,4-dihydrothieno[2,3-d]-pyrimidine-6-carboxylate which was synthesized similarly to Production Example 59, in the manner similar to Example 1.

$^1$H-NMR (DMSO-$d_6$) δ: 2.77 (3H, s), 3.70 (3H, s), 3.73 (3H, s), 3.89 (2H, s), 6.8-7.0 (2H, m), 6.99 (1H, d, J=2.0 Hz), 12.63 (1H, s)

MS (m/z): 360 (M$^+$, base)

Example 38

5-Methyl-2-(3,4-methylenedioxybenzyl)-4-oxo-3,4-dihydrothieno[2,3-d]pyrimidine-6-carboxylic acid

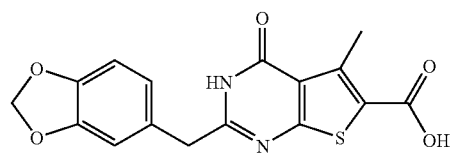

The title compound was synthesized from ethyl 5-methyl-2-(3,4-methylenedioxybenzyl)-4-oxo-3,4-dihydrothieno-[2,3-d]pyrimidine-6-carboxylate which was synthesized similarly to Production Example 59, in the manner similar to Example 1.

$^1$H-NMR (DMSO-$d_6$) δ: 2.80 (3H, s), 3.89 (2H, s), 6.00 (2H, s), 6.8-6.9 (2H, m), 6.98 (1H, s)

MS (m/z): 344 (M$^+$, base)

Example 39

5-Methyl-2-(4-methylthiobenzyl)-4-oxo-3,4-dihydrothieno-[2,3-d]pyrimidine-6-carboxylic acid

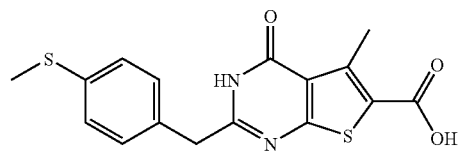

The title compound was synthesized from ethyl 5-methyl-2-(4-methylthiobenzyl)-4-oxo-3,4-dihydrothieno[2,3-d]-pyrimidine-6-carboxylate as synthesized in Production Example 74 in the manner similar to Example 1.

$^1$H-NMR (DMSO-$d_6$) δ: 2.44 (3H, s), 2.78 (3H, s), 3.91 (2H, s), 7.22 (2H, d, J=8.5 Hz), 7.30 (2H, d, J=8.5 Hz), 12.51 (1H, br s), 12.69 (1H, br s)

MS (m/z): 346 (M$^+$)

Example 40

5-Methyl-4-oxo-2-(2-trifluoromethylthiobenzyl)-3,4-dihydrothieno[2,3-d]pyrimidine-6-carboxylic acid

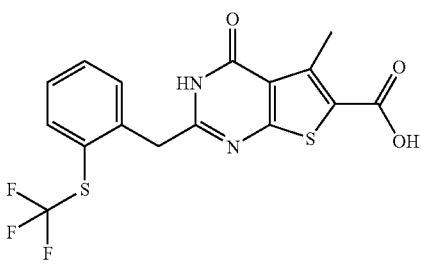

The title compound was synthesized from ethyl 5-methyl-4-oxo-2-(2-trifluoromethylthiobenzyl)-3,4-dihydrothieno[2,3-d]-pyrimidine-6-carboxylate as synthesized in Production Example 69 in the manner similar to Example 1.

$^1$H-NMR (DMSO-$d_6$) δ: 2.80 (3H, s), 4.32 (2H, s), 7.4-7.6 (3H, m), 7.7-7.8 (1H, m), 12.77 (1H, br s), 13.32 (1H, br s)

MS (m/z): 400 (M$^+$)

Example 41

2-(2-Carboxybenzyl)-5-methyl-4-oxo-3,4-dihydrothieno-[2,3-d]pyrimidine-6-carboxylic acid

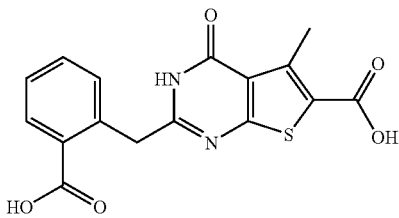

The title compound was synthesized from ethyl 2-(2-methoxycarbonylbenzyl)-5-methyl-4-oxo-3,4-dihydrothieno-[2,3-d]pyrimidine-6-carboxylate as synthesized in Production Example 35, in the manner similar to Example 1.

$^1$H-NMR (DMSO-$d_6$) δ: 2.80 (3H, s), 4.36 (2H, s), 7.3-7.5 (2H, m), 7.55 (1H, dt, J=1.5, 7.7 Hz), 7.91 (1H, dd, J=1.5, 7.7 Hz), 12.62 (1H, br s), 13.04 (1H, br s)

MS (m/z): 344 (M$^+$), 326 (base)

Example 42

2-(Biphenyl-4-ylmethyl)-5-methyl-4-oxo-3,4-dihydrothieno-[2,3-d]pyrimidine-6-carboxylic acid

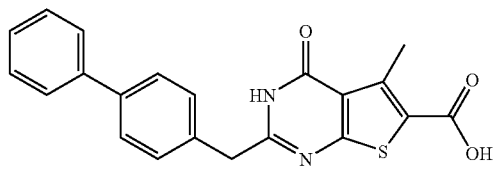

The title compound was synthesized from ethyl 2-(biphenyl-4-ylmethyl)-5-methyl-4-oxo-3,4-dihydrothieno-[2,3-d]pyrimidine-6-carboxylate as synthesized similarly to Production Example 37, in the manner similar to Example 1.

$^1$H-NMR (DMSO-$d_6$) δ: 2.78 (3H, s), 4.00 (2H, s), 7.3-7.4 (1H, m), 7.4-7.5 (4H, m), 7.5-7.7 (4H, m), 12.77 (1H, s)

MS (m/z): 376 (M$^+$, base)

Example 43

2-(3-Bromo-4-methoxybenzyl)-5-methyl-4-oxo-3,4-dihydrothieno[2,3-d]-pyrimidine-6-carboxylic acid

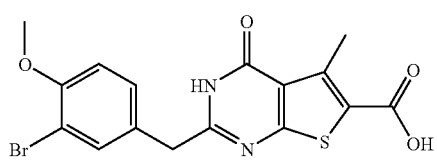

The title compound was synthesized from ethyl 2-(3-bromo-4-methoxybenzyl)-5-methyl-4-oxo-3,4-dihydrothieno-[2,3-d]pyrimidine-6-carboxylate as synthesized in Production Example 38, in the manner similar to Example 1.

$^1$H-NMR (DMSO-$d_6$) δ: 2.79 (3H, s), 3.82 (3H, s), 3.89 (2H, s), 7.07 (1H, d, J=8.5 Hz), 7.33 (1H, dd, J=1.9, 8.5 Hz), 7.60 (1H, d, J=1.9 Hz), 12.67 (1H, br s), 13.33 (1H, br s)

MS (m/z): 410 (M$^+$+2), 408 (M$^+$), 183 (base)

Example 44

2-(5-Bromo-2-methoxybenzyl)-5-methyl-4-oxo-3,4-dihydrothieno[2,3-d]pyrimidine-6-carboxylic acid

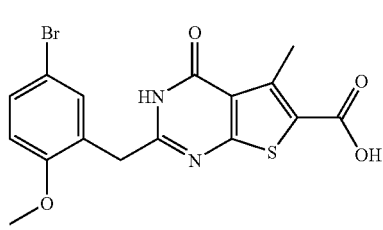

The title compound was synthesized from ethyl 2-(5-bromo-2-methoxybenzyl)-5-methyl-4-oxo-3,4-dihydrothieno-[2,3-d]pyrimidine-6-carboxylate as synthesized in Production Example 57, in the manner similar to Example 1.

¹H-NMR (DMSO-d₆) δ: 2.80 (3H, s), 3.72 (3H, s), 3.94 (2H, s), 6.97 (1H, d, J=8.9 Hz), 7.4-7.5 (2H, m), 12.62 (1H, br s), 13.31 (1H, br s)

MS (m/z): 410 (M⁺+2), 408 (M⁺)

Example 45

2-(2-Chloro-5-trifluoromethylbenzyl)-5-methyl-4-oxo-3,4-dihydrothieno[2,3-d]pyrimidine-6-carboxylic acid

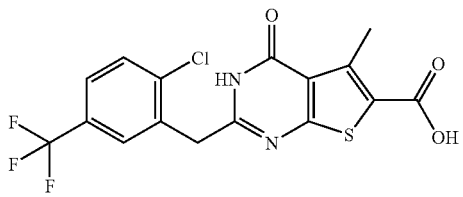

The title compound was synthesized from ethyl 2-(2-chloro-5-trifluoromethylbenzyl)-5-methyl-4-oxo-3,4-dihydrothieno[2,3-d]pyrimidine-6-carboxylate as synthesized in Production Example 39, in the manner similar to Example 1.

¹H-NMR (DMSO-d₆) δ: 2.80 (3H, s), 4.27 (2H, s), 7.72 (2H, d, J=1.5 Hz), 7.90 (1H, s), 12.80 (1H, br s), 13.33 (1H, br s)

MS (m/z): 404 (M⁺+2), 402 (M⁺), 367 (base)

Example 46

2-(2-Fluoro-3-trifluoromethylbenzyl)-5-methyl-4-oxo-3,4-dihydrothieno[2,3-d]pyrimidine-6-carboxylic acid

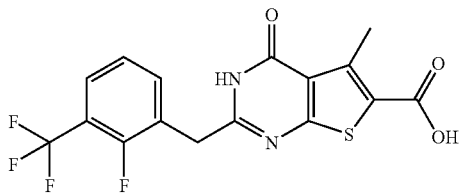

The title compound was synthesized from ethyl 2-(2-fluoro-3-trifluoromethylbenzyl)-5-methyl-4-oxo-3,4-dihydrothieno[2,3-d]pyrimidine-6-carboxylate as synthesized in Production Example 40, in the manner similar to Example 1.

¹H-NMR (DMSO-d₆) δ: 2.80 (3H, s), 4.15 (2H, s), 7.3-7.5 (1H, m), 7.6-7.8 (2H, m), 12.78 (1H, s), 13.33 (1H, s)

MS (m/z): 386 (M⁺)

Example 47

2-(2-Fluoro-5-trifluoromethylbenzyl)-5-methyl-4-oxo-3,4-dihydrothieno[2,3-d]pyrimidine-6-carboxylic acid The title compound was synthesized from ethyl 2-(2-fluoro-5-trifluoromethylbenzyl)-5-methyl-4-oxo-3,4-dihydrothieno[2,3-d]pyrimidine-6-carboxylate as synthesized in Production Example 41, in the manner similar to Example 1.

¹H-NMR (DMSO-d₆) δ: 2.80 (3H, s), 4.16 (2H, s), 7.45 (1H, t, J=9.1 Hz), 7.7-7.8 (1H, m), 7.90 (1H, dd, J=2.1, 6.7 Hz), 12.77 (1H, br s), 13.36 (1H, br s)

MS (m/z): 386 (M⁺, base)

Example 48

2-(3-Fluoro-5-trifluoromethylbenzyl)-5-methyl-4-oxo-3,4-dihydrothieno[2,3-d]pyrimidine-6-carboxylic acid

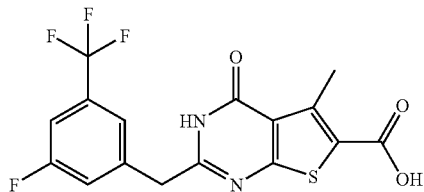

The title compound was synthesized from ethyl 2-(3-fluoro-5-trifluoromethylbenzyl)-5-methyl-4-oxo-3,4-dihydrothieno-[2,3-d]pyrimidine-6-carboxylate as synthesized in Production Example 58, in the manner similar to Example 1.

¹H-NMR (DMSO-d₆) δ: 2.79 (3H, s), 4.13 (2H, s), 7.5-7.6 (3H, m), 12.76 (1H, br s), 13.34 (1H, br s)

MS (m/z): 386 (M⁺)

Example 49

2-(4-Fluoro-3-trifluoromethylbenzyl)-5-methyl-4-oxo-3,4-dihydrothieno[2,3-d]pyrimidine-6-carboxylic acid

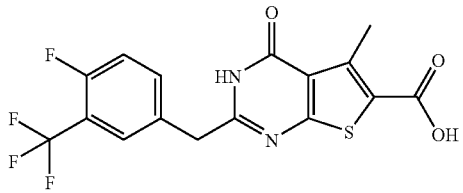

The title compound was synthesized from ethyl 2-(4-fluoro-3-trifluoromethylbenzyl)-5-methyl-4-oxo-3,4-dihydrothieno[2,3-d]pyrimidine-6-carboxylate as synthesized in Production Example 64, in the manner similar to Example 1.

$^1$H-NMR (DMSO-d$_6$) δ: 2.79 (3H, s), 4.07 (2H, s), 7.4-7.5 (1H, m), 7.6-7.8 (1H, m), 7.8-7.9 (1H, m), 12.73 (1H, br s), 13.34 (1H, br s)

MS (m/z): 386 (M$^+$)

Example 50

2-(5-Fluoro-2-trifluoromethylbenzyl)-5-methyl-4-oxo-3,4-dihydrothieno[2,3-d]pyrimidine-6-carboxylic acid

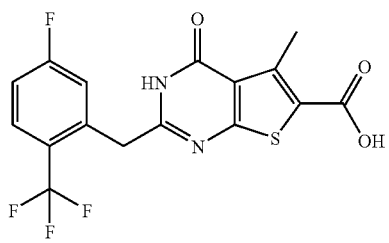

The title compound was synthesized from ethyl 2-(5-fluoro-2-trifluoromethylbenzyl)-5-methyl-4-oxo-3,4-dihydrothieno[2,3-d]pyrimidine-6-carboxylate as synthesized in Production Example 75, in the manner similar to Example 1.

$^1$H-NMR (DMSO-d$_6$) δ: 2.80 (3H, s), 4.25 (2H, s), 7.3-7.5 (2H, m), 7.8-7.9 (1H, m), 12.76 (1H, s), 13.35 (1H, br s)

MS (m/z): 386 (M$^+$)

Example 51

2-(3-Chloro-2-fluorobenzyl)-5-methyl-4-oxo-3,4-dihydrothieno[2,3-d]pyrimidine-6-carboxylic acid

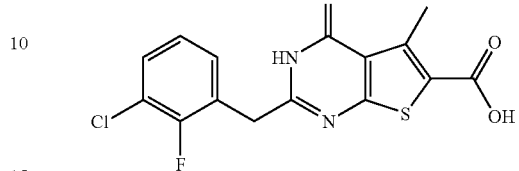

The title compound was synthesized from ethyl 2-(3-chloro-2-fluorobenzyl)-5-methyl-4-oxo-3,4-dihydrothieno[2,3-d]pyrimidine-6-carboxylate as synthesized in Production Example 42, in the manner similar to Example 1.

$^1$H-NMR (DMSO-d$_6$) δ: 2.80 (3H, s), 4.10 (2H, s), 7.21 (1H, dt, J=1.0, 7.9 Hz), 7.3-7.4 (1H, m), 7.4-7.6 (1H, m), 12.76 (1H, br s), 13.34 (1H, br s)

MS (m/z): 354 (M$^+$+2), 352 (M$^+$), 143 (base)

Example 52

2-(3-Chloro-4-fluorobenzyl)-5-methyl-4-oxo-3,4-dihydrothieno[2,3-d]pyrimidine-6-carboxylic acid

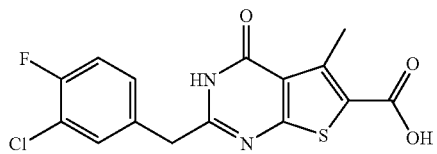

The title compound was synthesized from ethyl 2-(3-chloro-4-fluorobenzyl)-5-methyl-4-oxo-3,4-dihydrothieno[2,3-d]pyrimidine-6-carboxylate as synthesized in Production Example 43, in the manner similar to Example 1.

$^1$H-NMR (DMSO-d$_6$) δ: 2.79 (3H, s), 3.97 (2H, s), 7.3-7.5 (2H, m), 7.5-7.7 (1H, m), 12.69 (1H, br s), 13.34 (1H, br s)

MS (m/z): 354 (M$^+$+2), 352 (M$^+$), 183 (base)

Example 53

2-(5-Chloro-2-fluorobenzyl)-5-methyl-4-oxo-3,4-dihydrothieno[2,3-d]pyrimidine-6-carboxylic acid

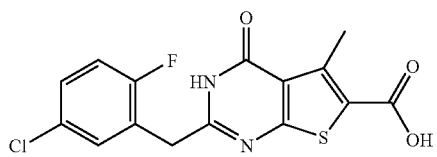

The title compound was synthesized from ethyl 2-(5-chloro-2-fluorobenzyl)-5-methyl-4-oxo-3,4-dihydrothieno[2,3-d]pyrimidine-6-carboxylate as synthesized in Production Example 44, in the manner similar to Example 1.

¹H-NMR (DMSO-d₆) δ: 2.80 (3H, s), 4.05 (2H, s), 7.26 (1H, t, J=9.1 Hz), 7.3-7.5 (1H, m), 7.52 (1H, dd, J=2.7, 6.2 Hz), 12.73 (1H, br s), 13.36 (1H, br s)

MS (m/z): 354 (M⁺+2), 352 (M⁺, base)

Example 54

2-(2-Chloro-6-fluorobenzyl)-5-methyl-4-oxo-3,4-dihydrothieno[2,3-d]pyrimidine-6-carboxylic acid

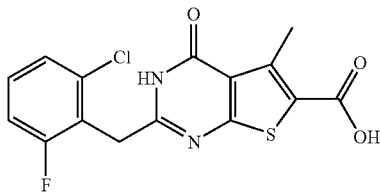

The title compound was synthesized from ethyl 2-(2-chloro-6-fluorobenzyl)-5-methyl-4-oxo-3,4-dihydrothieno[2,3-d]pyrimidine-6-carboxylate as synthesized in Production Example 66, in the manner similar to Example 1.

¹H-NMR (DMSO-d₆) δ: 2.80 (3H, s), 4.19 (2H, s), 7.2-7.3 (1H, m), 7.3-7.5 (2H, m), 12.84 (1H, br s), 13.32 (1H, br s)

MS (m/z): 354 (M⁺+2), 352 (M⁺)

Example 55

2-{3,5-Bis(trifluoromethyl)benzyl}-5-methyl-4-oxo-3,4-dihydrothieno[2,3-d]pyrimidine-6-carboxylic acid

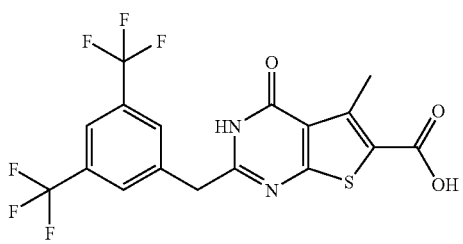

The title compound was synthesized from ethyl 2-{3,5-bis(trifluoromethyl)benzyl}-5-methyl-4-oxo-3,4-dihydrothieno[2,3-d]pyrimidine-6-carboxylate as synthesized in Production Example 51, in the manner similar to Example 1.

¹H-NMR (DMSO-d₆) δ: 2.78 (3H, s), 4.24 (2H, s), 8.02 (1H, s), 8.11 (2H, s), 12.78 (1H, br s), 13.34 (1H, br s)

MS (m/z): 436 (M⁺)

Example 56

2-(3,4-Difluorobenzyl)-5-methyl-4-oxo-3,4-dihydrothieno-[2,3-d]pyrimidine-6-carboxylic acid

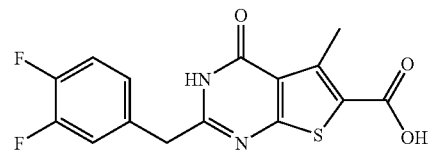

The title compound was synthesized from ethyl 2-(3,4-difluorobenzyl)-5-methyl-4-oxo-3,4-dihydrothieno[2,3-d]pyrimidine-6-carboxylate as synthesized in Production Example 52, in the manner similar to Example 1.

¹H-NMR (DMSO-d₆) δ: 2.79 (3H, s), 3.99 (2H, s), 7.1-7.5 (3H, m), 12.75 (1H, br s), 13.34 (1H, br s)

MS (m/z): 336 (M⁺)

Example 57

2-(2,5-Difluorobenzyl)-5-methyl-4-oxo-3,4-dihydrothieno-[2,3-d]pyrimidine-6-carboxylic acid

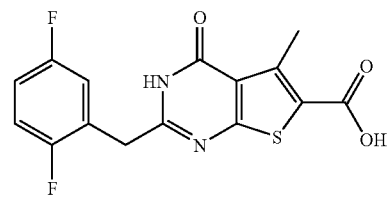

The title compound was synthesized from ethyl 2-(2,5-difluorobenzyl)-5-methyl-4-oxo-3,4-dihydrothieno[2,3-d]pyrimidine-6-carboxylate as synthesized in Production Example 53, in the manner similar to Example 1.

¹H-NMR (DMSO-d₆) δ: 2.80 (3H, s), 4.06 (2H, s), 7.1-7.4 (3H, m), 12.79 (1H, br s), 13.34 (1H, br s)

MS (m/z): 336 (M⁺)

Example 58

2-(2,4-Difluorobenzyl)-5-methyl-4-oxo-3,4-dihydrothieno-[2,3-d]pyrimidine-6-carboxylic acid

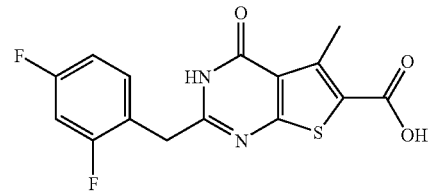

The title compound was synthesized from ethyl 2-(2,4-difluorobenzyl)-5-methyl-4-oxo-3,4-dihydrothieno[2,3-d]pyrimidine-6-carboxylate as synthesized in Production Example 65, in the manner similar to Example 1.

¹H-NMR (DMSO-d₆) δ: 2.80 (3H, s), 4.03 (2H, s), 7.0-7.1 (1H, m), 7.2-7.3 (1H, m), 7.4-7.5 (1H, m), 12.73 (1H, br s)
MS (m/z): 336 (M⁺)

Example 59

2-(2,6-Difluorobenzyl)-5-methyl-4-oxo-3,4-dihydrothieno-[2,3-d]pyrimidine-6-carboxylic acid

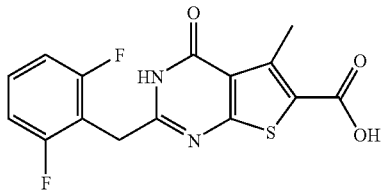

The title compound was synthesized from ethyl 2-(2,6-difluorobenzyl)-5-methyl-4-oxo-3,4-dihydrothieno[2,3-d]pyrimidine-6-carboxylate as synthesized in Production Example 67, in the manner similar to Example 1.
¹H-NMR (DMSO-d₆) δ: 2.79 (3H, s), 4.08 (2H, s), 7.1-7.2 (2H, m), 7.3-7.5 (1H, m), 12.78 (1H, br s)
MS (m/z): 336 (M⁺)

Example 60

5-Methyl-4-oxo-2-(2,3,5-trifluorobenzyl)-3,4-dihydrothieno-[2,3-d]pyrimidine-6-carboxylic acid

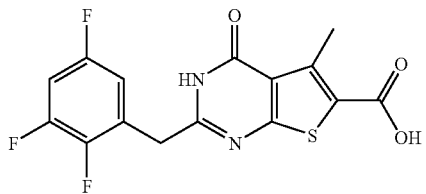

The title compound was synthesized from ethyl 5-methyl-4-oxo-2-(2,3,5-trifluorobenzyl)-3,4-dihydrothieno[2,3-d]-pyrimidine-6-carboxylate as synthesized in Production Example 70, in the manner similar to Example 1.
¹H-NMR (DMSO-d₆) δ: 2.80 (3H, s), 4.11 (2H, s), 7.1-7.3 (1H, m), 7.4-7.6 (1H, m), 12.73 (1H, s)
MS (m/z): 354 (M⁺)

Example 61

5-Methyl-2-(naphthalen-1-ylmethyl)-4-oxo-3,4-dihydrothieno-[2,3-d]pyrimidine-6-carboxylic acid

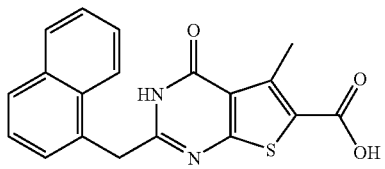

The title compound was synthesized from ethyl 5-methyl-2-(naphthalen-1-ylmethyl)-4-oxo-3,4-dihydrothieno-[2,3-d]pyrimidine-6-carboxylate which was synthesized similarly to Production Example 37, in the manner similar to Example 1.
¹H-NMR (DMSO-d₆) δ: 2.78 (3H, s), 4.45 (2H, s), 7.4-7.5 (1H, m), 7.5-7.6 (3H, m), 7.8-7.9 (1H, m), 7.9-8.0 (1H, m), 8.13 (1H, d, J=8.3 Hz), 12.74 (1H, br s)
MS (m/z): 350 (M⁺), 167 (base)

Example 62

2-(α-Hydroxybenzyl)-5-methyl-4-oxo-3,4-dihydrothieno-[2,3-d]pyrimidine-6-carboxylic acid

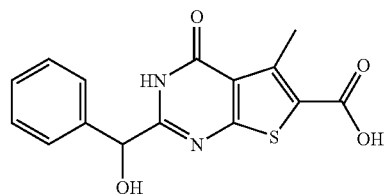

The title compound was synthesized from ethyl 2-(α-hydroxybenzyl)-5-methyl-4-oxo-3,4-dihydrothieno-[2,3-d]pyrimidine-6-carboxylate which was synthesized similarly to Production Example 37, in the manner similar to Example 1.
¹H-NMR (DMSO-d₆) δ: 2.78 (3H, s), 5.59 (1H, s), 6.51 (1H, br s), 7.2-7.3 (1H, m), 7.3-7.4 (2H, m), 7.52 (2H, d, J=7.3 Hz), 12.33 (1H, br s)
MS (m/z): 316 (M⁺), 298 (base)

Example 63

2-Benzhydryl-5-methyl-4-oxo-3,4-dihydrothieno-[2,3-d]pyrimidine-6-carboxylic acid

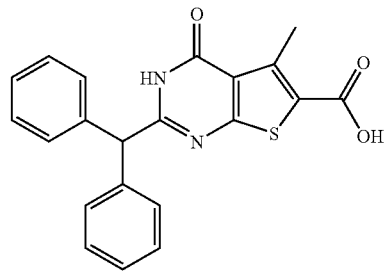

The title compound was synthesized from ethyl 2-benzhydryl-5-methyl-4-oxo-3,4-dihydrothieno-[2,3-d]pyrimidine-6-carboxylate as synthesized in Production Example 37, in the manner similar to Example 1.
¹H-NMR (DMSO-d₆) δ: 2.80 (3H, s), 5.52 (1H, s), 7.2-7.4 (10H, m), 12.82 (1H, br s), 13.5 (1H, br s)
MS (m/z): 376 (M⁺, base)

Example 64

5-Methyl-4-oxo-2-(pyridin-2-ylmethyl)-3,4-dihydrothieno-[2,3-d]pyrimidine-6-carboxylic acid

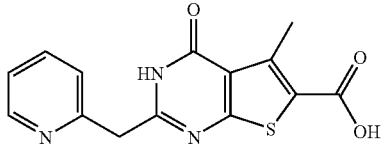

The title compound was synthesized from ethyl 5-methyl-4-oxo-2-(pyridin-2-ylmethyl)-3,4-dihydrothieno[2,3-d]pyrimidine-6-carboxylate as synthesized in Production Example 36, in the manner similar to Example 1.

$^1$H-NMR (DMSO-d$_6$) δ: 2.81 (3H, s), 4.17 (2H, s), 7.2-7.5 (2H, m), 7.77 (1H, dt, J=1.9, 7.7 Hz), 8.49 (1H, br s), 12.70 (1H, br s), 13.33 (1H, br s)

MS (m/z): 301 (M$^+$, base)

Example 65

2-(Cyclopent-1-enylmethyl)-5-methyl-4-oxo-3,4-dihydrothieno[2,3-d]pyrimidine-6-carboxylic acid

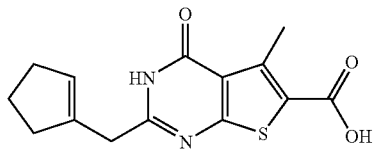

The title compound was synthesized from ethyl 2-(cyclopent-1-enylmethyl)-5-methyl-4-oxo-3,4-dihydrothieno-[2,3-d]pyrimidine-6-carboxylate as synthesized in Production Example 18, in the manner similar to Example 1.

$^1$H-NMR (DMSO-d$_6$) δ: 1.7-1.9 (2H, m), 2.2-2.4 (4H, m), 2.80 (3H, s), 3.41 (2H, s), 5.48 (1H, s), 12.51 (1H, br s), 13.31 (1H, br s)

MS (m/z): 290 (M$^+$)

Example 66

2-(Cyclohex-1-enylmethyl)-5-methyl-4-oxo-3,4-dihydrothieno[2,3-d]pyrimidine-6-carboxylic acid

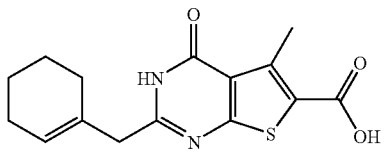

The title compound was synthesized from ethyl 2-(cyclohex-1-enylmethyl)-5-methyl-4-oxo-3,4-dihydrothieno[2,3-d]pyrimidine-6-carboxylate as synthesized similarly to Production Example 18, in the manner similar to Example 1.

$^1$H-NMR (DMSO-d$_6$) δ: 1.4-1.5 (2H, m), 1.5-1.6 (2H, m), 1.9-2.0 (4H, m), 2.77 (3H, s), 3.23 (2H, s), 5.52 (1H, s), 12.42 (1H, s)

MS (m/z): 304 (M$^+$), 262 (base)

Example 67

2-Cyclopentylmethyl-5-methyl-4-oxo-3,4-dihydrothieno-[2,3-d]pyrimidine-6-carboxylic acid

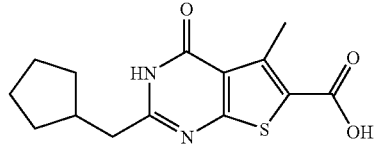

The title compound was synthesized from ethyl 2-cyclopentylmethyl-5-methyl-4-oxo-3,4-dihydrothieno-[2,3-d]pyrimidine-6-carboxylate as synthesized in Production Example 19, in the manner similar to Example 1.

$^1$H-NMR (DMSO-d$_6$) δ: 1.1-1.8 (8H, m), 2.2-2.4 (1H, m), 2.61 (2H, d, J=7.7 Hz), 2.80 (3H, s), 12.44 (1H, br s), 13.29 (1H, br s)

MS (m/z): 292 (M$^+$)

Example 68

2-Cyclohexylmethyl-5-methyl-4-oxo-3,4-dihydrothieno-[2,3-d]pyrimidine-6-carboxylic acid

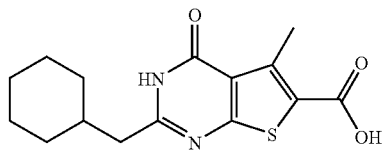

The title compound was synthesized from ethyl 2-cyclohexylmethyl-5-methyl-4-oxo-3,4-dihydrothieno-[2,3-d]pyrimidine-6-carboxylate as synthesized in Production Example 20, in the manner similar to Example 1.

$^1$H-NMR (DMSO-d$_6$) δ: 0.9-1.3 (5H, m), 1.5-1.9 (6H, m), 2.79 (3H, s), 12.42 (1H, br s)

MS (m/z): 306 (M$^+$)

Example 69

5-Methyl-4-oxo-2-piperidinomethyl-3,4-dihydrothieno[2,3-d]-pyrimidine-6-carboxylic acid

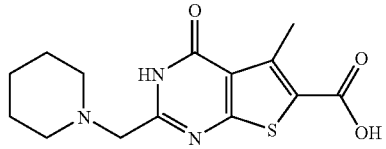

671 Milligrams of ethyl 5-methyl-4-oxo-2-piperidinomethyl-3,4-dihydrothieno[2,3-d]pyrimidine-6-carboxylate was suspended in 8 mL of 0.5N sodium hydroxide, stirred at 80° C. for 2 hours, and allowed to cool off. The reaction liquid was neutralized with 2N hydrochloric acid, and the precipitate was recovered by filtration and dried, to provide 565 mg (92%) of the title compound.

$^1$H-NMR (DMSO-d$_6$) δ: 1.3-1.4 (2H, m), 1.5-1.6 (4H, m), 2.80 (3H, s), 3.44 (2H, s)

MS (m/z): 307 (M$^+$), 84 (base)

Example 70

5-Methyl-4-oxo-2-(4-oxopiperidinomethyl)-3,4-dihydrothieno[2,3-d]-pyrimidine-6-carboxylic acid

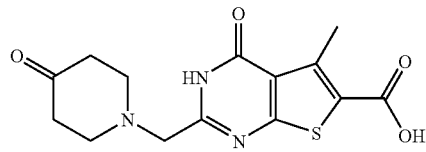

Using ethyl 2-chloromethyl-5-methyl-4-oxo-3,4-dihydrothieno-[2,3-d]pyrimidine-6-carboxylate and piperidin-4-one, a substitution reaction was carried out similarly to later appearing Production Example 21. Successively the reaction product was hydrolyzed similarly to Example 33, without intervening isolation of the reaction product, to provide the title compound.

$^1$H-NMR (DMSO-d$_6$) δ: 2.78 (3H, s), 2.9-3.8 (10H, m)

Example 71

2-(4-Carboxypiperidinomethyl)-5-methyl-4-oxo-3,4-dihydrothieno-[2,3-d]pyrimidine-6-carboxylic acid

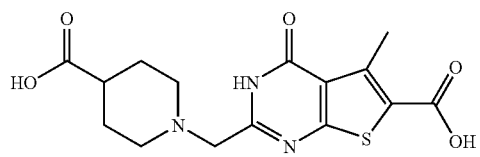

Example 70 was repeated except that piperidin-4-one was replaced with ethyl piperidine-4-carboxylate, to provide the title compound.

$^1$H-NMR (DMSO-d$_6$) δ: 1.6-1.8 (4H, m), 2.81 (3H, s), 3.1-3.2 (5H, m), 3.4-3.5 (2H, m)

Example 72

5-Methyl-2-(1-decahydroquinolylmethyl)-4-oxo-3,4-dihydrothieno[2,3-d]pyrimidine-6-carboxylic acid

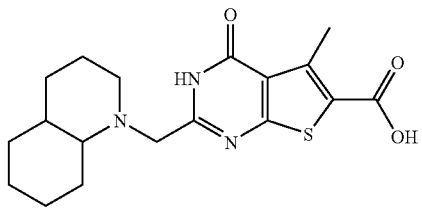

Example 70 was repeated except that piperidin-4-one was replaced with decahydroquinoline, to provide the title compound.

$^1$H-NMR (DMSO-d$_6$) δ: 1.7-2.0 (13H, m), 2.80 (3H, s)

Example 73 a: Synthesis of 2-(4-tert-butoxycarbonylpiperazin-1-ylmethyl)-5-methyl-4-oxo-3,4-dihydrothieno-[2,3-d]pyrimidine-6-carboxylic acid

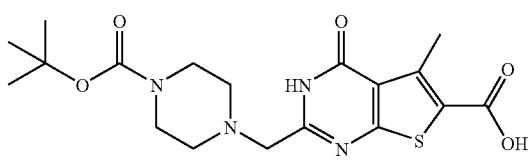

436 Milligrams of ethyl 2-(4-tert-butoxycarbonylpiperazin-1-ylmethyl)-5-methyl-4-oxo-3,4-dihydrothieno[2,3-d]pyrimidine-6-carboxylate as synthesized in Production Example 21 was suspended in 4 mL of 0.5N sodium hydroxide and stirred at 100° C. for 2 hours. After cooling off, the reaction liquid was neutralized with 1N hydrochloric acid, and the precipitate was recovered by filtration. Drying the same, 377 mg (92%) of the title compound was obtained.

b: Synthesis of 5-methyl-4-oxo-2-(piperazin-1-ylmethyl)-3,4-dihydrothieno[2,3-d]pyrimidine-6-carboxylic acid Dihydrochloride

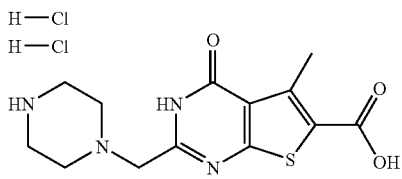

One-hundred (100) mg of the compound obtained in the above was dissolved in 4N hydrochloric acid/dioxane solution, and stirred for 2.5 hours. Distilling the solvent off under reduced pressure, 96 mg (quantitative) of the title compound was obtained.

$^1$H-NMR (DMSO-d$_6$) δ: 2.78 (4H, br s), 2.80 (3H, s), 3.12 (4H, br s), 3.5-3.7 (2H, m)

MS (m/z): 308 (M$^+$), 85 (base)

Example 74

2-(Octahydropyrrolo[1,2-a]pyrazin-2-ylmethyl-5-methyl-4-oxo-3,4-dihydrothieno-[2,3-d]pyrimidine-6-carboxylic acid

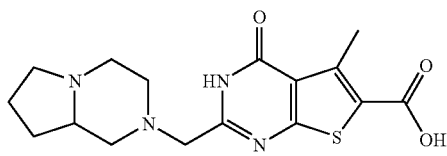

Example 70 was repeated except that piperidin-4-one was replaced with octahydropyrrolo[1,2-a]pyrazine, to provide the title compound.

$^1$H-NMR (DMSO-d$_6$) δ: 1.7-1.8 (4H, m), 2.78 (3H, s), 2.9-3.1 (7H, m), 3.4-3.6 (2H, m)

MS (m/z): 348 (M$^+$), 96 (base)

Compounds of Examples 75-88 were obtained in the manner similar to Example 1, as follows.

Example 75

5-Methyl-4-oxo-2-phenyl-3,4-dihydrothieno[2,3-d]pyrimidine-6-carboxylic acid

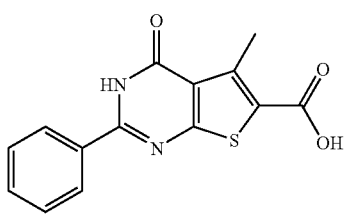

The title compound was synthesized from ethyl 5-methyl-4-oxo-2-phenyl-3,4-dihydrothieno[2,3-d]pyrimidine-6-carboxylate as synthesized in Production Example 60, in the manner similar to Example 1.

$^1$H-NMR (DMSO-d$_6$) δ: 2.89 (3H, s), 7.5-7.6 (3H, m), 8.1-8.2 (2H, m), 12.69 (1H, br s)

MS (m/z): 286 (M$^+$)

Example 76

5-Methyl-2-(2-naphthyl)-4-oxo-3,4-dihydrothieno-[2,3-d]pyrimidine-6-carboxylic acid

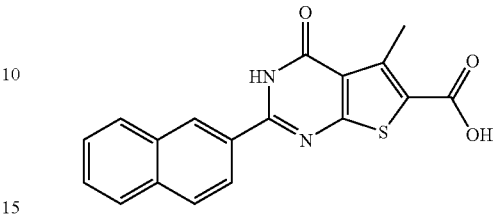

The title compound was synthesized from ethyl 5-methyl-2-(2-naphthyl)-4-oxo-3,4-dihydrothieno[2,3-d]pyrimidine-6-carboxylate as synthesized in Production Example 34, in the manner similar to Example 1.

$^1$H-NMR (DMSO-d$_6$) δ: 2.86 (3H, s), 7.5-7.7 (2H, m), 7.9-8.1 (3H, m), 8.23 (1H, dd, J=1.5, 8.9 Hz), 8.82 (1H, s), 12.8 (1H, br s)

MS (m/z): 336 (M$^+$), 139 (base)

Example 77

5-Methyl-4-oxo-2-(2-pyridyl)-3,4-dihydrothieno[2,3-d]-pyrimidine-6-carboxylic acid

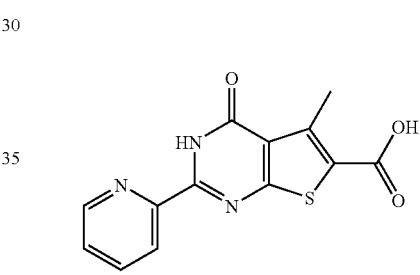

The title compound was synthesized from ethyl 5-methyl-4-oxo-2-(2-pyridyl)-3,4-dihydrothieno[2,3-d]pyrimidine-6-carboxylate which was synthesized similarly to Production Example 60, in the manner similar to Example 1.

MS (m/z): 287 (M$^+$, base)

Example 78

5-Methyl-4-oxo-2-(3-pyridyl)-3,4-dihydrothieno[2,3-d]-pyrimidine-6-carboxylic acid

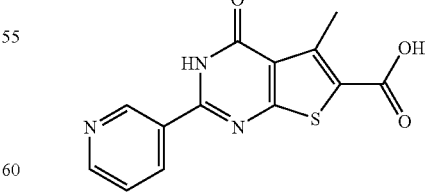

The title compound was synthesized from ethyl 5-methyl-4-oxo-2-(3-pyridyl)-3,4-dihydrothieno[2,3-d]pyrimidine-6-carboxylate which was synthesized similarly to Production Example 60, in the manner similar to Example 1

MS (m/z): 287 (M$^+$), 243 (base).

Example 79

5-Methyl-4-oxo-2-(pyrazin-2-yl)-3,4-dihydrothieno[2,3-d]-pyrimidine-6-carboxylic acid

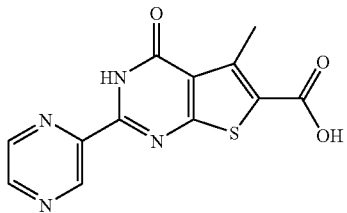

The title compound was synthesized from ethyl 5-methyl-4-oxo-2-(pyrazin-2-yl)-3,4-dihydrothieno[2,3-d]pyrimidine-6-carboxylate which was synthesized similarly to Production Example 60, in the manner similar to Example 1.

$^1$H-NMR (DMSO-$d_6$) δ: 2.84 (3H, s), 8.8-8.9 (1H, m), 8.88 (1H, d, J=2.7 Hz), 9.48 (1H, s), 12.33 (1H, br s)

MS (m/z): 288 (M$^+$, base)

Example 80

2-(2-Furyl)-5-methyl-4-oxo-3,4-dihydrothieno[2,3-d]-pyrimidine-6-carboxylic acid

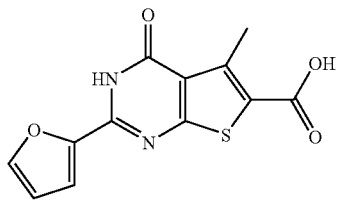

The title compound was synthesized from ethyl 2-(2-furyl)-5-methyl-4-oxo-3,4-dihydrothieno[2,3-d]pyrimidine-6-carboxylate which was synthesized similarly to Production Example 60, in the manner similar to Example 1.

$^1$H-NMR (DMSO-$d_6$) δ: 2.81 (3H, s), 6.7-6.8 (1H, m), 7.65 (1H, dd, J=0.6, 3.8 Hz), 8.0-8.1 (1H, m)

MS (m/z): 276 (M$^+$, base)

Example 81

5-Methyl-4-oxo-2-(thiophen-3-yl)-3,4-dihydrothieno[2,3-d]-pyrimidine-6-carboxylic acid

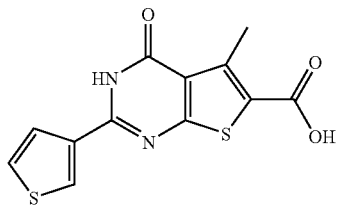

The title compound was synthesized from ethyl 5-methyl-4-oxo-2-(thiophen-3-yl)-3,4-dihydrothieno[2,3-d]pyrimidine-6-carboxylate as synthesized in Production Example 55, in the manner similar to Example 1.

$^1$H-NMR (DMSO-$d_6$) δ: 2.84 (3H, s), 7.7-7.8 (1H, m), 7.8-7.9 (1H, m), 8.66 (1H, s), 12.35 (1H, br s), 12.66 (1H, br s)

MS (m/z): 292 (M$^+$)

Example 82

5-Methyl-4-oxo-2-phenethyl-3,4-dihydrothieno[2,3-d]-pyrimidine-6-carboxylic acid

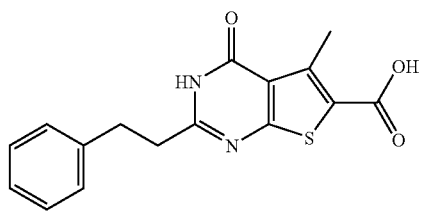

The title compound was synthesized from ethyl 5-methyl-4-oxo-2-phenethyl-3,4-dihydrothino[2,3-d]pyrimidine-6-carboxylate which was synthesized similarly to the preceding Production Example, in the manner similar to Example 1.

$^1$H-NMR (DMSO-$d_6$) δ: 2.79 (3H, s), 2.8-3.1 (4H, m), 7.1-7.4 (5H, m), 12.51 (1H, s)

MS (m/z): 314 (M$^+$, base)

Example 83

5-Methyl-4-oxo-2-(β-oxophenethyl)-3,4-dihydrothieno[2,3-d]-pyrimidine-6-carboxylic acid

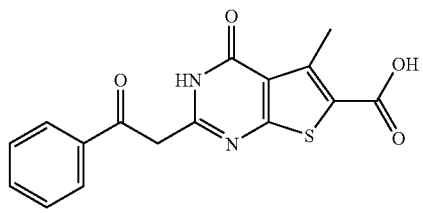

The title compound was synthesized from ethyl 5-methyl-4-oxo-2-(β-oxophenethyl)-3,4-dihydrothino[2,3-d]pyrimidine-6-carboxylate which was synthesized similarly to the preceding Production Example, in the manner similar to Example 1.

$^1$H-NMR (DMSO-$d_6$) δ: 2.80 (3H, s), 4.52 (2H, s), 7.5-8.1 (5H, m), 12.57 (1H, s)

MS (m/z): 328 (M$^+$), 105 (base)

Example 84

2-[2-(3-Chlorophenyl)-2-oxoethyl]-5-methyl-4-oxo-3,4-dihydrothieno[2,3-d]pyrimidine-6-carboxylic acid

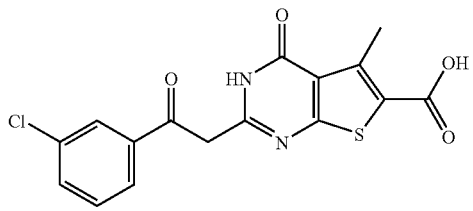

The title compound was synthesized from ethyl 2-[2-(3-chlorophenyl)-2-oxoethyl]-5-methyl-4-oxo-3,4-dihydrothieno-[2,3-d]pyrimidine-6-carboxylate which was synthesized similarly to the preceding Production Example, in the manner similar to Example 1.

$^1$H-NMR (DMSO-$d_6$) δ: 2.79 (3H, s), 4.55 (2H, s), 7.5-8.1 (4H, m), 12.58 (1H, s)

MS (m/z): 364 (M$^+$+2), 362 (M$^+$), 139 (base)

Example 85

2-Butyl-5-methyl-4-oxo-3,4-dihydrothieno[2,3-d]-pyrimidine-6-carboxylic acid

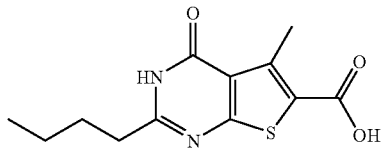

The title compound was synthesized from ethyl 2-butyl-5-methyl-4-oxo-3,4-dihydrothieno[2,3-d]pyrimidine-6-carboxylate which was synthesized similarly to the preceding Production Example, in the manner similar to Example 1.

$^1$H-NMR (DMSO-$d_6$) δ: 1.2-1.4 (3H, m), 1.9-2.0 (4H, m), 2.79 (3H, s), 12.46 (1H, s)

MS (m/z): 266 (M$^+$), 224 (base)

Example 86

2-Allyl-5-methyl-4-oxo-3,4-dihydrothieno[2,3-d]-pyrimidine-6-carboxylic acid

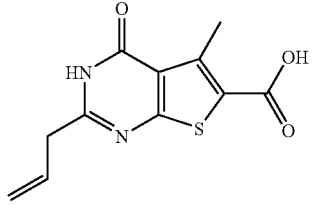

The title compound was synthesized from ethyl 2-allyl-5-methyl-4-oxo-3,4-dihydrothieno[2,3-d]pyrimidine-6-carboxylate which was synthesized similarly to the preceding Production Example, in the manner similar to Example 1.

$^1$H-NMR (DMSO-$d_6$) δ: 2.5-2.6 (2H, m), 2.79 (3H, s), 3.1-3.5 (3H, m), 12.46 (1H, s)

MS (m/z): 250 (M$^+$, base)

Example 87

5-Methyl-2-methylthio-4-oxo-3,4-dihydrothieno[2,3-d]-pyrimidine-6-carboxylic acid

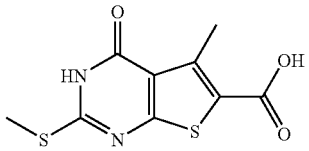

The title compound was synthesized from ethyl 5-methyl-2-methylthio-4-oxo-3,4-dihydrothieno[2,3-d]pyrimidine-6-carboxylate which was synthesized similarly to the preceding Production Example, in the manner similar to Example 1.

$^1$H-NMR (DMSO-$d_6$) δ: 2.53 (3H, s), 2.76 (3H, s)

MS (m/z): 256 (M$^+$)

Example 88

2-Carbamoylmethyl-5-methyl-4-oxo-3,4-dihydrothieno-[2,3-d]pyrimidine-6-carboxylic acid

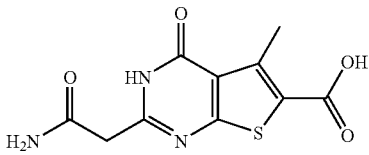

The title compound was synthesized from ethyl 2-carbamoylmethyl-5-methyl-4-oxo-3,4-dihydrothieno[2,3-d]-pyrimidine-6-carboxylate which was synthesized similarly to the preceding Production Example, in the manner similar to Example 1.

$^1$H-NMR (DMSO-$d_6$) δ: 2.80 (3H, s), 3.52 (2H, s), 7.16 (1H, s), 7.58 (1H, s), 12.47 (1H, s)

MS (m/z): 267 (M$^+$), 224 (base)

Example 89

2-(2-Aminoethyl)-5-methyl-4-oxo-3,4-dihydrothieno-[2,3-d]pyrimidine-6-carboxylic acid Hydrobromide

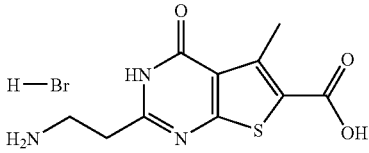

Using diethyl 5-amino-3-methylthiophene-2,4-dicarboxylate and benzyl N-(2-cyanoethyl)carbamate, the ring-closing reaction was carried out similarly to Production Example 1. Successively the hydrolysis was carried out similarly to Example 1, to provide 2-(2-benzyloxycarbonylaminoethyl)-5-methyl-4-oxo-3,4-dihydrothieno[2,3-d]pyrimidine-6-carboxylic acid.

A mixture of 387 mg of so obtained 2-(2-benzyloxycarbonyl-aminoethyl)-5-methyl-4-oxo-3,4-dihydrothieno[2,3-d]pyrimidine-6-carboxylic acid and 4.5 mL of hydrobromic acid was stirred at room temperature for 3 hours, and thereafter the solvent was distilled off under reduced pressure to provide 410 mg (quantitative) of the title compound.

$^1$H-NMR (DMSO-d$_6$) δ: 2.80 (3H, s), 2.9-3.0 (2H, m), 3.2-3.3 (2H, m), 7.80 (2H, br s), 12.58 (1H, br s)

MS (m/z): 253 (M$^+$)

Example 90

5-Methyl-4-oxo-2-phenoxy-3,4-dihydrothieno[2,3-d]-pyrimidine-6-carboxylic acid

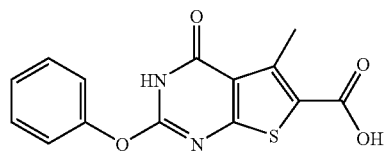

The title compound was synthesized from ethyl 5-methyl-4-oxo-2-phenoxy-3,4-dihydrothieno[2,3-d]pyrimidine-6-carboxylate as synthesized in Production Example 61, in the manner similar to Example 1.

$^1$H-NMR (DMSO-d$_6$) δ: 2.79 (3H, s), 7.2-7.5 (5H, m)

MS (m/z): 302 (M$^+$)

Example 91

5-Methyl-4-oxo-2-phenylthio-3,4-dihydrothieno[2,3-d]-pyrimidine-6-carboxylic acid

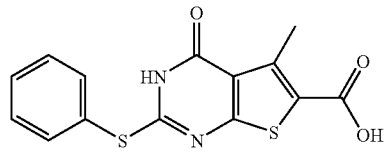

The title compound was synthesized from ethyl 5-methyl-4-oxo-2-phenylthio-3,4-dihydrothieno[2,3-d]pyrimidine-6-carboxylate as synthesized similarly to Production Example 61, in the manner similar to Example 1.

$^1$H-NMR (DMSO-d$_6$) δ: 2.77 (3H, s), 7.4-7.7 (5H, m), 13.02 (1H, br s), 13.29 (1H, br s)

MS (m/z): 318 (M$^+$)

Example 92

5-Methyl-4-oxo-2-phenylamino-3,4-dihydrothieno[2,3-d]-pyrimidine-6-carboxylic acid

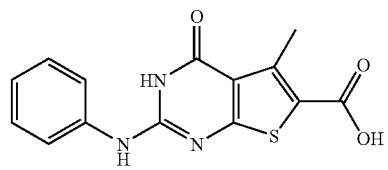

The title compound was synthesized from ethyl 5-methyl-4-oxo-2-phenylamino-3,4-dihydrothieno[2,3-d]pyrimidine-6-carboxylate as synthesized in Production Example 68, in the manner similar to Example 1.

$^1$H-NMR (DMSO-d$_6$) δ: 2.68 (1.2H, s), 2.70 (0.3H, s), 2.76 (1.5H, s), 7.3-7.6 (5H, m), 9.63 (0.5H, s), 11.16 (0.1H, s), 11.22 (0.4H, br s), 12.89 (1H, br s)

MS (m/z): 301 (M$^+$)

Example 93

3-Benzyl-2,5-dimethyl-4-oxo-3,4-dihydrothieno[2,3-d]-pyrimidine-6-carboxylic acid

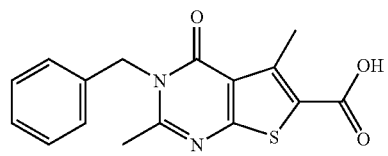

The title compound was synthesized from ethyl 3-benzyl-2,5-dimethyl-4-oxo-3,4-dihydrothieno[2,3-d]pyrimidine-6-carboxylate as synthesized in Production Example 22, in the manner similar to Example 1.

$^1$H-NMR (DMSO-d$_6$) δ: 2.23 (3H, s), 2.80 (3H, s), 5.32 (2H, s), 7.2-7.4 (5H, m)

MS (m/z): 314 (M$^+$), 91 (base)

Example 94

2-(3,4-Dichlorobenzyl)-3,5-dimethyl-4-oxo-3,4-dihydrothieno-[2,3-d]pyrimidine-6-carboxylic acid

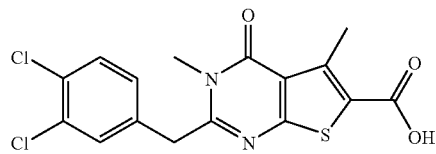

The title compound was synthesized from ethyl 2-(3,4-dichlorobenzyl)-3,5-dimethyl-4-oxo-3,4-dihydrothieno[2,3-d]-pyrimidine-6-carboxylate as synthesized in Production Example 23, in the manner similar to Example 1.

¹H-NMR (DMSO-d₆) δ: 2.44 (3H, s), 2.78 (3H, s), 3.88 (2H, s), 7.2-7.4 (1H, m), 7.5-7.6 (2H, m)

MS (m/z): 384 (M⁺+2), 382 (M⁺)

Example 95

3-Methyl-4-oxo-6,7,8,9-tetrahydro-4H-pyrido[1,2-a]thieno-[2,3-d]pyrimidine-2-carboxylic acid

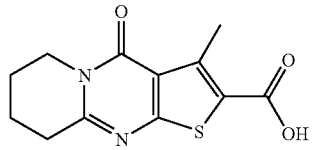

75 Milligrams of ethyl 3-methyl-4-oxo-6,7,8,9-tetrahydro-4H-pyrido[1,2-a]thieno[2,3-d]pyrimidine-6-carboxylate was suspended in a liquid mixture of 0.5 mL of ethanol, 1 mL of water and 1 mL of 1N aqueous sodium hydroxide solution, and stirred at about 100° C. for 2 hours. Thereafter 0.35 mL of 3N hydrochloric acid was added to the reaction mixture, to adjust the pH to 5. Distilling the mixture under reduced pressure, adequate amounts of chloroform and methanol were added to the residue to precipitate inorganic salts. The precipitated inorganic salts were removed by filtration and the filtrate was condensed under reduced pressure. Solidifying the residue by addition of hexane, 50 mg (74%) of the title compound was obtained.

¹H-NMR (DMSO-d₆) δ: 1.8-1.9 (2H, m), 2.0-2.1 (2H, m), 2.74 (3H, s), 2.77 (2H, t, J=6.6 Hz), 4.1-4.4 (2H, m)

MS (m/z): 264 (M⁺)

Example 96

2-(3,4-Dichlorobenzyl)-5-methyl-4-oxo-3,4-dihydrothieno-[2,3-d]pyrimidine-6-acetic Acid

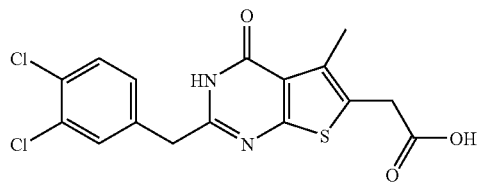

92 Milligrams of butyl 2-(3,4-dichlorobenzyl)-5-methyl-4-oxo-3,4-dihydrothieno[2,3-d]pyrimidine-6-acetate as synthesized in Production Example 25 was suspended in 1 mL of water and to which 0.63 mL of 1N aqueous sodium hydroxide solution was added, followed by an hour's stirring at about 70° C. Then the reaction mixture was neutralized with 0.63 mL of 1N hydrochloric acid, and the resulting precipitate was recovered by filtration and dried to provide 87 mg (quantitative) of the title compound.

¹H-NMR (DMSO-d₆) δ: 2.38 (3H, s), 3.77 (2H, s), 3.95 (2H, s), 7.3-7.4 (1H, m), 7.58 (1H, d, J=8.1 Hz), 7.63 (1H, d, J=1.9 Hz), 12.46 (1H, s)

MS (m/z): 384 (M⁺+2), 382 (M⁺)

The compounds of Examples 97-116 were synthesized in the manner similar to Example 1.

Example 97

2-(3,4-Dichlorobenzyl)-5-methyl-4-oxo-3,4-dihydrothieno-[2,3-d]pyrimidine-6-propionic Acid

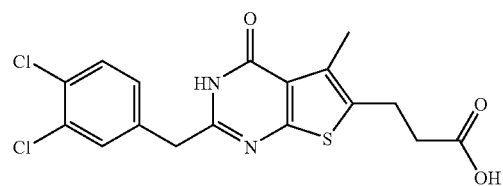

The title compound was synthesized from ethyl 2-(3,4-dichlorobenzyl)-5-methyl-4-oxo-3,4-dihydrothieno[2,3-d]pyrimidine-6-propionate as synthesized in Production Example 27, in the manner similar to Example 1.

¹H-NMR (DMSO-d₆) δ: 2.39 (3H, s), 2.97 (2H, t, J=7.3 Hz), 3.95 (2H, s), 7.2-7.7 (3H, m), 12.24 (1H, br s), 12.44 (1H, br s)

MS (m/z): 398 (M⁺+2), 396 (M⁺)

Example 98

2-(3,4-Dichlorobenzyl)-5-methyl-4-oxo-3,4-dihydrothieno-[2,3-d]pyrimidine-6-butyric acid

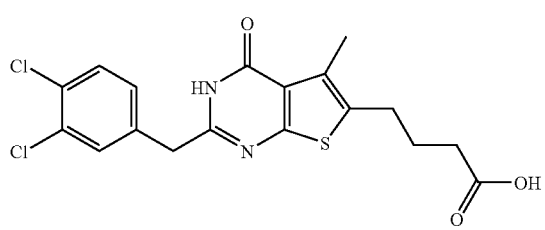

The title compound was synthesized from ethyl 2-(3,4-dichlorobenzyl)-5-methyl-4-oxo-3,4-dihydrothieno[2,3-d]pyrimidine-6-butyrate as synthesized in Production Example 29, in the manner similar to Example 1.

¹H-NMR (DMSO-d₆) δ: 1.7-1.9 (2H, m), 2.27 (2H, t, J=7.3 Hz), 2.37 (3H, s), 2.76 (2H, t, J=7.7 Hz), 3.95 (2H, s), 7.2-7.7 (3H, m), 12.08 (1H, br s), 12.43 (1H, br s)

MS (m/z): 412 (M⁺+2), 410 (M⁺)

Example 99

2-(3,4-Dichlorobenzyl)-4-oxo-5-trifluoromethyl-3,4-dihydrothieno[2,3-d]pyrimidine-6-carboxylic acid

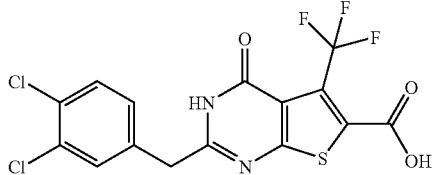

The title compound was synthesized from ethyl 2-(3,4-dichlorobenzyl)-4-oxo-5-trifluoromethyl-3,4-dihydrothieno[2,3-d]-pyrimidine-6-carboxylate as synthesized in Production Example 31, in the manner similar to Example 1.

$^1$H-NMR (DMSO-d$_6$) δ: 4.03 (2H, s), 7.3-7.7 (3H, m), 12.99 (1H, br s)

MS (m/z): 424 (M$^+$+2), 422 (M$^+$)

Example 100

2-(3,4-Dichlorobenzyl)-5-methoxymethyl-4-oxo-3,4-dihydrothieno[2,3-d]pyrimidine-6-carboxylic acid

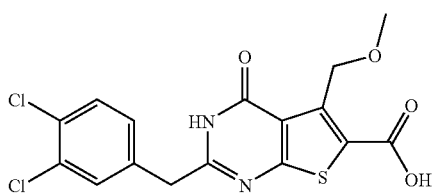

The title compound was synthesized from ethyl 2-(3,4-dichlorobenzyl)-5-methoxymethyl-4-oxo-3,4-dihydrothieno-[2,3-d]pyrimidine-6-carboxylate as synthesized in Production Example 33, in the manner similar to Example 1.

$^1$H-NMR (DMSO-d$_6$) δ: 3.71 (2H, s), 3.90 (3H, s), 3.94 (2H, s), 7.2-7.7 (3H, m), 12.18 (1H, br s), 12.48 (1H, br s)

MS (m/z): 400 (M$^+$+2), 398 (M$^+$)

Example 101

4-Oxo-2-(thiophen-3-ylmethyl)-3,4-dihydrothieno[2,3-d]-pyrimidine-6-carboxylic acid

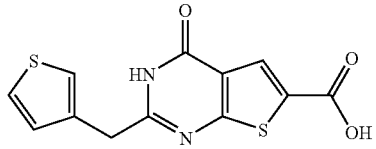

The title compound was synthesized from ethyl 4-oxo-2-(thiophen-3-ylmethyl)-3,4-dihydrothieno[2,3-d]pyrimidine-6-carboxylate as synthesized in Production Example 77, in the manner similar to Example 1.

$^1$H-NMR (DMSO-d$_6$) δ: 4.00 (2H, s), 7.10 (1H, dd, J=1.5, 5.0 Hz), 7.3-7.4 (1H, m), 7.49 (1H, dd, J=3.0, 5.0 Hz), 7.83 (1H, s), 12.83 (1H, s), 13.52 (1H, br s)

MS (m/z): 292 (M$^+$)

Example 102

4-Oxo-2-(thiophen-2-ylmethyl)-3,4-dihydrothieno[2,3-d]-pyrimidine-6-carboxylic acid

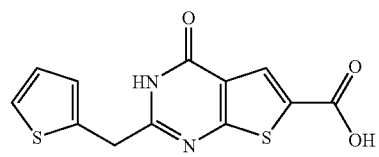

The title compound was synthesized from ethyl 4-oxo-2-(thiophen-2-ylmethyl)-3,4-dihydrothieno[2,3-d]pyrimidine-6-carboxylate as synthesized similarly to Production Example 77, in the manner similar to Example 1.

$^1$H-NMR (DMSO-d$_6$) δ: 4.20 (2H, s), 6.99 (1H, dd, J=3.5, 5.3 Hz), 7.0-7.1 (1H, m), 7.42 (1H, dd, J=1.2, 5.0 Hz), 7.85 (1H, s), 12.89 (1H, s), 13.57 (1H, br s)

MS (m/z): 292 (M$^+$)

Example 103

2-Benzyl-4-oxo-3,4-dihydrothieno[2,3-d]pyrimidine-6-carboxylic acid

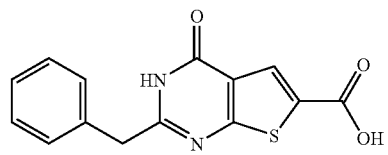

The title compound was synthesized from ethyl 2-benzyl-4-oxo-3,4-dihydrothieno[2,3-d]pyrimidine-6-carboxylate as synthesized in Production Example 45, in the manner similar to Example 1.

$^1$H-NMR (DMSO-d$_6$) δ: 3.99 (2H, s), 7.2-7.4 (5H, m), 7.84 (1H, s), 12.87 (1H, br s), 13.56 (1H, br s)

MS (m/z): 286 (M$^+$), 169 (base)

Example 104

2-(3-Chlorobenzyl)-4-oxo-3,4-dihydrothieno[2,3-d]pyrimidine-6-carboxylic acid

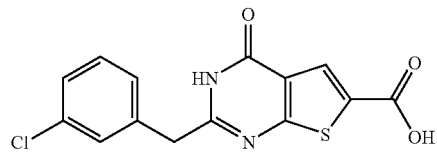

The title compound was synthesized from ethyl 2-(3-chlorobenzyl)-4-oxo-3,4-dihydrothieno[2,3-d]pyrimidine-6-carboxylate as synthesized in Production Example 76, in the manner similar to Example 1.

¹H-NMR (DMSO-d₆) δ: 4.01 (2H, s), 7.3-7.4 (3H, m), 7.4-7.5 (1H, m), 7.84 (1H, s), 12.87 (1H, s), 13.50 (1H, br s)
MS (m/z): 320 (M⁺)

Example 105

4-Oxo-2-(3-trifluoromethylbenzyl)-3,4-dihydrothieno-[2,3-d]pyrimidine-6-carboxylic acid

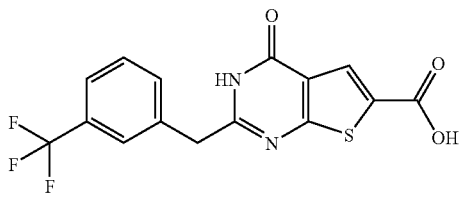

The title compound was synthesized from ethyl 4-oxo-2-(3-trifluoromethylbenzyl)-3,4-dihydrothieno[2,3-d]pyrimidine-6-carboxylate as synthesized in Production Example 79, in the manner similar to Example 1.
¹H-NMR (DMSO-d₆) δ: 4.11 (2H, s), 7.5-7.7 (3H, m), 7.77 (1H, s), 7.84 (1H, s), 12.89 (1H, s), 13.58 (1H, br s)
MS (m/z): 354 (M⁺)

Example 106

2-(3,4-Dichlorobenzyl)-4-oxo-3,4-dihydrothieno[2,3-d]-pyrimidine-6-carboxylic acid

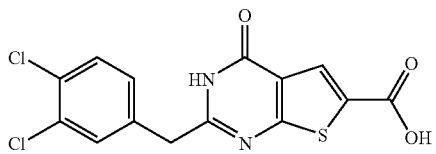

The title compound was synthesized from ethyl 2-(3,4-dichlorobenzyl)-4-oxo-3,4-dihydrothieno[2,3-d]pyrimidine-6-carboxylate as synthesized in Production Example 46, in the manner similar to Example 1.
¹H-NMR (DMSO-d₆) δ: 4.02 (2H, s), 7.36 (1H, dd, J=1.9, 8.3 Hz), 7.60 (1H, d, J=8.3 Hz), 7.66 (1H, d, J=1.9 Hz), 7.85 (1H, s), 12.85 (1H, br s), 13.57 (1H, br s)
MS (m/z): 356 (M⁺+2), 354 (M⁺), 169 (base)

Example 107

2-(Cyclopent-1-enylmethyl)-4-oxo-3,4-dihydrothieno[2,3-d]-pyrimidine-6-carboxylic acid

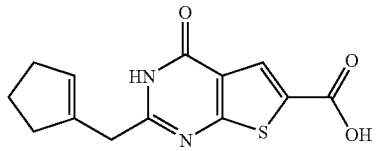

The title compound was synthesized from ethyl 2-(cyclopent-1-enylmethyl)-4-oxo-3,4-dihydrothieno[2,3-d]pyrimidine-6-carboxylate as synthesized in Production Example 78, in the manner similar to Example 1.
¹H-NMR (DMSO-d₆) δ: 1.3-1.4 (2H, m), 2.2-2.4 (4H, m), 3.44 (2H, s), 5.4-5.5 (1H, m), 7.85 (1H, s), 12.66 (1H, s), 13.55 (1H, br s)
MS (m/z): 276 (M⁺)

Example 108

5-Methyl-2-(thiophen-3-ylmethyl)-4-thioxo-3,4-dihydrothieno-[2,3-d]pyrimidine-6-carboxylic acid

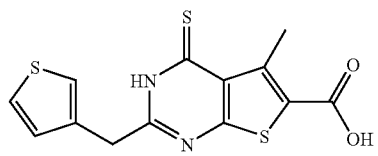

The title compound was synthesized from ethyl 5-methyl-2-(thiophen-3-ylmethyl)-4-thioxo-3,4-dihydrothieno[2,3-d]pyrimidine-6-carboxylate as synthesized in Production Example 87, in the manner similar to Example 1.
¹H-NMR (DMSO-d₆) δ: 3.05 (3H, s), 4.10 (2H, s), 7.10 (1H, dd, J=1.2, 5.0 Hz), 7.3-7.4 (1H, m), 7.4-7.6 (1H, m), 13.57 (1H, br s), 13.94 (1H, br s)
MS (m/z): 322 (M⁺, base)

Example 109

5-Methyl-2-(thiophen-2-ylmethyl)-4-thioxo-3,4-dihydrothieno-[2,3-d]pyrimidine-6-carboxylic acid

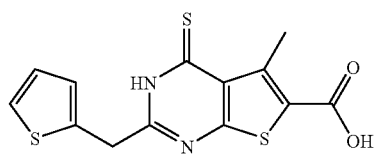

The title compound was synthesized from ethyl 5-methyl-2-(thiophen-2-ylmethyl)-4-thioxo-3,4-dihydrothieno[2,3-d]pyrimidine-6-carboxylate as synthesized in Production Example 85, in the manner similar to Example 1.
¹H-NMR (DMSO-d₆) δ: 3.05 (3H, s), 4.31 (2H, s), 6.99 (1H, dd, J=3.5, 5.0 Hz), 7.05 (1H, dd, J=1.3, 3.5 Hz), 7.43 (1H, dd, J=1.3, 5.0 Hz), 13.59 (1H, br s), 14.00 (1H, br s)
MS (m/z): 322 (M⁺), 97 (base)

Example 110

2-Benzyl-5-methyl-4-thioxo-3,4-dihydrothieno[2,3-d]-pyrimidine-6-carboxylic acid

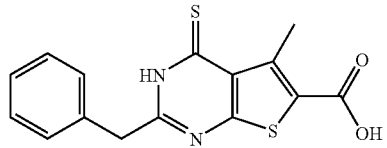

The title compound was synthesized from ethyl 2-benzyl-5-methyl-4-thioxo-3,4-dihydrothieno[2,3-d]pyrimidine-6-carboxylate as synthesized in Production Example 91, in the manner similar to Example 1.

$^1$H-NMR (DMSO-$d_6$) δ: 3.05 (3H, s), 4.10 (2H, s), 7.2-7.4 (5H, m), 13.56 (1H, br s), 13.98 (1H, br s)

MS (m/z): 316 (M$^+$, base)

Example 111

2-(3-Bromobenzyl)-5-methyl-4-thioxo-3,4-dihydrothieno-[2,3-d]pyrimidine-6-carboxylic acid

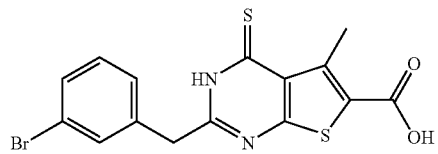

The title compound was synthesized from ethyl 2-(3-bromobenzyl)-5-methyl-4-thioxo-3,4-dihydrothieno[2,3-d]-pyrimidine-6-carboxylate as synthesized in Production Example 83, in the manner similar to Example 1.

$^1$H-NMR (DMSO-$d_6$) δ: 3.05 (3H, s), 4.11 (2H, s), 7.2-7.4 (2H, m), 7.4-7.5 (1H, m), 7.5-7.7 (1H, m), 13.58 (1H, br s), 13.97 (1H, br s)

MS (m/z): 396 (M$^+$+2, base), 394 (M$^+$)

Example 112

2-(3-Chlorobenzyl)-5-methyl-4-thioxo-3,4-dihydrothieno-[2,3-d]pyrimidine-6-carboxylic acid

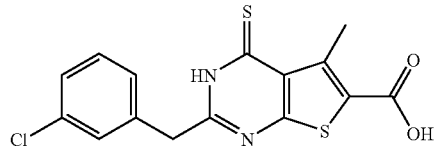

The title compound was synthesized from ethyl 2-(3-chlorobenzyl)-5-methyl-4-thioxo-3,4-dihydrothieno[2,3-d]-pyrimidine-6-carboxylate as synthesized in Production Example 93, in the manner similar to Example 1.

$^1$H-NMR (DMSO-$d_6$) δ: 3.05 (3H, s), 4.12 (2H, s), 7.2-7.5 (4H, m), 13.57 (1H, br s), 13.97 (1H, br s)

MS (m/z): 352 (M$^+$+2), 350 (M$^+$, base)

Example 113

5-Methyl-4-thioxo-2-(3-trifluoromethylbenzyl)-3,4-dihydrothieno[2,3-d]pyrimidine-6-carboxylic acid

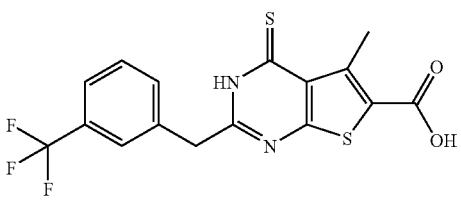

The title compound was synthesized from ethyl 5-methyl-4-thioxo-2-(trifluoromethylbenzyl)-3,4-dihydrothieno[2,3-d]pyrimidine-6-carboxylate as synthesized in Production Example 97, in the manner similar to Example 1.

$^1$H-NMR (DMSO-$d_6$) δ: 3.05 (3H, s), 4.22 (2H, s), 7.5-7.7 (3H, m), 7.78 (1H, s), 13.58 (1H, br s), 14.00 (1H, br s)

MS (m/z): 384 (M$^+$, base)

Example 114

2-(3,4-Dichlorobenzyl)-5-methyl-4-thioxo-3,4-dihydrothieno-[2,3-d]pyrimidine-6-carboxylic acid

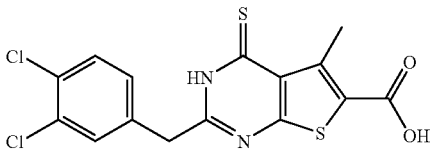

The title compound was synthesized from ethyl 2-(3,4-dichlorobenzyl)-5-methyl-4-thioxo-3,4-dihydrothieno[2,3-d]-pyrimidine-6-carboxylate as synthesized in Production Example 81, in the manner similar to Example 1.

$^1$H-NMR (DMSO-$d_6$) δ: 3.05 (3H, s), 4.13 (2H, s), 7.35 (1H, dd, J=1.9, 8.3 Hz), 7.60 (1H, d, J=8.3 Hz), 7.67 (1H, d, J=1.9 Hz), 13.57 (1H, br s), 14.96 (1H, br s)

MS (m/z): 386 (M$^+$+2), 384 (M$^+$, base)

Example 115

2-(3-Chloro-4-fluorobenzyl)-5-methyl-4-thioxo-3,4-dihydrothieno[2,3-d]pyrimidine-6-carboxylic acid

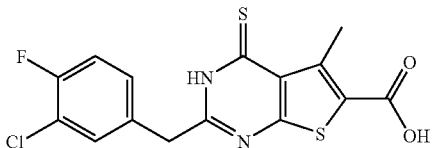

The title compound was synthesized from ethyl 2-(3-chloro-4-fluorobenzyl)-5-methyl-4-thioxo-3,4-dihydrothieno-[2,3-d]pyrimidine-6-carboxylate as synthesized in Production Example 95, in the manner similar to Example 1.

$^1$H-NMR (DMSO-$d_6$) δ: 3.05 (3H, s), 4.11 (2H, s), 7.3-7.5 (2H, m), 7.5-7.7 (1H, m), 13.59 (1H, br s), 13.97 (1H, br s)

MS (m/z): 370 (M$^+$+2), 368 (M$^+$, base)

Example 116

2-(Cyclohex-1-enylmethyl)-5-methyl-4-thioxo-3,4-dihydrothieno[2,3-d]pyrimidine-6-carboxylic acid

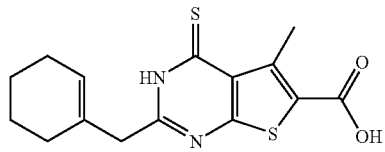

The title compound was synthesized from ethyl 2-(cyclohex-1-enylmethyl)-5-methyl-4-thioxo-3,4-dihydrothieno-[2,3-d]pyrimidine-6-carboxylate as synthesized in Production Example 89, in the manner similar to Example 1.

$^1$H-NMR (DMSO-$d_6$) δ: 1.4-1.7 (4H, m), 1.8-2.1 (4H, m), 3.06 (3H, s), 3.39 (2H, s), 5.53 (1H, s), 13.56 (1H, br s), 13.72 (1H, br s)

MS (m/z): 320 (M$^+$, base)

Example 117

2-(Cyclopent-1-enylmethyl)-5-methyl-4-thioxo-3,4-dihydrothieno[2,3-d]pyrimidine-6-carboxylic acid and 2-cyclopentylidenemethyl-5-methyl-4-thioxo-3,4-dihydrothieno-[2,3-d]pyrimidine-6-carboxylic acid

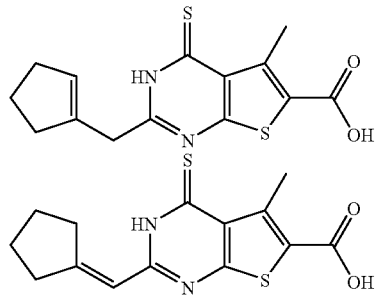

After carrying out the operations similar to Production Example 80, the resulting crystals were subjected to the operations similar to Production Example 81. Further following Example 1, the title compounds were obtained as a mixture.

Cyclopent-1-enylmethyl Form:

$^1$H-NMR (DMSO-$d_6$) δ: 1.7-1.9 (2H, m), 2.2-2.4 (4H, m), 3.06 (3H, s), 3.54 (2H, s), 5.4-5.5 (1H, m), 13.47 (1H, br s), 13.77 (1H, br s)

Cyclopentylidenemethyl Form:

$^1$H-NMR (DMSO-d) δ: 1.6-1.9 (4H, m), 2.4-2.7 (2H, m), 2.8-2.9 (2H, m), 3.06 (3H, s), 6.4-6.5 (1H, m), 13.47 (1H, br s), 13.77 (1H, br s)

MS (m/z): 314 (M$^+$)

The compounds of Examples 118-119 were synthesized in the manner similar to Example 1.

Example 118

2-Benzyl-4-thioxo-3,4-dihydrothieno[2,3-d]pyrimidine-6-carboxylic acid

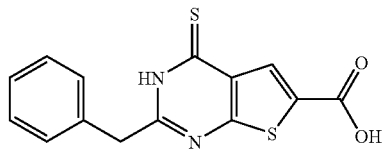

The title compound was synthesized from ethyl 2-benzyl-4-thioxo-3,4-dihydrothieno[2,3-d]pyrimidine-6-carboxylate as synthesized in Production Example 101, in the manner similar to Example 1.

$^1$H-NMR (DMSO-$d_6$) δ: 4.13 (2H, s), 7.2-7.4 (5H, m), 8.00 (1H, s), 13.77 (1H, br s), 14.26 (1H, br s)

MS (m/z): 302 (M$^+$, base)

Example 119

2-(3,4-Dichlorobenzyl)-4-thioxo-3,4-dihydrothieno[2,3-d]-pyrimidine-6-carboxylic acid

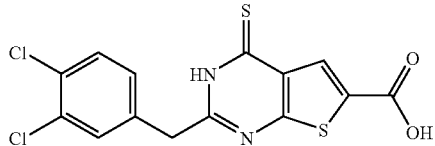

The title compound was synthesized from ethyl 2-(3,4-dichlorobenzyl)-4-thioxo-3,4-dihydrothieno[2,3-d]pyrimidine-6-carboxylate as synthesized in Production Example 99, in the manner similar to Example 1.

$^1$H-NMR (DMSO-$d_6$) δ: 4.16 (2H, s), 7.35 (1H, dd, J=1.9, 8.3 Hz), 7.61 (1H, d, J=8.3 Hz), 7.67 (1H, d, J=1.9 Hz), 8.01 (1H, s), 13.77 (1H, br s), 14.22 (1H, br s)

MS (m/z): 372 (M$^+$+2), 370 (M$^+$, base)

Formulation Example

Tablets

|  | mg/tablet |
| --- | --- |
| Active ingredient | 5.0 |
| Starch | 10.0 |
| Lactose | 73.0 |
| Carboxymethyl cellulose calcium | 10.0 |
| Talc | 1.0 |
| Magnesium stearate | 1.0 |
|  | 100.0 |

The active ingredient was pulverized to grain sizes not greater than 70 μm, to which starch, lactose and carboxymethyl cellulose calcium were added and thoroughly mixed. Then 10% starch paste was added to the powdery mixture and mixed by stirring to provide granules. After drying them, their grain sizes were dressed to around 1,000 μm, with which talc and magnesium stearate were mixed. The mixture was tabletted.

The invention claimed is:

1. A compound represented by the following formula (I)

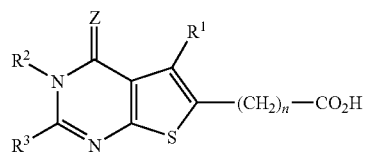

in which $R^1$ is hydrogen, $C_{1-6}$ alkyl, $C_{1-6}$ alkoxy$C_{1-6}$ alkyl or $C_{1-6}$ haloalkyl containing 1-6 halogen atoms, $R^2$ is hydrogen, $C_{1-6}$ alkyl, phenyl$C_{1-6}$ alkyl or amino, $R^3$ is $C_{2-6}$ alkyl, $C_{2-6}$ alkenyl, carbamoyl$C_{1-6}$ alkyl, amino$C_{1-6}$ alkyl, $C_{1-6}$ alkylamino$C_{1-6}$ alkyl, di-($C_{1-6}$ alkyl)amino$C_{1-6}$ alkyl, $C_{1-6}$ alkylthio or Y—X— group, or $R^2$ and $R^3$ may together form tetramethylene, X is a direct bond, or $CH_2$, $CH(OH)$, $CH(C_6H_5)$, $CO$, $CH_2CH_2$, $CH_2CO$, $COCH_2$, S, O or NH and Y is an aromatic carbocyclic group, aromatic heterocyclic group, 4-7-membered cycloalkyl group, 4-7-membered cycloalkenyl group, 5-7-membered saturated heterocyclic group containing 1 or 2 nitrogen atoms, or 5-7-membered saturated heterocyclic group forming a condensed ring with 5 or 6-membered saturated cyclic group and containing 1 or 2 nitrogen atoms, all of these groups optionally containing 1-3 substituents selected from the group consisting of halogen atom, $C_{1-6}$ alkyl, $C_{1-6}$ haloalkyl containing 1-6 halogen atoms, $C_{1-6}$ haloalkyloxy containing 1-6 halogen atoms, $C_{1-6}$ haloalkylthio containing 1-6 halogen atoms, $C_{1-6}$ alkoxy, $C_{1-6}$ alkylthio, $C_{1-4}$ alkylenedioxy, carboxyl, $C_{1-6}$ alkoxycarbonyl, oxo, amino, nitro and phenyl, Z is S or O, and n is 0 or an integer of 1-4, with the proviso that a case wherein $R^1$ is methyl, $R^2$ is hydrogen, $R^3$ is benzyl, Z is O and n is 0 is excluded, or a salt thereof.

2. The compound or salt thereof according to claim 1, in which $R^1$ is $C_{1-6}$ alkyl.

3. The compound or salt thereof according to claim 1, in which $R^2$ is hydrogen.

4. The compound or salt thereof according to claim 1, in which $R^3$ is Y—X— group.

5. The compound or salt thereof according to claim 4, in which X is $CH_2$, S, O or NH.

6. The compound or salt thereof according to claim 4, in which Y is an aromatic carbocyclic group or aromatic heterocyclic group, which are optionally substituted with 1-3 substituents selected from the group consisting of halogen, $C_{1-6}$ alkyl, $C_{1-6}$ haloalkyl containing 1-6 halogen atoms, $C_{1-6}$ haloalkyloxy containing 1-6 halogen atoms, $C_{1-6}$ haloalkylthio containing 1-6 halogen atoms, $C_{1-6}$ alkoxy, $C_{1-6}$ alkylthio, $C_{1-4}$ alkylenedioxy, carboxyl, $C_{1-6}$ alkoxycarbonyl, amino, nitro and phenyl.

7. The compound or salt thereof according to claim 1, in which Z is O.

8. The compound or salt thereof according to claim 1, in which n is 0.

9. A method of treating an overactive bladder syndrome, pollakiuria, urinary incontinence or learning and/or memory cognitive impairment, which comprises administering a therapeutically effective amount of a compound according to claim 1 or salt thereof to a patient in need thereof.

10. A method for preparing a pharmaceutical composition, which comprises combining a compound according to claim 1 or salt thereof with a pharmaceutically acceptable carrier.

11. A pharmaceutical composition comprising the compound according to claim 1 or salt thereof, and a pharmaceutically acceptable carrier.

12. 2-(3,4-Dichlorobenzyl)-5-methyl-4-oxo-3,4-dihydrothieno[2,3-d]pyrimidine-6-carboxylic acid or a salt thereof.

13. 2-(3-Chlorobenzyl)-5-methyl-4-oxo-3,4-dihydrothieno[2,3-d]pyrimidine-6-carboxylic acid or a salt thereof.

14. 5-Methyl-4-oxo-2-(3-trifluoromethylbenzyl)-3,4-dihydrothieno[2,3-d]pyrimidine-6-carboxylic acid or a salt thereof.

15. 2-(3-Chloro-4-fluorobenzyl)-5-methyl-4-oxo-3,4-dihydrothieno[2,3-d]pyrimidine-6-carboxylic acid or a salt thereof.

16. 2-(5-Chloro-2-fluorobenzyl)-5-methyl-4-oxo-3,4-dihydrothieno[2,3-d]pyrimidine-6-carboxylic acid or a salt thereof.

17. 2-(Cyclopent-1-enylmethyl)-5-methyl-4-oxo-3,4-dihydrothieno[2,3-d]pyrimidine-6-carboxylic acid or a salt thereof.

18. 4-Oxo-2-(thiophen-2-ylmethyl)-3,4-dihydrothieno[2,3-d]pyrimidine-6-carboxylic acid or a salt thereof.

19. 2-Benzyl-4-oxo-3,4-dihydrothieno[2,3-d]pyrimidine-6-carboxylic acid or a salt thereof.

20. 2-(3-Chlorobenzyl)-4-oxo-3,4-dihydrothieno[2,3-d]pyrimidine-6-carboxylic acid or a salt thereof.

21. 4-Oxo-2-(3-trifluoromethylbenzyl)-3,4-dihydrothieno-[2,3-d]pyrimidine-6-carboxylic acid or a salt thereof.

* * * * *